(12) United States Patent
Staid et al.

(10) Patent No.: US 12,146,487 B2
(45) Date of Patent: Nov. 19, 2024

(54) PUMP CARTRIDGE AND CONSOLE

(71) Applicant: PROCEPT BioRobotics Corporation, Redwood City, CA (US)

(72) Inventors: Kevin Staid, Lowell, MA (US); Lincoln Alvord, Redwood City, CA (US); Ruth Beeby, Santa Clara, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 605 days.

(21) Appl. No.: 17/310,777

(22) PCT Filed: Feb. 28, 2020

(86) PCT No.: PCT/US2020/020479
§ 371 (c)(1),
(2) Date: Aug. 24, 2021

(87) PCT Pub. No.: WO2020/180724
PCT Pub. Date: Sep. 10, 2020

(65) Prior Publication Data
US 2022/0186725 A1 Jun. 16, 2022

Related U.S. Application Data

(60) Provisional application No. 62/812,879, filed on Mar. 1, 2019.

(51) Int. Cl.
*F04B 53/14* (2006.01)
*A61B 17/3203* (2006.01)
*F04B 53/16* (2006.01)

(52) U.S. Cl.
CPC ........ *F04B 53/144* (2013.01); *A61B 17/3203* (2013.01); *F04B 53/16* (2013.01)

(58) Field of Classification Search
CPC ..... F04B 53/144; F04B 53/16; A61B 17/3203
See application file for complete search history.

(56) References Cited

U.S. PATENT DOCUMENTS

| 4,389,071 A | 6/1983 | Johnson, Jr. |
| 6,375,635 B1 | 4/2002 | Moutafis |

(Continued)

FOREIGN PATENT DOCUMENTS

| CN | 101394877 | 3/2009 |
| CN | 102905633 | 1/2013 |

(Continued)

OTHER PUBLICATIONS

International Search Report and Written Opinion for International Application No. PCT/US2020/020479, 13 pages (Jul. 17, 2020).

*Primary Examiner* — Connor J Tremarche
(74) *Attorney, Agent, or Firm* — FisherBroyles, LLP; John K. Shimmick

(57) ABSTRACT

A pump cartridge comprises a retention structure to retain a piston for shipping and storage, in which the piston can be decoupled from the retention structure to pump fluid. In the shipping and storage configuration, the piston can be positioned with the retention structure to allow sterilization gas to travel within a housing and into a cylinder distal to the piston. When placed in the console for use in a pumping configuration, the piston can be decoupled from the retention structure to form a seal within the housing. When the procedure has been completed, the pump cartridge can be decoupled from the console in a manner that disables the cartridge for subsequent use to prevent a non-sterile cartridge from being reused.

19 Claims, 50 Drawing Sheets

(56) References Cited

U.S. PATENT DOCUMENTS

| | | |
|---|---|---|
| 7,337,538 B2 | 3/2008 | Moutafis |
| 7,717,685 B2 | 5/2010 | Moutafis |
| 8,337,175 B2 | 12/2012 | Dion |
| 8,851,866 B2 | 10/2014 | Moutafis |
| 8,932,269 B2 | 1/2015 | Dion |
| 9,341,184 B2 | 5/2016 | Dion |
| 2002/0176788 A1 | 11/2002 | Moutafis |
| 2004/0230211 A1 | 11/2004 | Moutafis |
| 2004/0234380 A1* | 11/2004 | Moutafis ............... F04B 53/122 417/471 |
| 2006/0118495 A1 | 6/2006 | Kondratalv |
| 2006/0120899 A1 | 6/2006 | Sengun |
| 2007/0164046 A1 | 7/2007 | Nighy |
| 2010/0010524 A1 | 1/2010 | Barrington |
| 2011/0042413 A1* | 2/2011 | Nighy .................. B67D 1/0078 417/415 |
| 2011/0138997 A1 | 6/2011 | Pacht |
| 2011/0150680 A1* | 6/2011 | Dion .................... F04B 53/147 417/559 |
| 2011/0184391 A1 | 7/2011 | Aljuri |
| 2017/0354432 A1 | 12/2017 | Moser |

FOREIGN PATENT DOCUMENTS

| | | |
|---|---|---|
| CN | 107503930 | 12/2017 |
| EP | 0449692 | 10/1991 |
| FR | 2660021 | 9/1991 |
| JP | 2004525742 | 8/2004 |
| JP | 2013515210 | 5/2013 |
| WO | 2004004914 | 1/2004 |
| WO | 2008083407 | 7/2008 |
| WO | 2009111736 | 9/2009 |
| WO | 2011097505 | 8/2011 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2017161331 | 9/2017 |
| WO | 2019032986 | 2/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021096741 | 5/2021 |

* cited by examiner

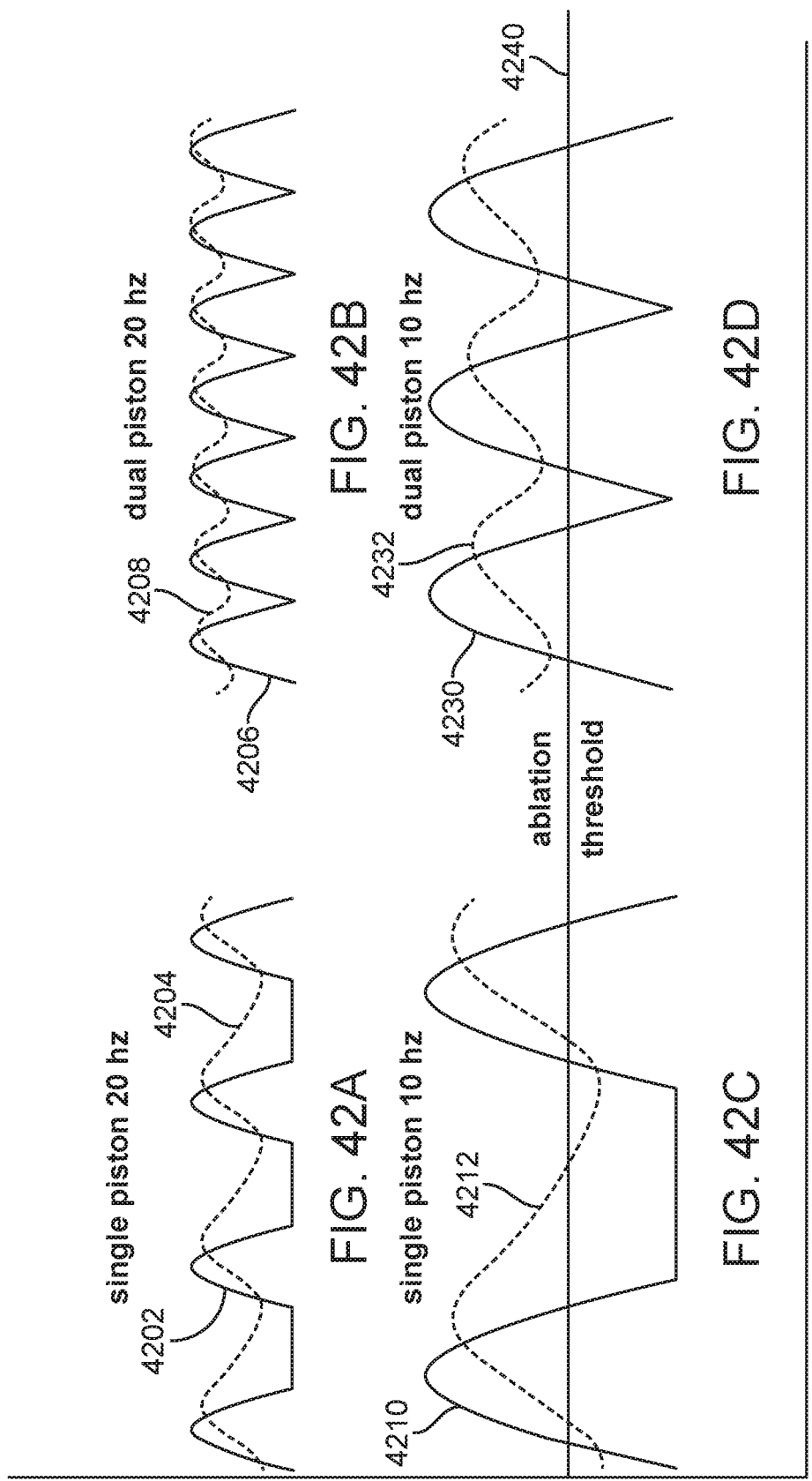

PUMP CARTRIDGE AND CONSOLE

RELATED APPLICATIONS

This application is a 371 national phase of International Patent Application No. PCT/US2020/020479, filed Feb. 28, 2020, published as WO 2020/180724 on Sep. 10, 2020, and claims the benefit under 35 U.S.C. § 119(e) of U.S. Provisional Patent Application No. 62/812,879, filed on Mar. 1, 2019, entitled Pump Cartridge, the entire disclosures of which are incorporated herein, in their entirety, by this reference.

BACKGROUND

High pressure liquid pumps can be used in many applications, such as machining and surgery. For example, waterjets can be used to resect tissue. Several surgical procedures have been developed in which water jets can be used to resect tissue, such as prostate surgery to remove benign prostate hyperplasia and spinal surgery. With surgical procedures it is beneficial, and in some instances required, to maintain sterility of the fluid being used to resect tissue of the patient. Although pumps can be reused and sterilized, this can be time consuming.

One prior approach to maintaining sterility has been to provide a sterile pump cartridge that can be used for a single surgery and then replaced. However, the prior pump cartridges for surgical procedures can be less than ideal in at least some instances. A pump cartridge may comprise several moving components and shipping and storage of at least some prior pump cartridges can be less than ideal. For a high-pressure pump cartridge to work reliably, there are several technical challenges that should be met, and the prior pump cartridges can be more complex and have tighter tolerances than would be ideal in at least some instances.

Work in relation to the present disclosure suggests that the reuse of pump cartridges may not be appropriate in at least some instances, resulting in cartridges potentially being reused in a less than ideal manner. Also, at least some of the prior approaches can require more user skill than would be ideal. Some of the prior approaches may less than ideally utilize the forces available from a pump console that receives the cartridge.

In some instances, the fluid flow from the nozzle jet used in surgery or other applications can be less than ideal. Work in relation to the present disclosure suggests that this variability can be more pronounced with lower pump rates, which may result in increased pulse to pulse variability and the resection of material being less accurate and rougher than would be ideal.

In light of the above, it would be desirable to have improved methods and apparatus for delivering fluids such as sterile fluids for surgical procedures with water jets that overcome at least some of the above limitations.

SUMMARY

In some embodiments, a pump cartridge comprises a retention structure to retain a piston for shipping and storage, in which the piston can be decoupled from the retention structure to pump fluid. In the shipping and storage configuration, the piston may be positioned with the retention structure to allow sterilization gas to travel within a housing and into a cylinder distal to the piston, in accordance with some embodiments. When placed in the console for use in a pumping configuration, the piston can be decoupled from the retention structure to form a seal within the housing. In some embodiments, when the procedure has been completed, the pump cartridge can be decoupled from the console in a manner that disables the cartridge for subsequent use to prevent a non-sterile cartridge from being reused. In some embodiments, axial force from a pushrod of the console decouple the piston from the retention structure, which can allow increased amounts of force for decoupling and increased stability of the cartridge and associated components such as the pistons in the shipping and storage configuration. The cartridge may comprise a deformable valve seat to permit looser tolerances during manufacturing and can decrease valve leakage and improve performance. In some embodiments, the cartridge comprises a plurality of pistons to provide more uniform fluid flow rates through the nozzle. In some embodiments, the cartridge is configured to couple to a high-pressure line having suitable elasticity to decrease piston pulse to piston pulse variability of a fluid stream through a nozzle.

In some embodiments a pump cartridge comprises a piston. A housing comprises a channel, an inlet, and an outlet, in which the channel comprises a cylinder shaped to receive the piston. An engagement structure is configured to couple the piston to a pushrod in response to axial movement of the pushrod or the housing.

In some embodiments, a pump console comprises a receptacle to receive a pump cartridge, and a locking structure to engage a fastener of the pump cartridge. A pushrod is configured to engage the pump cartridge, and an actuator is coupled to the pushrod. A processor is coupled to an actuator to move the pushrod, and the processor is configured to advance the pushrod into the cartridge in response to the locking structure engaging the fastener.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 42A shows a fluid pressure profile of a single piston pump operating at 20 Hz; in accordance with some embodiments;

FIG. 42B shows a fluid pressure profile of a dual piston pump operating at 20 Hz; in accordance with some embodiments;

FIG. 42C shows a fluid pressure profile of a single piston pump operating at 10 Hz; in accordance with some embodiments; and FIG. 42D shows a fluid pressure profile of a dual piston pump operating at 10 Hz; in accordance with some embodiments.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The pump consoles and cartridges as described herein can be used in many applications, such as the surgical resection of tissue, dentistry, cosmetic surgery, dermatology, ophthalmology, urology, surgical removal of tissue from organs, and industrial applications such as machining. The pump consoles and cartridges as described herein can be incorporated with many commercially available surgical systems. Although reference is made to surgical and healthcare applications, the presently disclosed pump cartridge and console will find applications in many fields, such as industrial applications including paint sprayers and the machining of parts.

The pump cartridge can be configured to generate high pressure fluid flow with relatively little leakage, allow fluid to enter the pump cylinders quickly little or no cavitation within the cylinder, high efficiency and rapid fluid expulsion from the cylinders.

Figure 1:
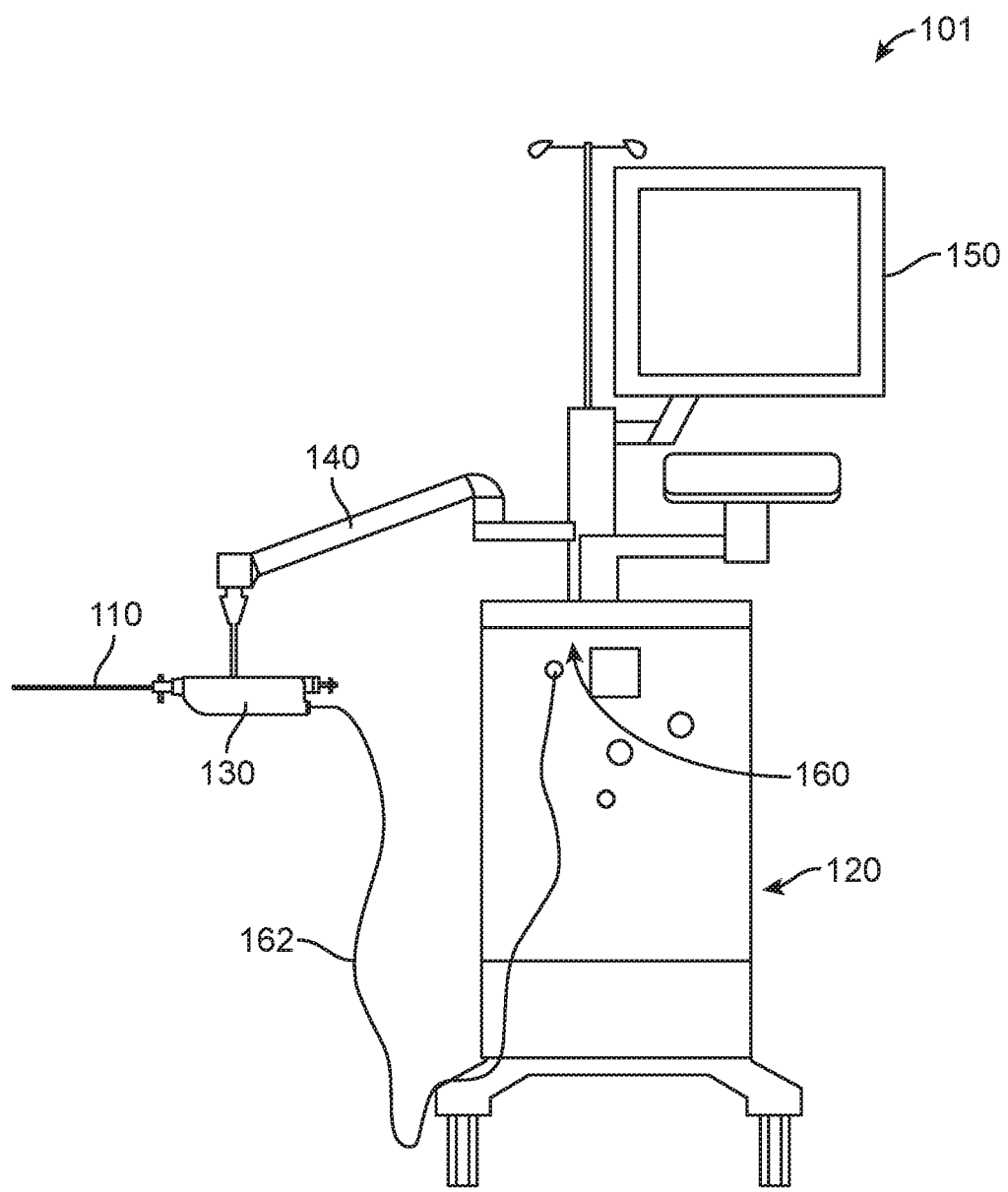
FIG. 1 shows a system that treats a patient with fluid stream energy, in accordance with some embodiments.

With reference to FIG. 1, a system that treats a patient with fluid stream energy is shown. The system 101 includes a treatment probe 110 and may optionally include an imaging probe. The treatment probe 110 may be coupled to an imaging console 120 and a base 130. The patient treatment probe 110 and the imaging probe may be coupled to a common base 130. The treatment probe 110 is coupled to the imaging console 120 with an arm 140.

In some embodiments, the system 101 includes a display 150 for allowing a technician to visualize the location and orientation of the treatment probe 110, such as when the treatment probe 110 is positioned inside a patient. The console 120 includes a pump 160 which is in fluid communication with the treatment probe 110 by one or more hoses 162. The hose 162 may comprise a high-pressure line.

The pump 160 may be any type of suitable pump for pumping fluid, such as for example, a rotary lobe pump, a progressing cavity pump, a peristaltic pump, a rotary gear pump, a piston pump, a diaphragm pump, a screw pump, or some other type of fluid pump. In some embodiments, the pump is a piston pump and may be configured to drive one, two, or more pistons. As will be described hereinafter, a dual piston pump is shown and described, but this disclosure should not be so limited as any number of pistons can be used with the inventions described herein.

The pump includes a cartridge, that in some embodiments, is removable from the pump such as for cleaning, repair, or replacement as components wear over time through normal use. The pump cartridge, in some embodiments, includes a valve body housing one or more inlet valves, outlet valves, and fluid seals.

Figure 2A:
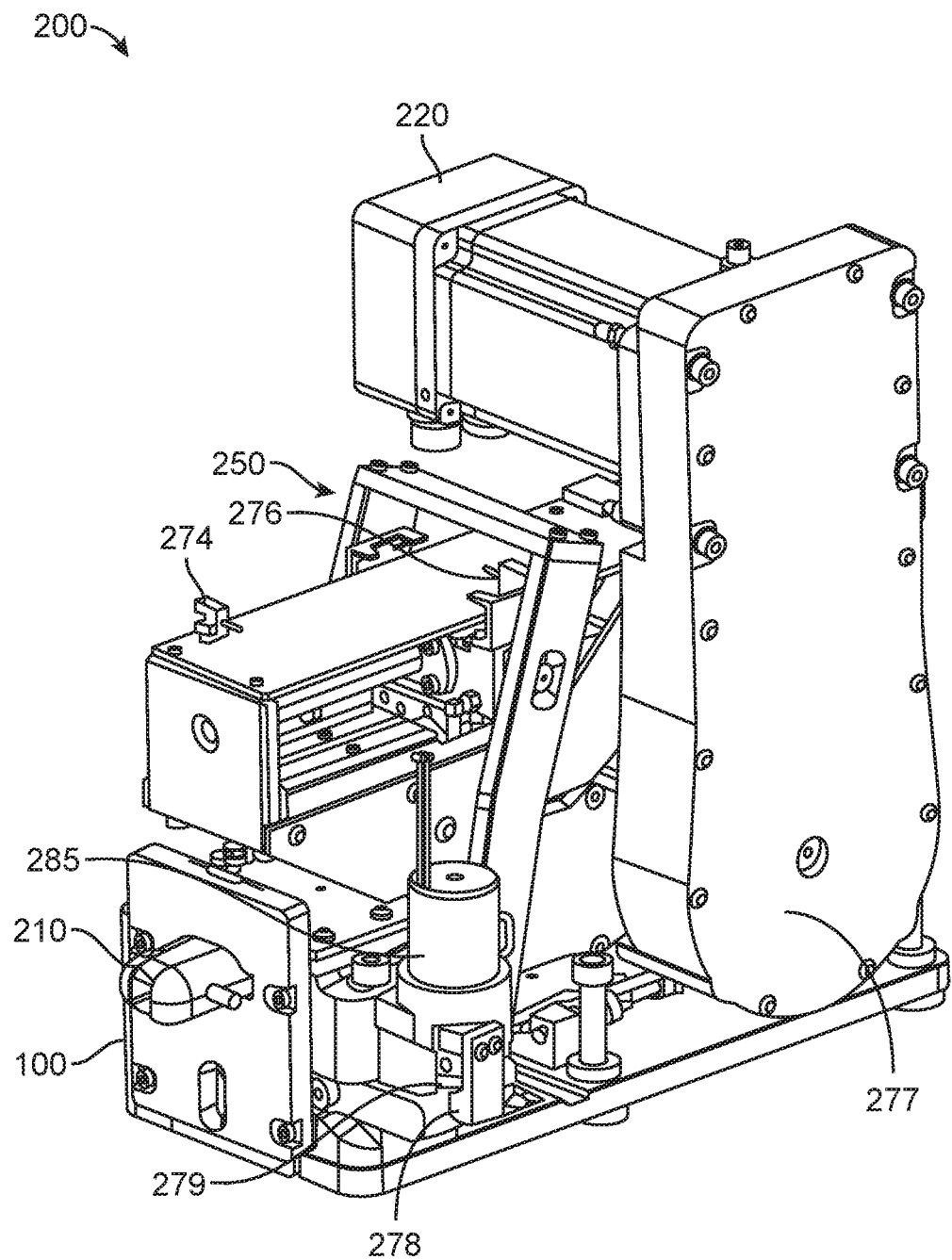
FIGS. 2A and 2B show external views of a console to receive a cartridge, in accordance with some embodiments.
Figure 2B:
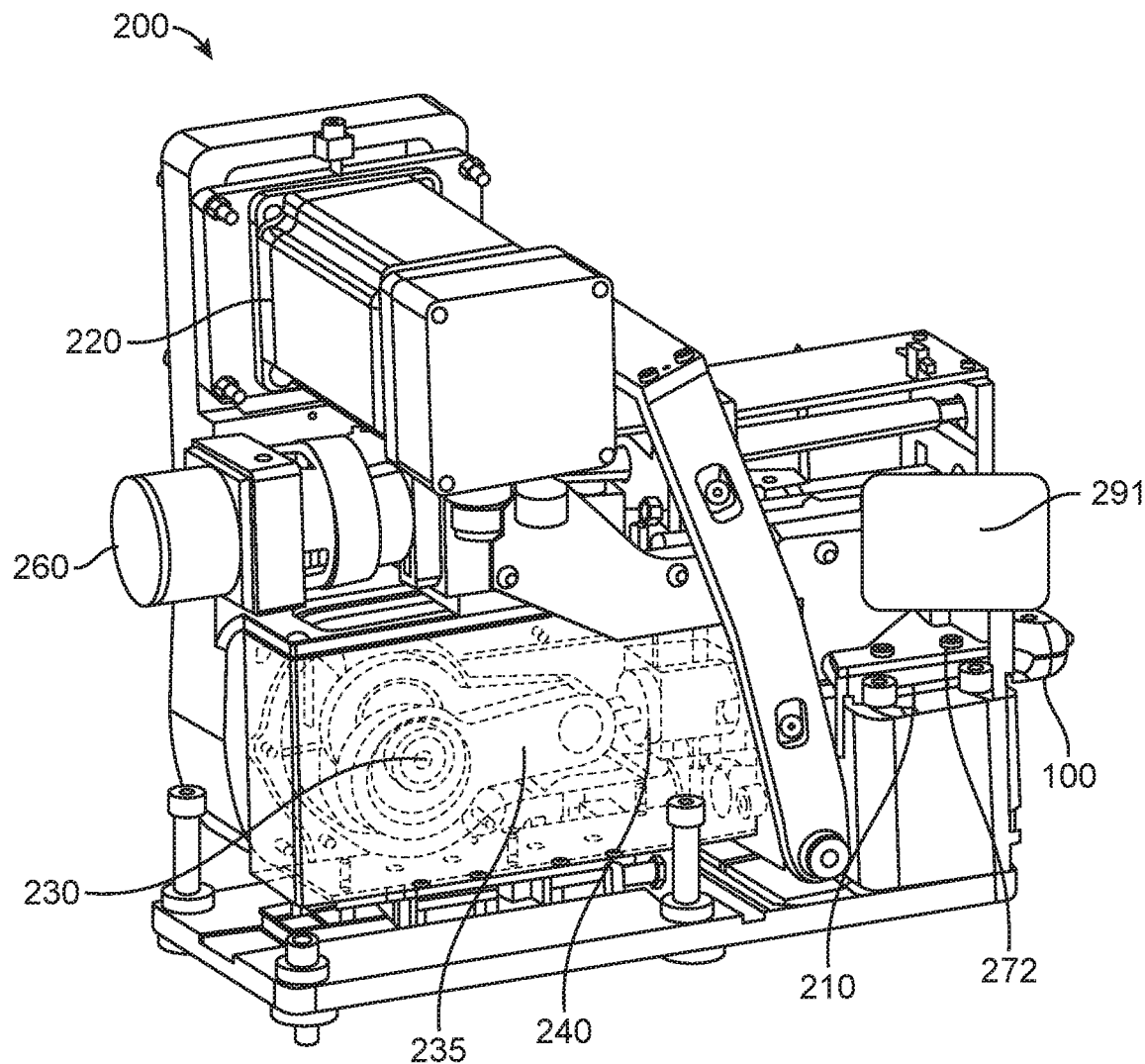
Figure 2C:
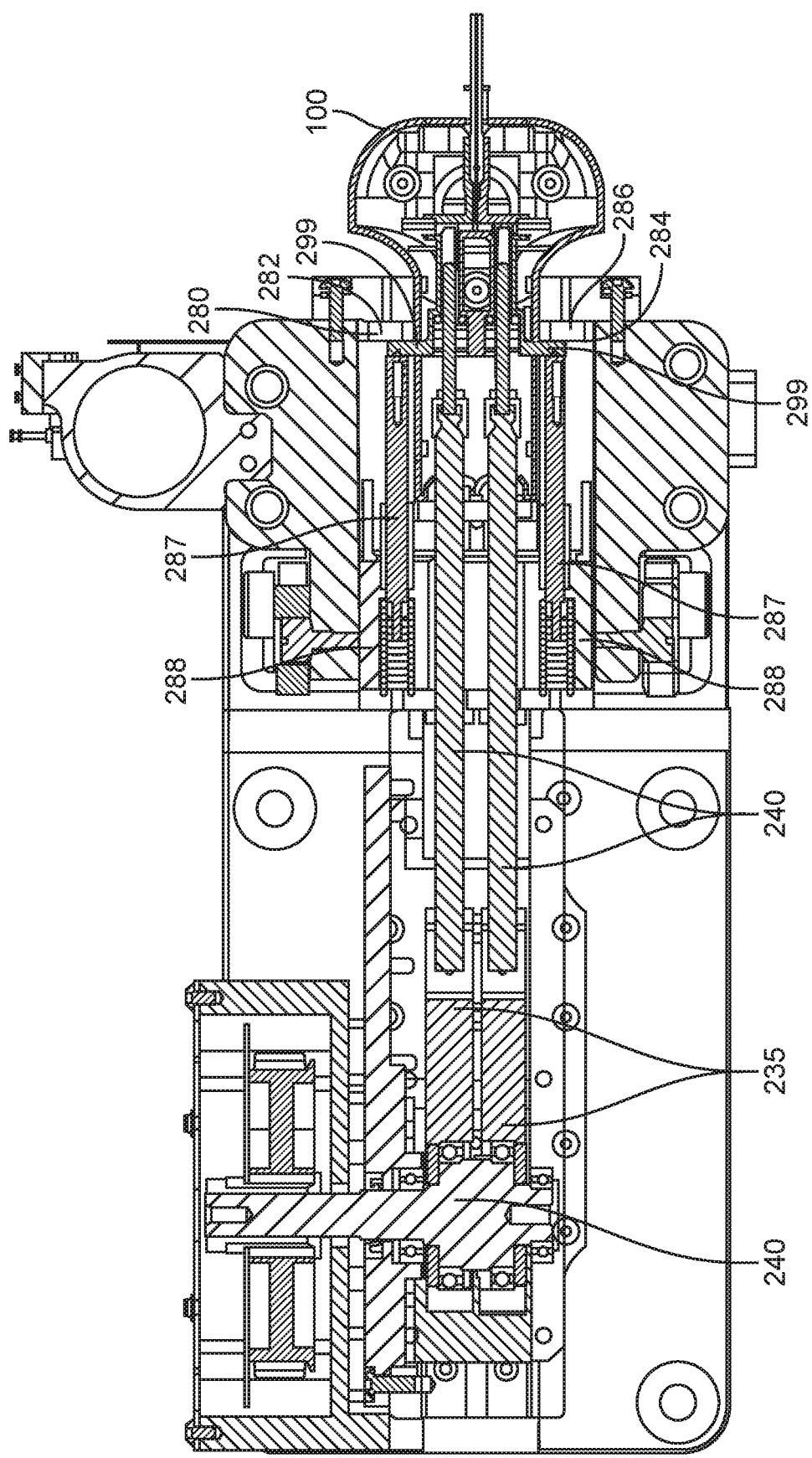
FIG. 2C shows a cross-sectional view of the console as in FIGS. 2A and 2B, in accordance with some embodiments.

FIGS. 2A and 2B show external views from different angles of a console 200 to receive a pump cartridge as described herein into system 101. FIG. 2C shows a cross-sectional view of the console 200. The console can be configured in many ways, and may comprise a stand-alone console, or can be integrated with a surgical or other system. The console comprises a cartridge receptacle 210 (also referred to herein as a loader, or a cartridge loader) sized and shaped to receive the cartridge 100. The cartridge receptacle may comprise structures to receive structures of the cartridge as described herein, in order to fasten the cartridge to the receptacle. The receptacle can be configured for linear insertion of the cartridge 100 into the receptacle 210, for example.

The console may comprise a pump motor 220 coupled to a crankshaft 230 with a transmission. Alternatively, or in combination, the transmission may comprise a crankshaft 230 and one or more connecting rods 235 coupled to one or more pushrods 240. The crankshaft 230 can be coupled to the one or more pushrods 240, e.g. a plurality of pushrods, with the connecting rods 235 positioned therebetween. The motor and transmission can be configured to drive each of the pushrods at a variable rate, for example within a range from about 25 Hz to about 300 Hz, and from a rate from about 50 Hz to about 200 Hz. The pushrods can be coupled to the pistons of cartridge 100 with engagement structures as described herein.

The console may comprise a movable component, such as an arm or clamp 250 to fasten the cartridge to the console when placed in the receptacle. The console may comprise a motor coupled to the movable component, e.g. a clamping motor 260, in order to drive the movable component to a first position to fasten the cartridge in the receptacle, and a second position to allow placement of the cartridge in the receptacle and removal of the cartridge from the receptacle.

In some embodiments, the moveable component may comprise a plate, a gate, or a retainer to engage with the cartridge when the cartridge is placed in the receptacle and fully seated. For example, the cartridge may have one or more protrusions, and once the cartridge is seated within the receptacle, the moveable component can engage with the one or more protrusions to maintain the cartridge in an installed configuration. In the installed configuration, the connecting rods 240 of the console can engage with the pushrods of the cartridge.

The console may comprise a plurality of sensors. The console may comprise a sensor 272 to detect placement of the cartridge in the receptacle 210. The console may comprise a sensor 274 to sense the movable component fastening the cartridge in the receptacle and may comprise a clamped sensor to detect the movable component clamping the cartridge in place. The plurality of sensors may comprise a home sensor 276 to detect the movable clamp component moving to a home or resting position. The plurality of sensors may comprise a sensor to sense an intermediate position in the cylinder, for example a mid-dead-center sensor 277 to indicate a mid-dead-center position of a piston in the cylinder, which is half way between a top dead center position and a bottom dead center position. The plurality of sensors may comprise a first gate sensor 278 to detect an open configuration of the gate and a second gate sensor 279 to detect a closed configuration of the gate. The plurality of sensors may comprise a crankshaft position sensor 281. The crankshaft position sensor 281 may comprise an optical sensor and may be used to verify that the pushrods are in the middle dead center, such as for loading the cartridge and coupling the pushrods with the pistons of the cartridge.

The console may comprise a sensor 291 to read a unique identifier of the cartridge. The unique identifier may comprise one or more of a QR code, a bar code, an RFID, or some other indicia, and the reader may comprise one or more of a QR code reader, bar code scanner or an RFID reader. The sensor can be coupled to a processor configured to read the unique identifier from the cartridge. The processor can be configured with instructions to determine if the cartridge is a valid cartridge. The processor may comprise a library of valid unique identifiers or be operatively coupled to a library of valid unique identifiers. The processor can be configured to allow a treatment to proceed in response to the unique identifier of the cartridge matching the unique identifier in the library. The library may comprise unique identifiers of previously used cartridges, and the processor configured with instructions not to proceed with treatment in response to the unique identifier of the cartridge comprising an identifier corresponding to a used cartridge.

Referring again to FIG. 2C, the console may comprise a gate 280 to retain cartridge 100 in position for pumping when the gate is closed. The gate can be moved to an open position to allow insertion and removal of the cartridge 100. The gate 280 can be sized and shaped in many ways and may comprise a "U" or forked shape structure to engage the fastener of the cartridge 100 as described herein. The console may comprise a guide such as a slot 282 along which gate 280 slides into a locking position to secure the cartridge 100. In some embodiments, a second slot 284 is located on a second side of cartridge 100. The gate may comprise a second extension 286 to slide in second slot 284 to engage an opposing fastener of cartridge 100 as described herein. The gate may be coupled to an actuator, such as a solenoid 285 to move the gate between open and closed positions.

The solenoid 285 may actuate in response to one or more parameters associated with the cartridge. For example, the solenoid 285 may actuate and move the gate to a closed position upon a limit switch being activate as the cartridge is fully inserted into the receptacle. The solenoid 285 may actuate and move the gate to a closed position upon a sensor reading a code on the cartridge. The code, which may be a QR code or some other indicia, may identify data associated with the cartridge, and may only be read once the cartridge is properly inserted into the receptacle. Similarly, the solenoid 285 may be actuated automatically upon completion of a treatment cycle. Alternatively, the solenoid 285 may be manually actuated, such as by pressing a switch or button.

The console may comprise a plurality of movable members such as pins 287 coupled to a plurality of springs 288. Once the cartridge has been placed and the gate is in position in the closed configuration, the movable members press against a plurality of fasteners 299 of the cartridge 100, which may comprise a fastener comprising a portion of the metallic housing as described herein. The movable members, e.g. pins 287, can press the fasteners 299 against the gate 280 in order to secure the cartridge for advancement of pushrods into an engagement structure as described herein.

Figure 2D:
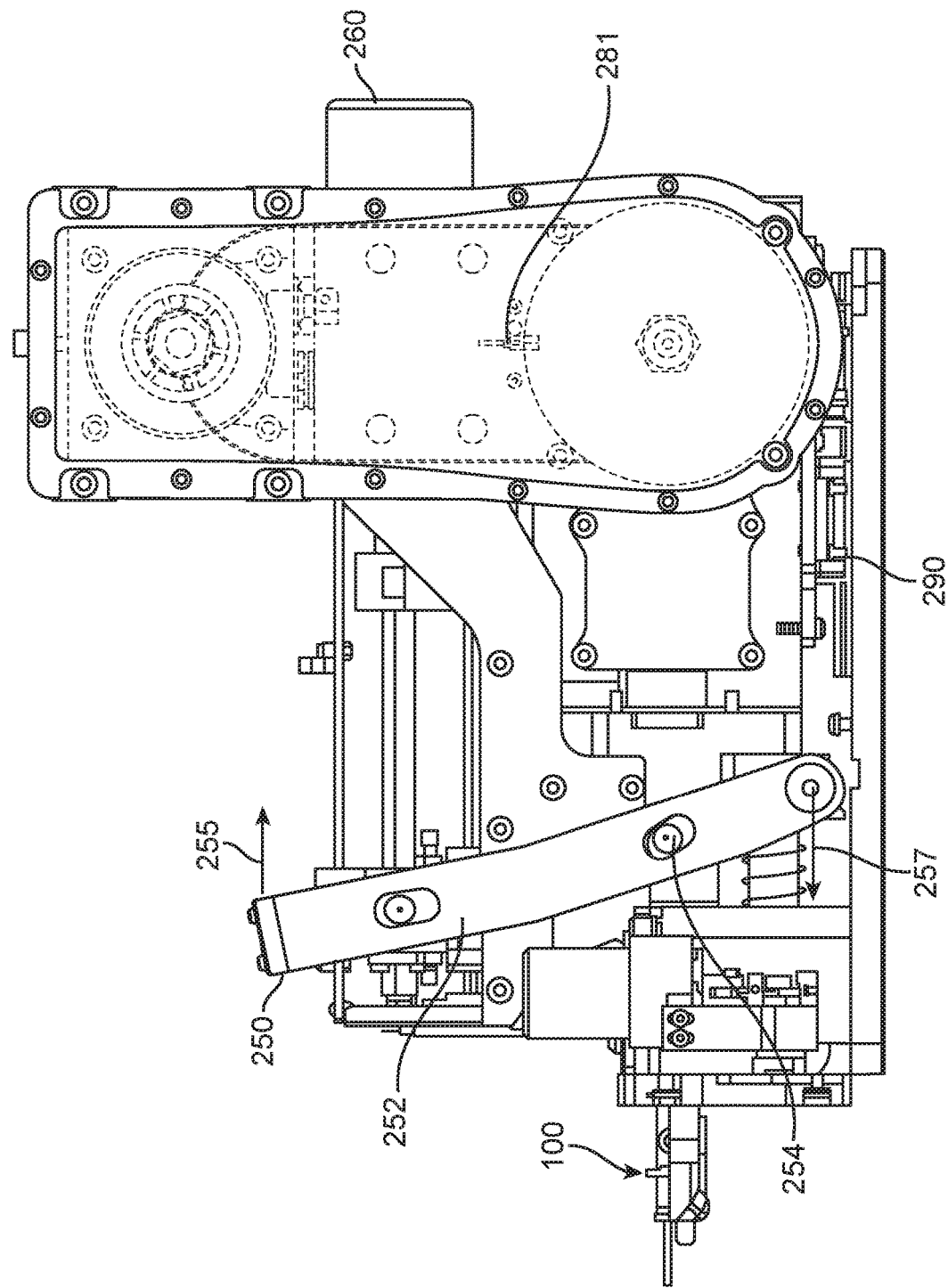
FIG. 2D shows a side view of the console as in FIGS. 2A to 2C in an unclamped configuration, in accordance with some embodiments.

FIG. 2D shows a side view of the console as in FIGS. 2A to 2C in an unclamped configuration. The clamp 250 comprises an arm and is shown in a first configuration, in which the motor, transmission, coupling rods, and pushrods are located away from the cartridge 100. With advancement of the clamp 250 toward a second configuration in a direction indicated by arrow 255, the pump motor 220 and transmission comprising crankshaft 230, connecting rods 235 and pushrods 240 are advanced toward cartridge 100 in a direction indicated by arrow 257. The clamp arm can be advanced with rotation of clamping motor 260. The clamp 250 can be coupled to clamping motor 260 in many ways, for example with a threaded nut to move the clamp arm with rotation of clamping motor 260. The pump motor 220 and transmission comprising the crankshaft 230, connecting rods 235 and pushrods 240 can be supported on a carriage 290 to allow translation of these components toward cartridge 100 as described herein. The carriage 290 may comprise rails and sliders to allow the pump motor, transmission comprising the crankshaft, coupling rods and pushrods to translate between the clamped and unclamped positions. The clamp 250 may comprise an arm 252 that generally pivots about a pivot point 254 to advance the carriage and associated component toward cartridge 100.

Figure 2E:
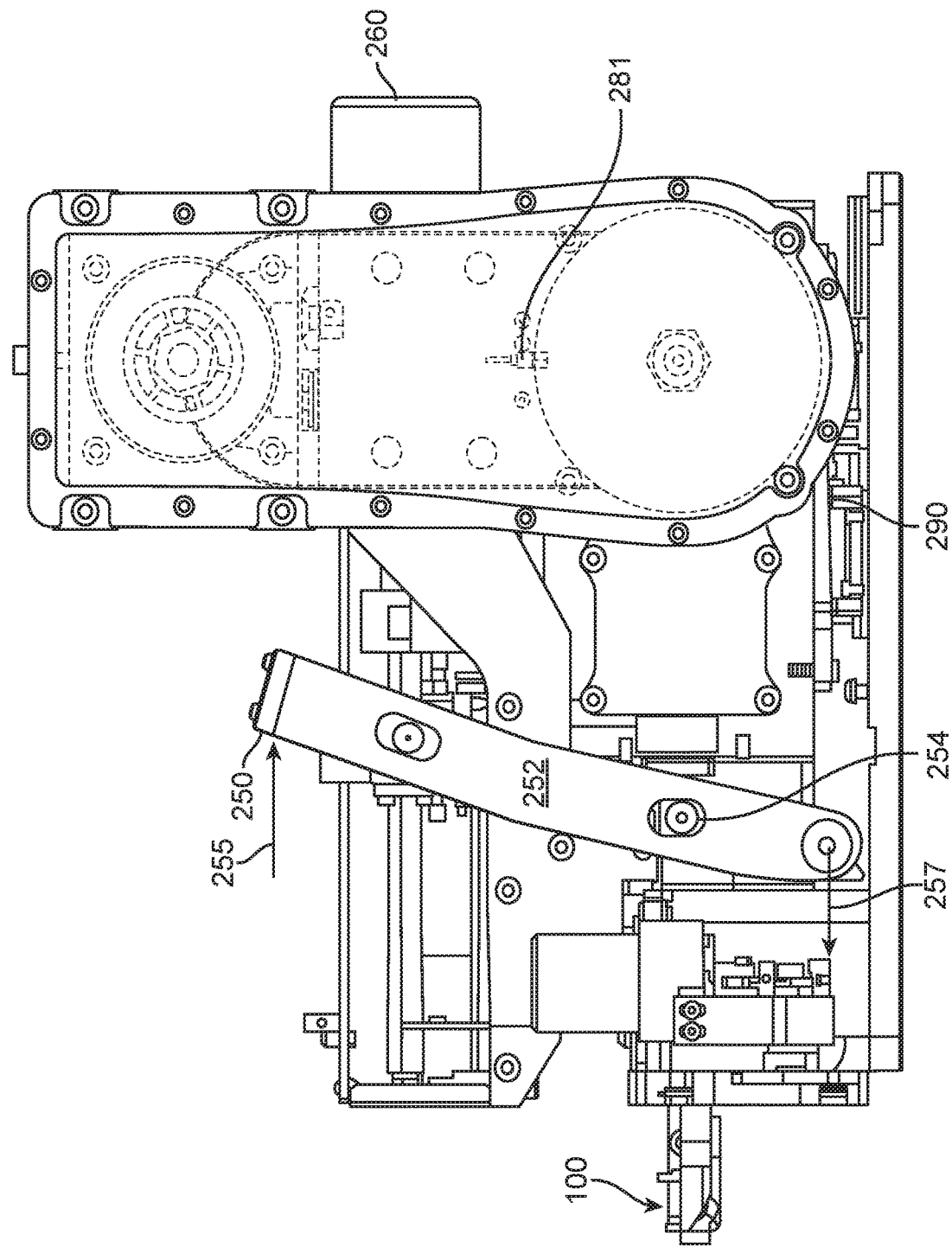
FIG. 2E shows a side view of the console as in FIGS. 2A to 2C in a clamped configuration, in accordance with some embodiments.

FIG. 2E shows a side view of the console as in FIGS. 2A to 2C in a clamped configuration, in which the components supported on carriage 290 have been advanced in a direction indicated by arrow 257 so as to engage the cartridge 100 with the pushrods.

In some embodiments, the pushrods are positioned in an intermediate position between top dead center and bottom dead center (e.g. middle dead center) when the pushrods are advanced into the engagement structures and further advanced to break the pistons and engagement structures away from the retention structures as disclosed herein.

Figure 2F:
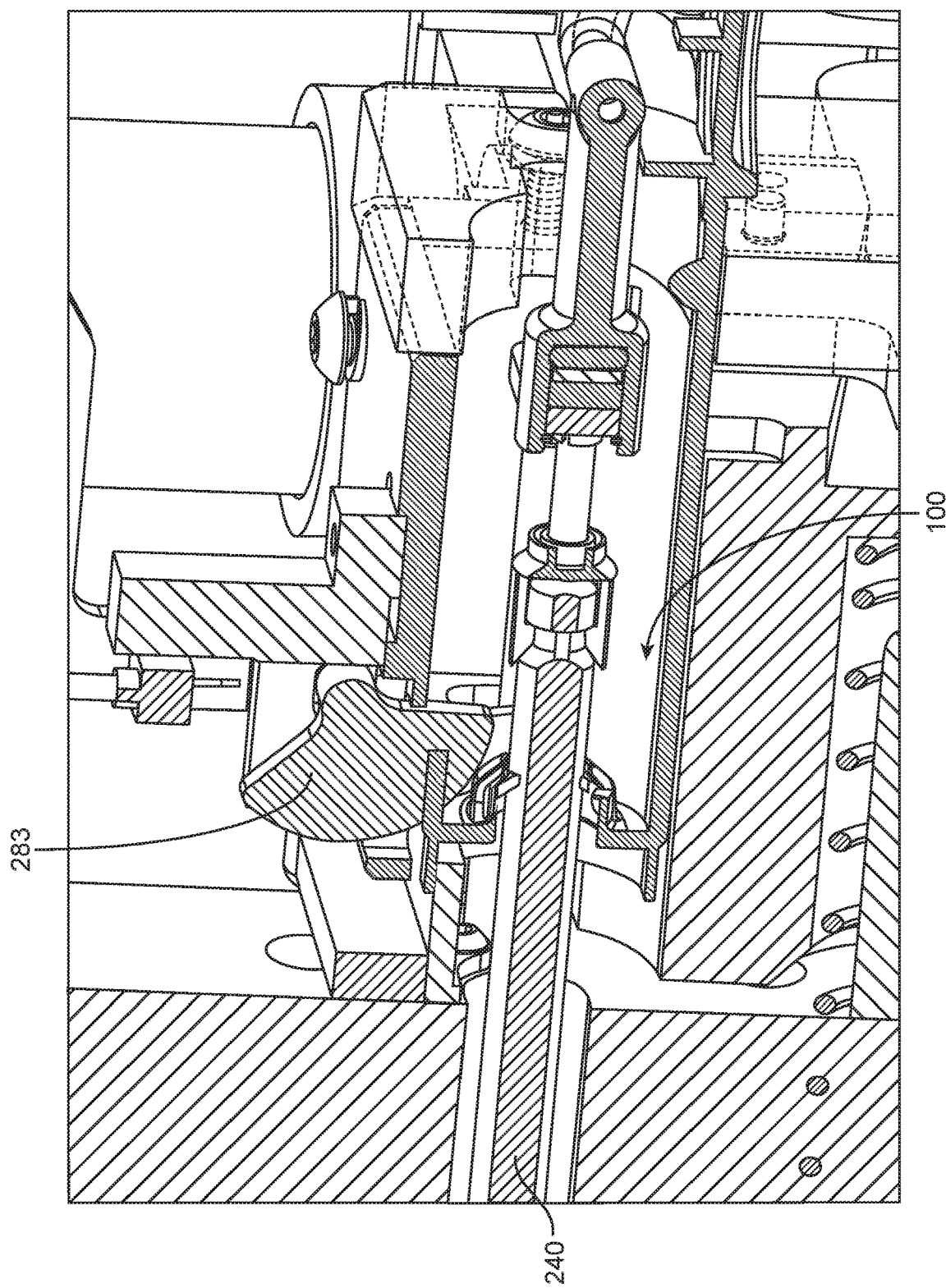
FIG. 2F shows a partial cutaway view of the console as in FIGS. 2A to 2C, in accordance with some embodiments.

FIG. 2F shows a partial cutaway view of the console as in FIGS. 2A to 2E and shows a pushrod 240 coupled to a piston of a cartridge as will be described hereinbelow. A position sensor 283 can be used to detect the presence and the proper position of a cartridge 100. The position sensor 283 may be used to trigger the closing of the gate to secure the cartridge 100 in an installed configuration. The gate may be moved by any suitable mechanism, such as a motor, a solenoid, or manual positioning by an operator. In some embodiments, the cartridge 100 moves the position sensor 283 as it is inserted into the receptacle, which may trigger a switch that causes a gate, or some other retaining structure, to capture the cartridge in the installed configuration and hold the cartridge against the pumping force imparted by the control rods.

A processor can be coupled to one or more of each of the console sensors as disclosed herein to provide movement of the components of the console in response to readings from the sensors.

In some embodiments, the processor is configured to advance the pushrods into the cartridge a first distance to decouple one or more pistons of the cartridge from a retentions structure of the piston. The retentions structure may secure the pistons in a secure position, such as for shipping or storage. Once engaged by the pushrods, further advancement of the pushrods can liberate the pistons from the retention structures. In some cases, the pistons are liberated by breaking the retentions structures, or by forcing the pistons to disengage with an interfering portion of the retention structures or the valve case in order to move in a reciprocating motion. The pushrods are configured to advance to a top dead center and withdraw to a bottom dead center as they reciprocate by action of the motor.

In use, an operator inserts a cartridge into the receptacle. Once the cartridge is inserted fully, a sensor detects that the cartridge is inserted and a sensor can read the unique identifier indicated on the cartridge. A retaining structure, such as a plate or gate, may be actuated to slide into place and inhibit the cartridge from being removed from the receptacle. The pump motor 220 and transmission comprising crankshaft 230, connecting rods 235 and pushrods 240 are advanced toward cartridge 100. The pushrods coupled to the connecting rods of the motor engage the pistons of the cartridge. Further advancement of the pushrods liberates the pistons from their respective retention structures and the piston can then reciprocate in response to rotational operation of the motor.

Advancement of the pump motor and transmission may be performed by a lead screw in response to rotation of the clamping motor 260. The clamping motor 260 may be operated under control of the processor and in response to the processor determining, based on signals from one or more sensors, that the cartridge is a correct cartridge and the cartridge has been fully inserted into the receptacle.

Figure 2G:
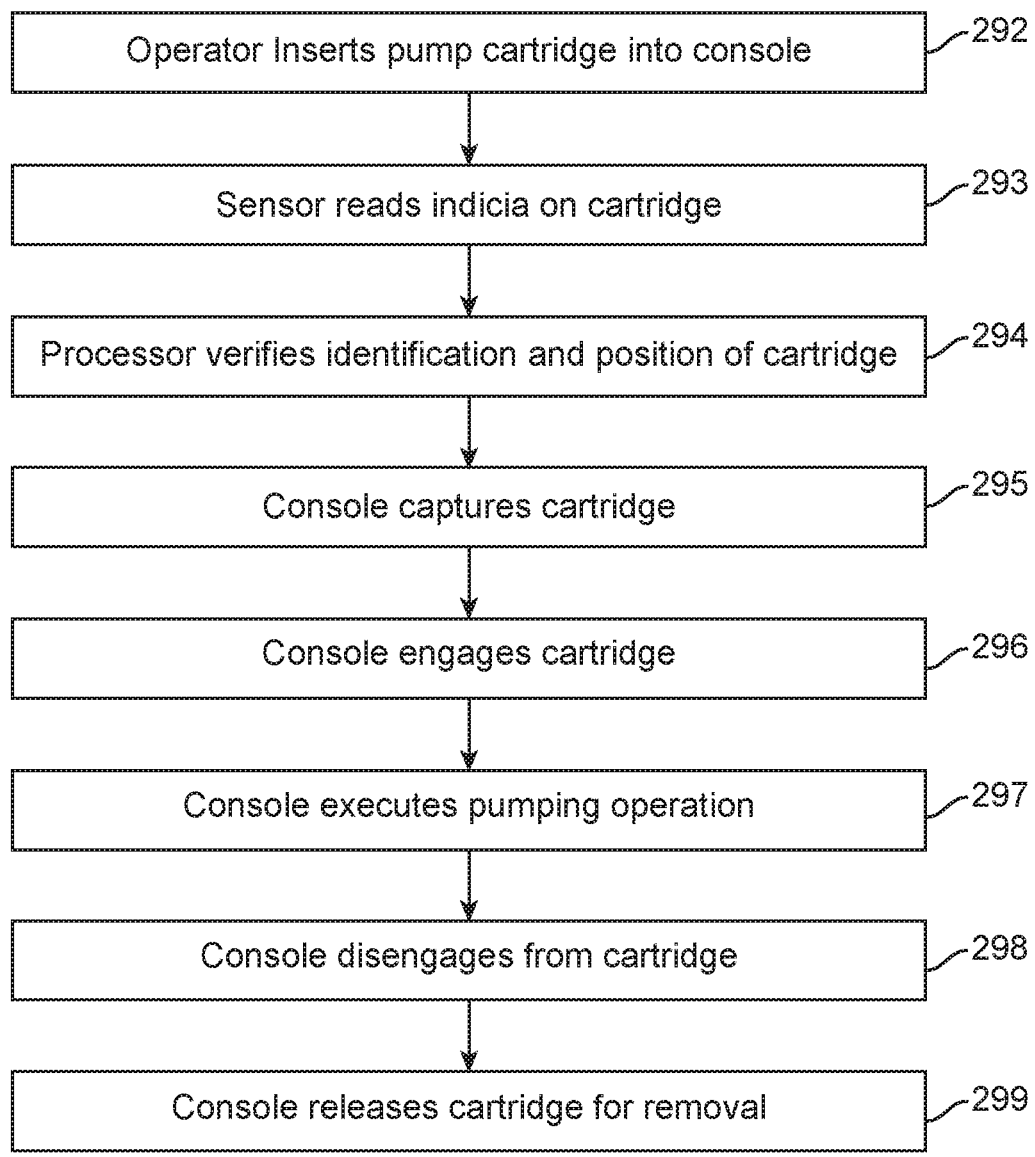
FIG. 2G shows a process flow diagram for loading a cartridge, performing a pumping operation, and unloading a cartridge, in accordance with some embodiments.

With reference to FIG. 2G, a process flow diagram for loading a cartridge, performing a pumping operation, and unloading a cartridge is shown.

At step 292, an operator inserts a pump cartridge into the console, such as by inserting the cartridge into the receptacle of the console.

At a step 293, a sensor reads an indicia on the cartridge. The sensor may comprise any suitable sensor such as a bar code scanner, an RFID scanner, or a QR code scanner, e.g. a camera.

In some embodiments, a second sensor is used to determine the position of the cartridge for capture. The second sensor is configured to generate a signal indicating that the cartridge has been placed at the location for capture, and the processor receives the second sensor signal as input to capture the cartridge with the gate when the cartridge has been placed at the capture location. The second sensor may comprise any suitable sensor such as a proximity sensor, a switch or a Hall effect sensor, for example.

At step 294, a processor associated with the console identifies the cartridge and the position of the cartridge. This may be performed through any suitable sensor type, such as a limit switch, an optical sensor, a position sensor, or otherwise. The processor may utilize a sensor to determine indicia on the cartridge that may provide data associated with the cartridge such as the type of cartridge, the date of manufacture of the cartridge, material properties of the cartridge, or otherwise. In some embodiments, an optical sensor can be used to both read the indicia and determine the position of the cartridge.

At step 295, the console captures the cartridge. This may be performed automatically in response to the processor determining that the cartridge is of a proper type and/or has been inserted properly into the console. The cartridge may be captured through any suitable structure as has been describe herein. In some instances, a gate moves into a position that interferes with removal of the cartridge. The gate may be actuated by a motor, a solenoid, or some other structure.

At step 296 the console engages the cartridge as described herein. In some embodiments, a clamping motor turns a lead screw which causes the transmission comprising the crankshaft 230, connecting rods 235 and pushrods 240 to slide forward toward the cartridge. The pushrods 240 then couple to the pistons of the cartridge and rotation of the motor turns the crankshaft, which causes reciprocation of the connecting rods, the pushrods, and the pistons.

At step 297, the console, under control of the processor, executes a pumping operation. The pumping operation comprises a speed and duration of activating the motor. A desired speed of the motor translates into a desired fluid pressure exiting the cartridge.

At step 298, the console, under control of the processor, stops the pumping cycle and disengages from the cartridge. The disengagement may be performed by reversing the steps that cause the console to engage with the cartridge. For example, the console may activate the clamping motor in a reverse direction, which causes the transmission to withdraw from the cartridge and the pushrods may disconnect from the pistons.

At step 299, the console releases the cartridge, such as by activating a solenoid or motor to open the gate, thereby allowing the cartridge to be removed from the console.

According to some embodiments, the cartridge may be electrically isolated from the source of power to the console. For example, the cartridge may have one or more components coupled thereto that are non-conductive. In some embodiments, one or more of the sensors are mounted to non-conductive materials, such as plastic. In embodiments in which one or more components of the cartridge are metal, the components that interact with the cartridge may each be electrically isolated. For example, protrusions on the cartridge used for capturing the cartridge within the console are metal in some embodiments. Accordingly, the gate, the pushrods, and the crankshaft may all be isolated from the source of electrical power to the console to avoid creating an electrical ground path through the cartridge.

Figure 3:
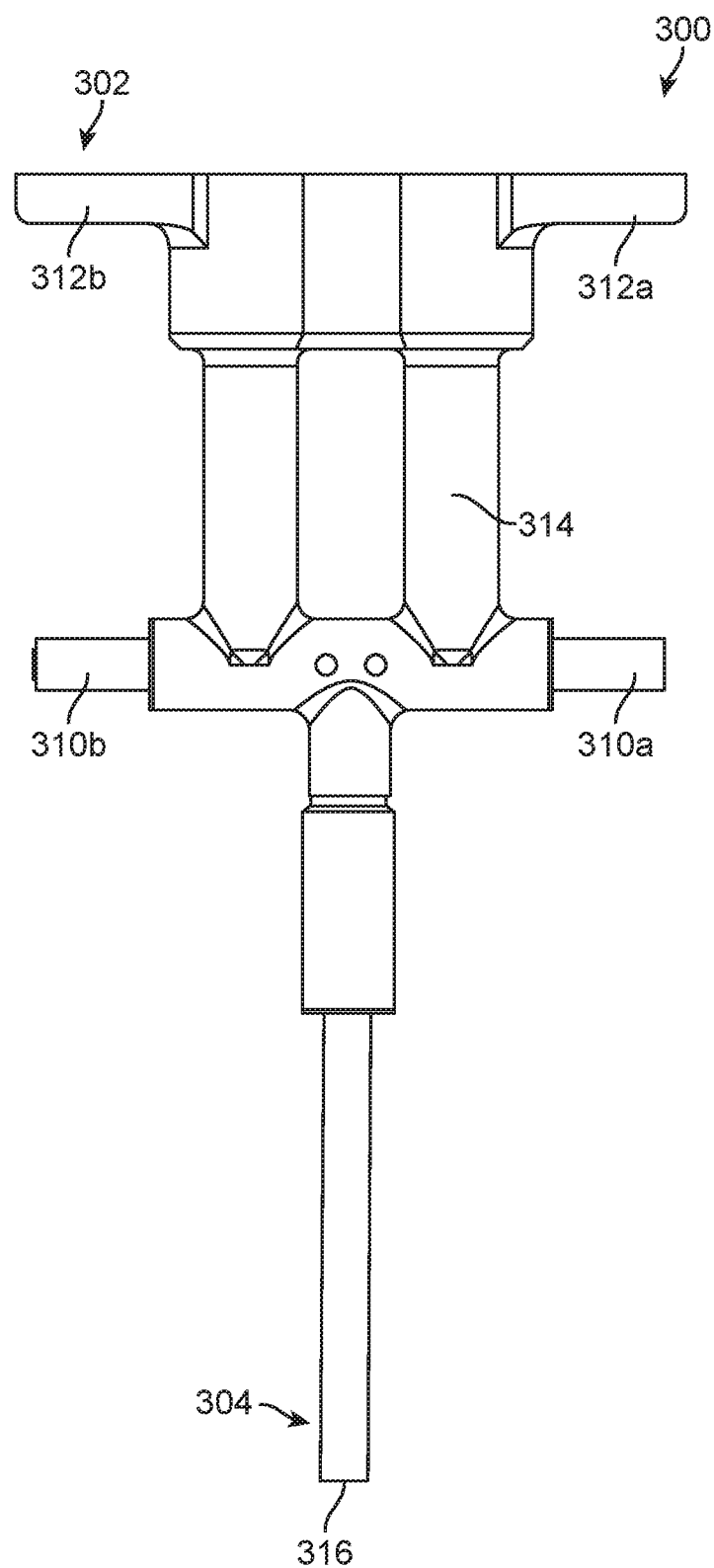
FIG. 3 shows a valve body usable with a fluid pump in accordance with some embodiments.

With reference to FIG. 3, the cartridge 100 may comprise components for pumping a fluid such as a liquid when coupled to the pushrods. The pump cartridge 100 may comprise a housing that comprises one or more components of a valve body 300. Valve body 300 includes a proximal end 302 and a distal end 304. The distal end 304 corresponds with a fluid outlet 316 and is configured for coupling with a delivery hose for delivering pressurized fluid to a nozzle, such as a nozzle of a treatment probe. The valve body may comprise a housing shaped with fluid inlets and an outlet for the delivery of pressurized fluid such as a liquid. The housing of valve body 300 may comprise one or more cylinders sized and shaped to receive pistons of cartridge 100 as described herein.

The valve body 300 includes fluid inlets 310a, 310b for coupling to a fluid source and providing one or more fluid inlets to the interior of the valve body 300. In some instances, the fluid inlets 310a, 310b, are ports that provide fluid communication between the inside of the valve body 300 and ambient fluid outside the valve body 300. For instance, a plenum may surround portions of the valve body 300 and provide a reservoir of fluid that may be drawn into the valve body 300 through the fluid inlets 310a, 310b. The fluid inlets 310a, 310b may alternatively be connected to fluid delivery hoses that supply working fluid to the valve body 300.

The valve body 300 may include one or more coupling flanges 312a, 312b that facilitate the valve body 300 being secured within a pump cartridge. For example, the coupling flanges 312a, 312b may include through holes that accommodate a threaded fastener that passes therethrough to securely affix the valve body 300 to a pump cartridge. Of course, other methods of securing the valve body 300 to a pump cartridge are contemplated herein.

The valve body 300 includes a plurality of valves, seals, piston sleeves, and elements for positioning, holding, and attaching the valve body to fluid paths, as will be further described hereinafter. The valve body 300 may be formed of any suitable material, such as any of a number of durable plastics, metals, or composite materials, or combinations of materials. In some embodiments, portions of the valve body are formed of steel, such as stainless steel, and more particularly, Stainless Steel 17-4, which exhibits high corrosion resistance, good formability, strength, precision, and reliability. Of course, other suitable materials, including other metals or steels can be used to form portions of the valve body 300.

As illustrated, the valve body 300 may define one or more cavities 314 for housing pistons internally thereto. The cavities 314 may define sleeves for pistons to ride in as will be discussed hereinafter.

Fluid Inlet and Outlet

Figure 4:
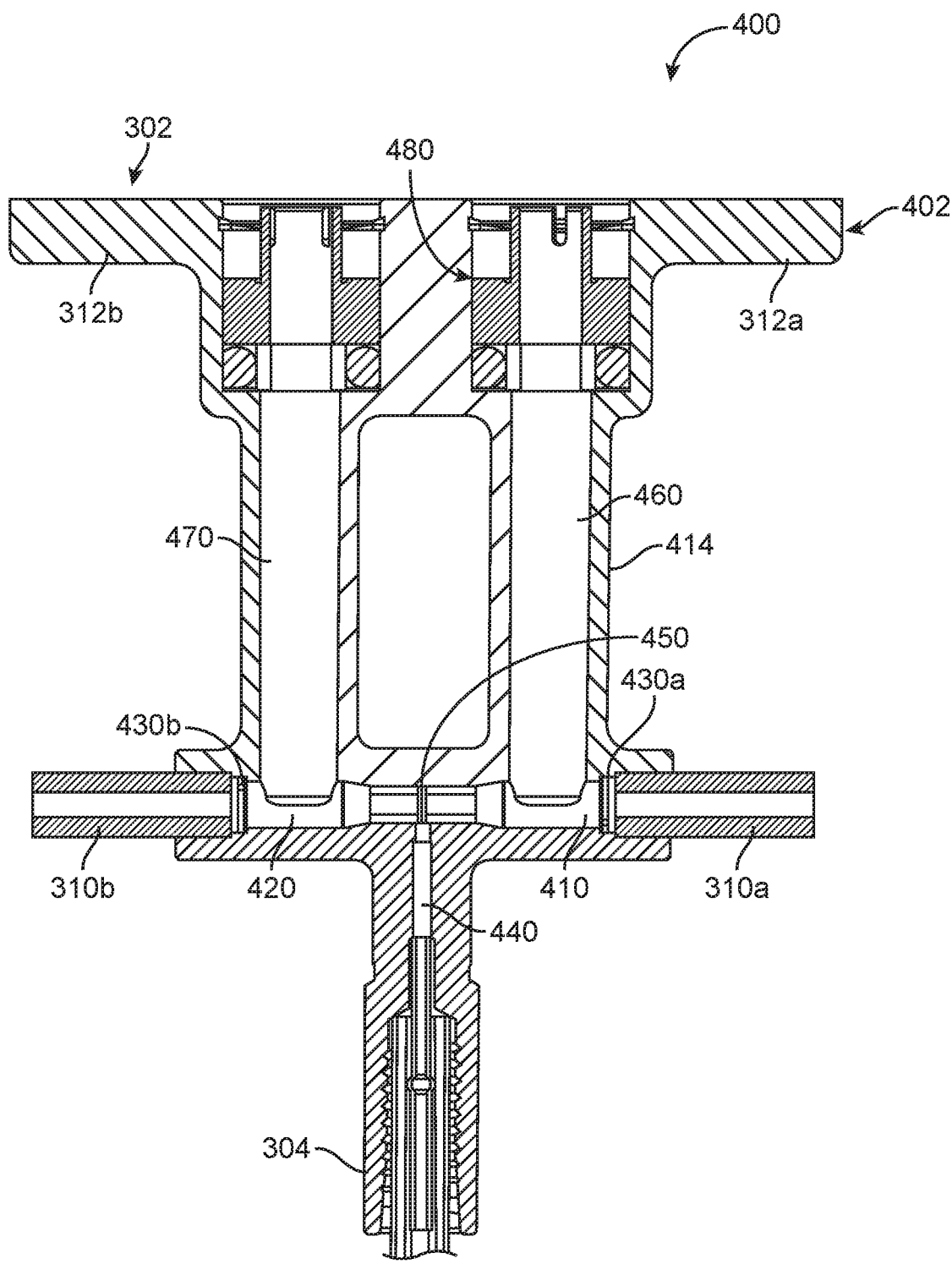
FIG. 4 shows a schematic diagram of a valve body usable in a pump cartridge having a single output valve and two valve seats in accordance with some embodiments.

FIG. 4 illustrates embodiments of a valve body 400 having a single output valve and two valve seats on the output valve. As described previously, the valve body 400 includes a housing 402 which defines a proximal end 302 and a distal end 304 and has one, two, or more fluid inlets 310a, 310b. The fluid inlet 310a is in fluid communication with a first fluid chamber 410, and the fluid inlet 310b is in fluid communication with a second fluid chamber 420. The fluid inlet 310 is separated from the first fluid chamber 410 by an inlet valve 430a that selectively allows fluid to enter the first fluid chamber 410 through the fluid inlet 310a. Similarly, an inlet valve 430b selectively allows fluid to enter the second fluid chamber 420 through the fluid inlet 310b. The inlet valves 430a, 430b can be any suitable unidirectional fluid valves, such as, for example, ball valves, flapper valves, diaphragm valves, check valves, gate valves, pinch valves, knife valves, disc valves, clapper valves, duckbill valves, leaf valves, umbrella valves, dome valves, cross-slit valves, or any other suitable valve configuration.

The first fluid chamber 410 and second fluid chamber 420 are selectively in fluid communication with fluid outlet 440 that delivers fluid to the distal end 304 and a fluid hose attached thereto, such as for delivering fluid to a treatment probe. The first fluid chamber 410 and second fluid chamber 420 are separated by an output valve 450 that selectively allows either the first fluid chamber 410 or the second fluid chamber 420 to be in fluid communication with the fluid outlet 440. According to some embodiments, the output valve 450 is a shuttle valve in which a fluid blocking element moves freely between two valve seats. When the fluid blocking element is in a first position against a first valve seat, the first fluid chamber 410 is in fluid communication with the fluid outlet 440. Similarly, when the fluid blocking element is in a second position against a second valve seat, the second fluid chamber 420 is in fluid communication with the fluid outlet 440. The fluid blocking element may shuttle between the first valve seat and the second valve seat by fluid pressure, allowing fluid to flow therethrough from one of two sources, but prevent backflow from one source to the other.

Fluid pressure within the first fluid chamber 410 and the second fluid chamber 420 can be affected by reciprocating pistons slidably disposed within cylinders 460, 470. For example, when piston located within cylinder 460 moves distally from a first, retracted position, to a second, extended position, the fluid within the first fluid chamber 410 increases in pressure, thus causing the output valve 450 to allow the fluid from within the first fluid chamber 410 to flow therethrough and to the fluid outlet 440. Concurrently, the second fluid chamber 420 fills with fluid as the piston within cylinder 470 moves proximally from an extended position to a retracted position. Thus, the fluid pressure of the opposing fluid chamber causes the output valve 450 to shuttle causing the filling chamber to be isolated while the pressurizing chamber delivers fluid to the fluid outlet 440.

The efficiency of such a configuration is influenced by the shuttling stroke of the output valve 450, with a shorter stroke providing more efficient pumping in terms of volume and pressure. In some instances, the output valve 450 is designed to maintain efficiency in fluid flow and inhibit pressure drops across the valve. This may be done, for example, by selecting a shuttle having a low mass and large cross section. In this way, the output valve 450 can be selected to minimally impact fluid volume and pressure.

The pistons are carried within a sleeve or cylinder 460, 470 defined by the housing 402. In some cases, the housing 402 has channels 414 formed therein configured to guide a piston and thus integrally form the cylinder 460, 470. In some embodiments, the channel 414 may carry a sleeve configured to guide the piston therein. While the description refers to a cylinder slidably disposed within a sleeve or cylinder 460, 470, the description should not be used to impute any specific cross-sectional geometry to the pistons or the cylinders 460, 470. For instance, while a cross section of the cylinders 460, 470 may be circular, it could likewise alternatively be formed as hexagonal, octagonal, or some other geometric shape. Similarly, the pistons that are slidable disposed within cylinders 460, 470 may be configured with a similar, or the same, cross sectional shape as the cylinders 460, 470. In some embodiments, the pistons and the cylinders 460, 470 have the same cross-sectional shape and the pistons are sized to provide a clearance between an outer surface of the piston and an inner surface of the cylinder 460, 470 to accommodate the piston sliding therein.

The channel 414 may be in fluid communication with the first fluid chamber 410 and has one or more seals to inhibit fluid leaking out of the housing 402. There are a multitude of different configurations that provide for a fluid tight seal, some of which will be discussed hereinafter. Suffice it to say, any structure or configuration that provides a fluid tight seal of the housing can suitably be implemented within the embodiments described herein.

Figure 5:
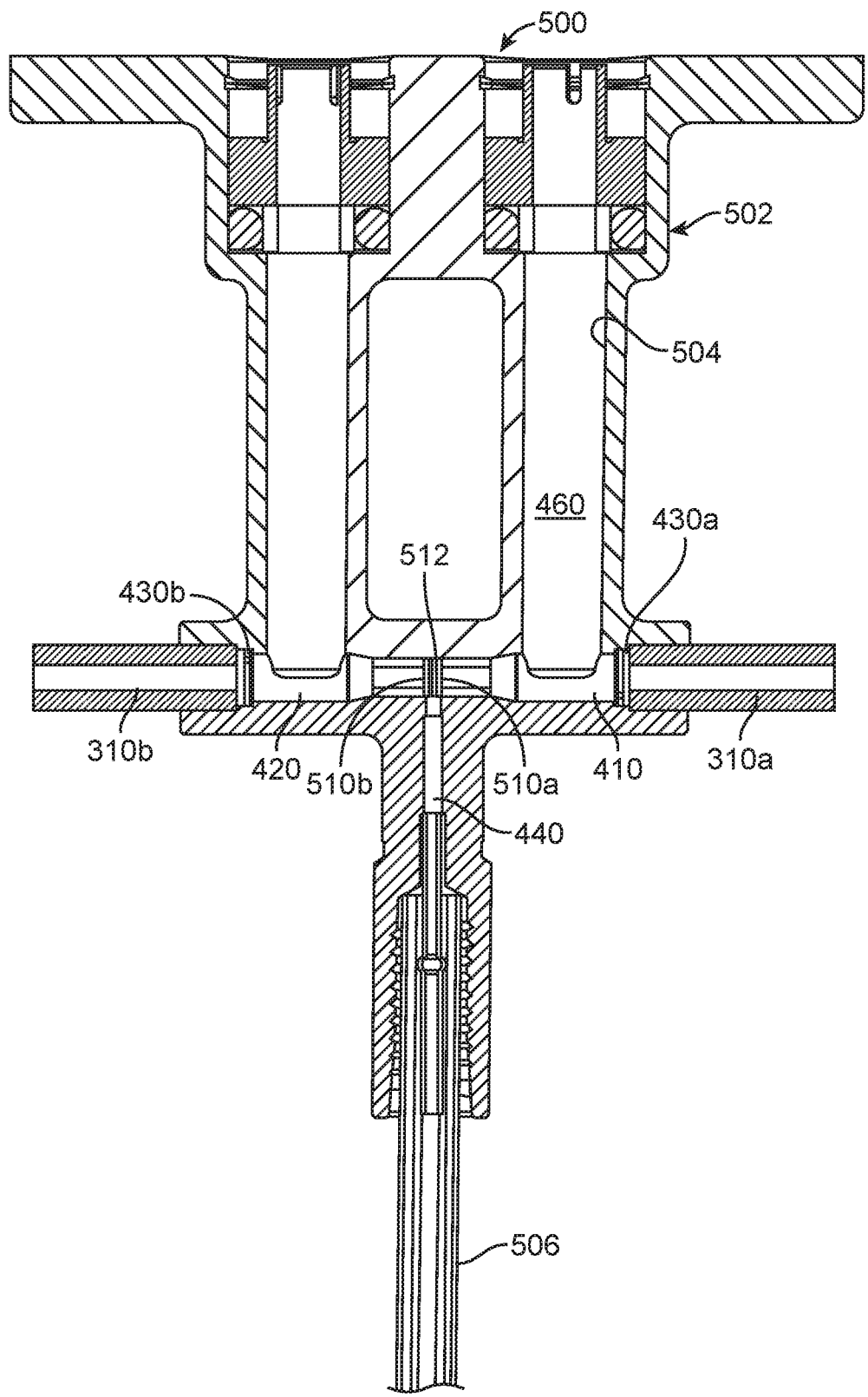
FIG. 5 shows a schematic diagram of a valve body usable in a pump cartridge having dual output valves in accordance with some embodiments.

With reference to FIG. 5, a valve body 500 has a housing 502 that defines one or more channels 504 within which ride a piston (not shown). The valve body 500 includes one or more fluid inlets 310a, 310b separated from one or more fluid chambers 410, 420 by an inlet valve 430a, 430b. While two fluid inlets and two fluid chambers are illustrated, it should be appreciated that fewer or more fluid inlets and fluid chambers may be provided. In some embodiments, each fluid chamber may have more than one fluid inlet. For example, a fluid chamber 410 may communicate with a fluid source through two, three, or more fluid inlets 310a in order to provide sufficient fluid within the fluid chamber 410 for efficient pumping operation.

In some embodiments, the inlet valve 430 is a one-way valve that is operated by fluid pressure. In these embodiments, the hydrodynamics of the pistons moving within the cylinders causes fluid to enter the fluid chamber 410 via the fluid inlet 310a, and likewise causes fluid to expel through a fluid outlet 440. The valve body 500 includes the fluid outlet 440 which may be selectively coupled to an output hose 506 for delivering pressurized fluid to a treatment site, such as through a treatment probe.

The fluid chambers 410, 420 are each separated from the fluid outlet 440 by an outlet valve 510a, 510b. This is in contrast to the embodiments of FIG. 4 which included a single output valve 450. The outlet valves 510a, 510b can be any suitable one-way valve such as, for example, ball valves, flapper valves, diaphragm valves, check valves, gate valves, pinch valves, knife valves, disc valves, clapper valves, duckbill valves, leaf valves, umbrella valves, dome valves, cross-slit valves, or any other suitable valve configuration. In some embodiments, the outlet valves 510*a*, 510*b* comprise a valve and a valve seat that allow fluid to flow therethrough in a fluid flow direction and inhibit reverse directional fluid flow therethrough. The outlet valves 510*a*, 510*b* can be positioned adjacent one another with a feature that inhibits them from contacting each other and sticking together, such as through hydrostatic force. The feature may be bumps or ridges formed on the valves themselves that inhibit the valves from making intimate surface contact with one another, or may be a stop formed in the housing 502 to prevent the outlet valves 510*a*, 510*b* from contacting one another. As described above, the outlet valves 510*a*, 510*b* can be any suitable valve now known or later developed that allow unidirectional fluid flow to selectively allow fluid to flow from one fluid chamber 410, 420 to the fluid outlet 440 while preventing backflow of fluid to the opposing fluid chamber 410, 420.

In some embodiments, a spring 512 is disposed between the outlet valves 510*a*, 510*b* that biases the valves apart. As pressure increases against one outlet valve 510*a*, it compresses the spring and pushes the outlet valve 510*a* toward the opposing outlet valve 510*b* thus creating a fluid flow path from the cylinder 460 through the fluid outlet 440. A spring located between the outlet valves 510*a*, 510*b* may urge the valves to close quicker which results in less regurgitation of fluid. In some embodiments, a spring is not provided, but rather, the outlet valves 510*a*, 510*b* are biased in one direction or another by hydrostatic forces. Similarly, a spring may be provided on the inlet valve to urge the inlet valve 430*a*, 430*b* to close quickly in the absence of positive fluid pressure.

The inclusion of multiple outlet valves 510*a*, 510*b* is believed to increase efficiency of the pumping cycle through the action of the output hose pressure influencing the open valve to close faster, and in some cases, before the opposing piston drives the opposing valve open. This may reduce premature closure of the opposing input valve and therefore improve pumping flow efficiency and provide for a smoother fluid pressure profile.

Figure 6:
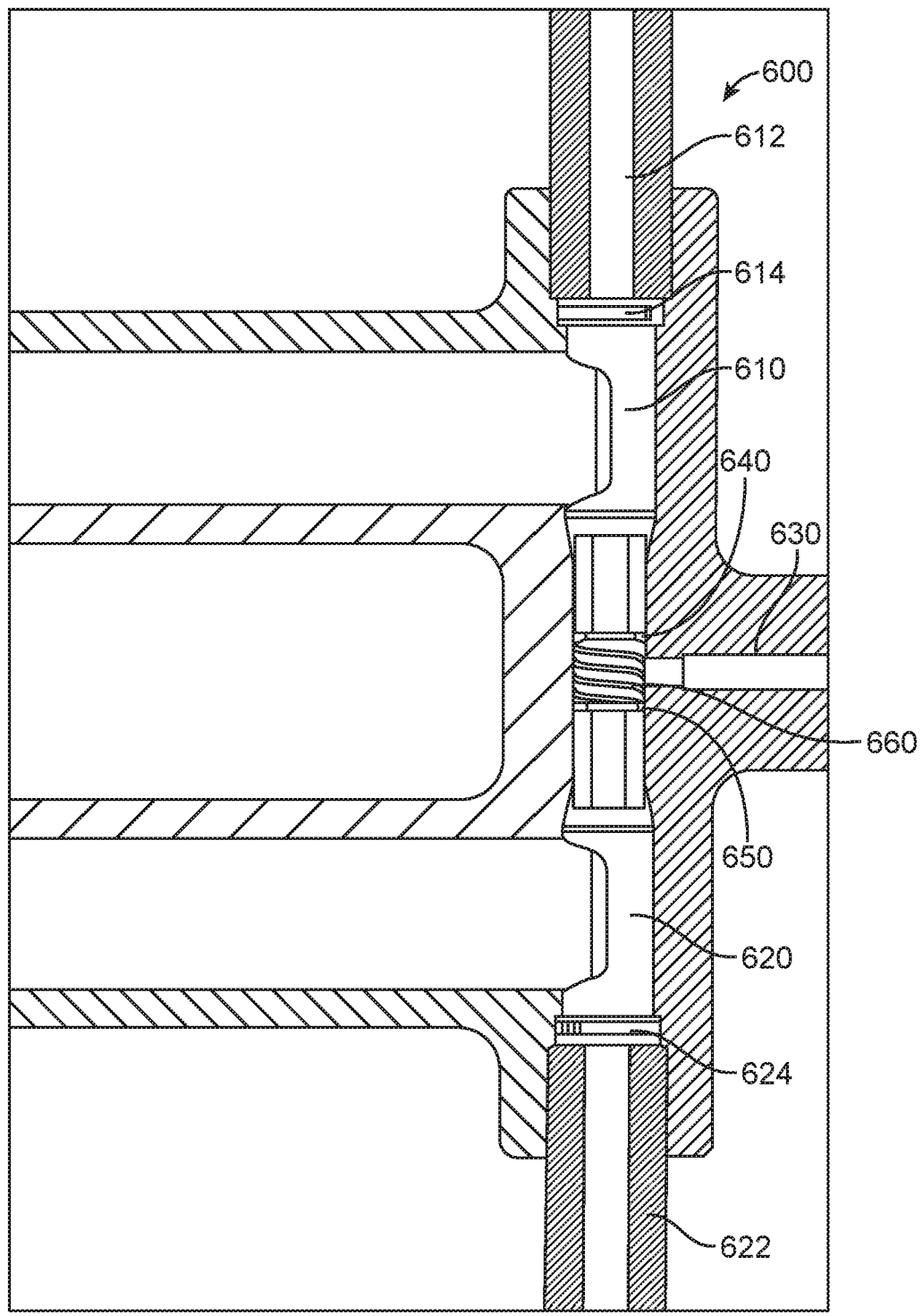
FIG. 6 shows a partial sectioned view of a valve body usable in a pump cartridge having a dual output valve with a spring, in accordance with some embodiments.

With reference to FIG. 6, a valve body 600, which may be substantially the same as valve body 500, defines a first fluid chamber 610 coupled to a first fluid inlet 612 by an inlet valve 614. As described, the inlet valve 614 may be any suitable one-way valve that allows fluid to enter the fluid chamber 610 from the fluid inlet 612, but inhibits fluid flow in the other direction.

Similarly, the valve body 600 defines a second fluid chamber 620 coupled to a second fluid inlet 622 by a second inlet valve 624. Of course, additional fluid chambers may be provided as desired to create alternative fluid pumping profiles.

The valve body 600 defines an outlet channel 630 through which fluid may leave the valve body 600. The outlet channel 630 may be machined into the valve body 600, may be a tube or hose coupled to the valve body 600 or may otherwise be formed or connected to the valve body 600. The first fluid chamber 610 and the second fluid chamber 620 are in selective fluid communication with the outlet channel 630 through respective outlet valves 640, 650. In some embodiments, the outlet valves 640, 650 are one-way valves that allow fluid to flow from the fluid chambers 610, 620, to the outlet channel 630. Each outlet valve 640, 650 comprises a valve seat that cooperates with a valve to engage with the valve seat to inhibit fluid flow therethrough. In some embodiments, the valve seat is formed of a ductile material to allow fluid pressure to cause the valve to deform the valve seat to form a more intimate surface contact between the valve and the valve seat. In some embodiments, forming the valve seat to have a surface area configured to contact the valve that is smaller than the cross-sectional area of the valve seat allows a higher contact pressure between the valve and the valve seat.

For example, if the valve seat has a generally annular cross-sectional area, forming the valve seat with a protruding conical shape, when pressurized, the water pressure pushing against the valve causes it to press on a small annular edge of the valve seat, thus causing the ductile material to plastically deform to cause an intimate surface contact with the valve. The valve seat may be formed during manufacture, such as by forming a chamfer on the inside diameter or the outside diameter of the valve seat.

The valve seat and/or the valve can optionally have a variety of configurations, such as D-shaped, star shaped, ovoid-shaped, disc shaped, triangular, four-fingered star, or some other shape. In some instances, the valve is sized and selected to reduce flow resistance and maximize flow volume. Maximizing the flow volume will reduce the likelihood of cavitation at the valves which maintains the output efficiency.

In the illustrated embodiments, a spring 660 biases each valve 640, 650 in a closed configuration. The spring 660 may be chosen to have a relatively low spring constant such that the fluid pressure caused by the pistons extending distally into the cylinder easily overcomes the spring force and opens the respective outlet valve 640, 650. The spring 660 may be positioned between the outlet valves 640, 650, such that when one valve is open, the spring is compressed and exerts a restoring force on the open valve urging it closed.

As the pistons reciprocate, when a driving piston reaches its top dead center position, it no longer increases fluid pressure within the respective fluid chamber, but rather, pressure quickly equalizes before the driving piston reverses its direction of travel. At this point, the spring enhances the closing time of the open valve and prevents back flow of pressurized fluid from the fluid outlet 630.

The spring 660 may optionally be a compression spring, a torsion spring, a leaf spring, or some other form of biasing member configured and located to urge the valves into their respective closed positions.

Figure 6A:
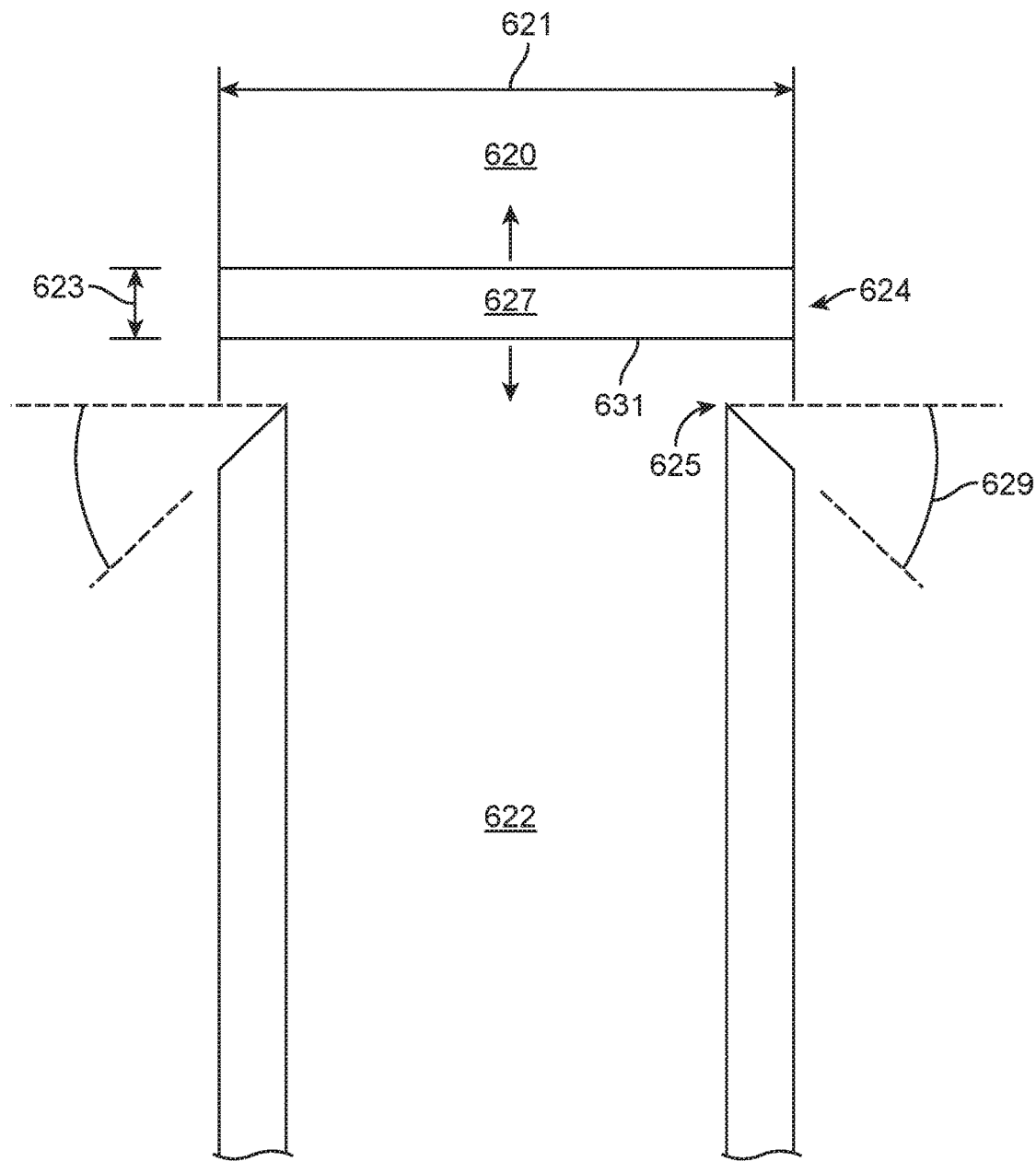
FIG. 6A shows valve comprising a tapered valve seat and seat and movable valve component, in accordance with some embodiments.
Figure 6B:
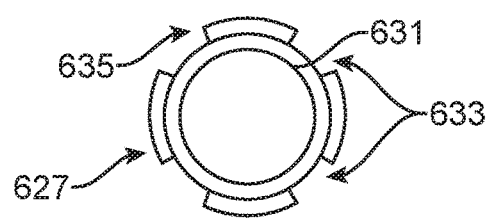
FIG. 6B show a movable valve component as in FIG. 6A, in accordance with some embodiments.
Figure 6C:
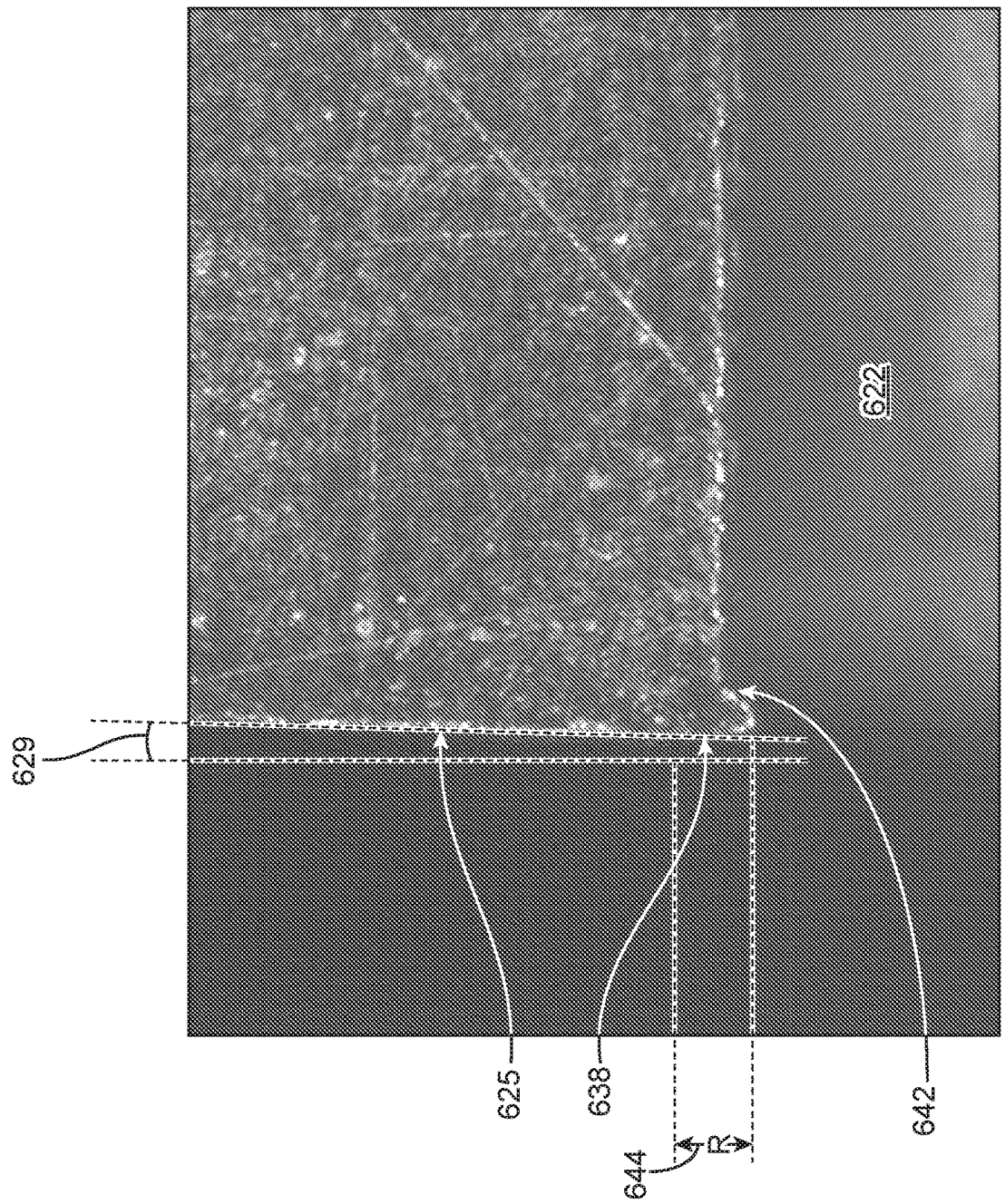
FIG. 6C shows a valve seat with deformation to improve sealing, in accordance with some embodiments.

FIGS. 6A, 6B and 6C show a valve comprising a tapered valve seat 625 and movable valve component 627. The tapered valve seat as described herein can be used with a single cylinder pump or a pump comprising a plurality of pistons and cylinders as shown in FIG. 6. The movable valve component 627 comprises a valve seat engaging portion 631. The valve seat 625 can be inclined with respect to a surface of the movable component of the valve, for example at an angle of inclination 629. The valve can be configured in many ways to provide increased pressure to valve seat 625. For example, the valve seat may comprise a tapered end or a thin flat end, such as rim, to provide increased pressure and deformation of the valve seat from the movable valve component 627 engaging the valve seat.

The deformation of the valve seat can occur in relation to the geometry of the end of the valve seat and the movable valve component, which engages the end of the valve seat. The valve seat may comprise a ductile material, such as stainless steel. In some embodiments, the valve seat may comprise austenitic steel, such as 304 stainless steel, for example. A plurality of valve seats can be configured for deformation. For example, a first valve seat and a second valve seat may each comprises a ductile material in order to shape a surface of the first valve seat to the first movable valve component and the second valve seat to the second movable valve component. The first valve seat and the second valve seat may each comprises a material softer than the movable component. In some embodiments, the valve seat may be formed of 304 stainless steel, and the moveable component may be formed of a harder material, such as a martensitic steel, for example 17-4 stainless steel. Alternatively, the first valve seat and the second valve seat may comprise a material less ductile than the movable component. Each valve seat may comprise a generally tapered end to engage the movable component. The tapered end may comprise an angle of inclination 629 within a range from about 1 degree to about 75 degrees relative to plane defined by the movable component engaging portion of the valve seat. The range can be from about 1 degree to about 30 degrees, for example. In some embodiments, the angle of inclination is about 1 degree to about 7 degrees, and in some embodiments, is about 3 degrees.

As shown in FIG. 6C, repeated contact between the tapered valve seat 625 and the moveable component may cause a flat annular ring 638 to form on the valve seat. The annular ring 638 has a width R 644 that is dependent, at least in part, upon the material properties of the valve seat 625, the moveable component, and the force at which the moveable component strikes the valve seat 625.

In some embodiments, the valve seat 625 is formed of a material having a tensile yield between about 30,000 psi and about 80,000 psi. In some embodiments, the moveable component is formed of a material having a tensile yield of from about 80,000 psi to about 130,000 psi. In some instances, the pressure within the fluid chamber 620 may be about 8,000 psi, which may result in a force on the valve seat of about 21 lbs. As shown by the experimental results and image of FIG. 6C, this may result in an annular ring 638 having a width R 644 of about 0.0035 inches. Through experimentation, this annular ring provided an acceptable seal of the moveable component against the valve seat 625. The image shown in FIG. 6C was obtained by cutting a used valve seat to obtain the cross-sectional view shown.

In one experiment, the moveable component was formed of a hardened, polished 17-4 stainless steel and the valve seat 625 was formed of 304 stainless steel with a 3-degree angle cone cut leaving the inner lumen edge higher than the outer edge. The 3-degree angle cone interfaces with the hardened moveable component which, under the operating pressure of the system, deforms the conical valve seat 625 surface creating a sealing surface (e.g., the annular ring 638), that matches the surface of the moveable component. The annular ring 638 may continue to deform until it reaches a surface area sufficient to support the moveable component without further plastic deformation of the valve seat 625. In some cases, a terminal pressure of about 30,000 psi will result in an annular ring 638 about a 0.059 inch lumen having a width R 644 of about 0.004 inches.

As can be seen, the deformation of the annular ring 638 causes a burr 642 to form toward the fluid inlet 622 inner chamber. The burr 642 may form as a result of cold-working, burnishing, or forging by the repeated colliding of the moveable component 627 and the valve seat 625 until the annular ring 638 reaches a surface area to support the moveable component without further deformation.

The moveable component 627 may comprise a maximum cross-sectional dimension 621 sized to fit in the fluid chamber 620 and a thickness 623 no more than the maximum cross-sectional dimension 621.

FIG. 6B shows a movable valve component as in FIG. 6A. The moveable valve component 627 may comprise a profile 635 around a perimeter. The movable valve component and valve seat may comprise a plurality of movable valve components and a plurality of valve seats configured for each of valves 614, 624, 640 and 650, for example. The movable valve component may define one or more channels 633 to allow fluid to pass through the channels from the cylinder to the outlet when the movable component is located away from the valve seat. For example, in embodiments where the valve comprises one or more of valves 640 or 650, the profile of the movable valve component may define one or more channels to allow fluid to pass through the channels from the respective cylinder to the outlet 630 when the movable component is located away from the valve seat.

The valve seat engaging portion 631 can be sized and shaped to engage the valve seat. The channel portion of the movable valve component 627 can be sized and shaped to define the one or more channels 633. The valve seat engaging portion 631 can be located radially inward from the channel portion. The perimeter 635 of the movable valve component 627 may corresponds to one or more of a star shape, a D shape, a polygon, a triangle, a rectangle, an ellipsoid, or a crescent, for example. In some embodiments the perimeter corresponds to an annular shape with an outer portion of the perimeter defined by an outer annular diameter and an inner portion of the perimeter defined by an inner annular diameter, with a plurality of grooves extending inwardly from the outer annular diameter to the inner annular diameter. In some embodiments, the valve seat engaging portion 631 comprises a diameter less than the inner annular diameter.

The hydraulic system as described herein may be characterized as an RC circuit in which the pressurized fluid has capacitance and the couplings, hoses, nozzles, and other physical components introduce resistance. Thus, the pressurized fluid stores energy as its flow is restricted. This induced hysteresis in the hydraulic system serves to provide a more consistent fluid pressure at the treatment end, which may be a treatment probe positioned within a patient. For example, the nature of two or more reciprocating pistons within a pump will provide a pulsating fluid flow having the same frequency as the reciprocating pistons, albeit with a slight lag due to fluid mass and induced resistance. The design of the outlet valves 640, 650, the selection of the outlet hose material, configuration, and length, in combination with all couplings will introduce resistance into the system which serves to smooth the pulsating frequency. In some embodiments, the resistance in the hydraulic system is designed to provide a smoother fluid flow profile than an unrestricted fluid flow profile. In this way, the working fluid at a tissue resection site may be delivered precisely, repeatably, and at a pressure that is relatively uniform over time.

Fluidic Seals and Supporting Structure

Figure 7:
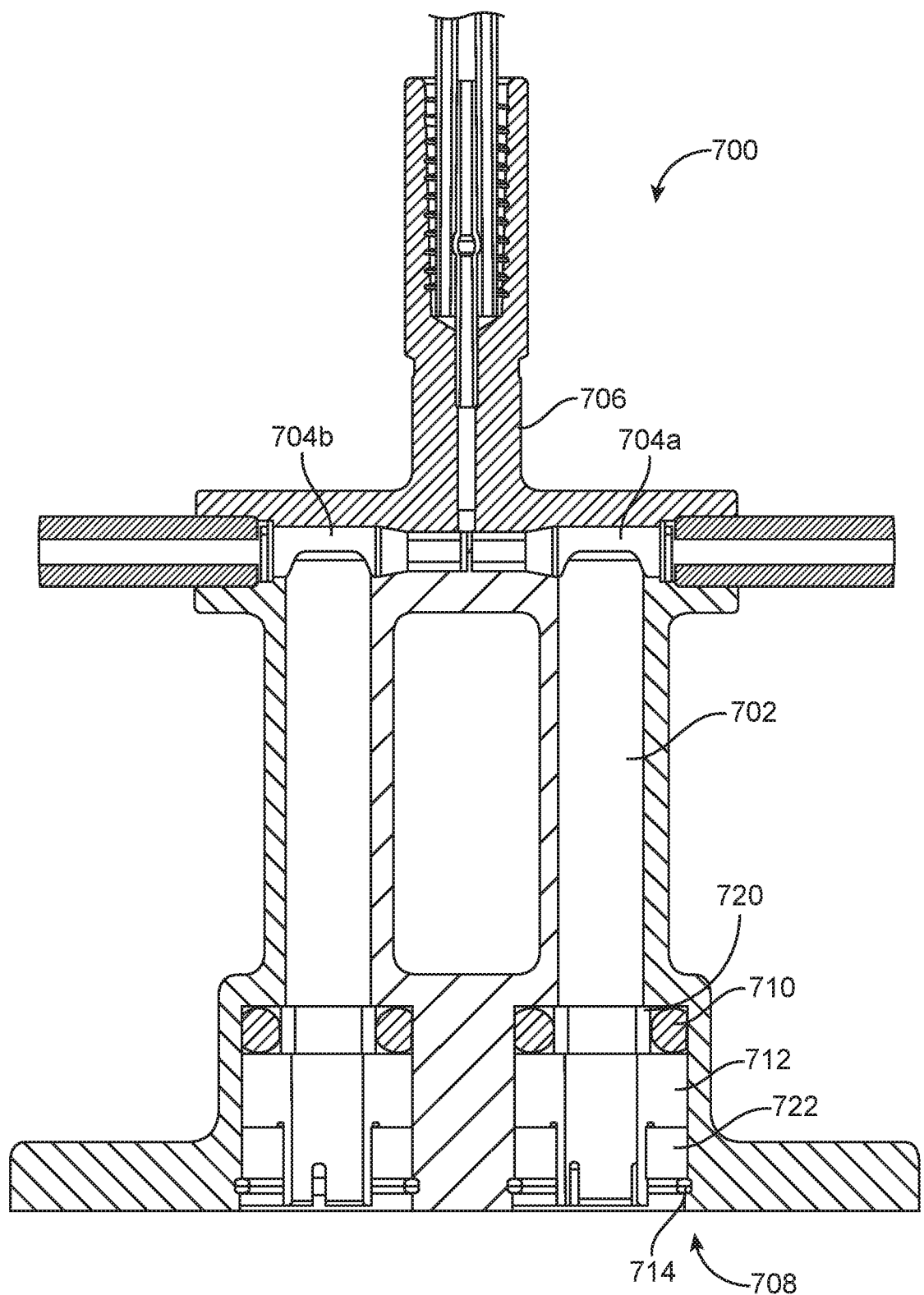
FIG. 7 shows a schematic diagram of a valve body usable in a pump cartridge having dual pistons and a sleeve with fluid seals, in accordance with some embodiments.

Turning now to FIG. 7, a valve body 700 is shown having structure to fluidically seal the channels 702. The valve body 700 may be substantially similar to valve body 500 or 600. Much of the fluid flow structure and apparatuses of the embodiments shown is substantially as previously described. As fluid enter the fluid chambers 704a, 704b, it is free to flow within the channels 702 formed in the housing. As used herein, the terms channel and cylinder are broad terms and may be used interchangeably. The terms refer to a void within the housing 706 configured to slidably accept a piston. In some embodiments, a channel integrally formed in the housing 706 provides the path for the piston. In other embodiments, a sleeve may be inserted into the channel to provide the path for the piston. In either case, the description herein is largely agnostic as to which piston supporting structure is present unless specified. Further, use of the term cylinder does not necessarily denote geometric structure, but rather, refers to a pathway that cooperates with a slidable piston to pressurize fluid.

The proximal end 708 of the housing 706 includes cooperating structure to inhibit fluid from leaking out of the proximal end 708 of the housing 706. An O-ring 710 provides an annular static seal on the housing 706. The O-ring 710 is compressed against the housing 706 by a sleeve 720. The O-ring deforms to make surface contact with the sleeve 720 and the housing 706 to create a fluid seal. The O-ring 710 is formed of any suitable material, but in some instances, is formed of nitrile rubber, hydrogenated nitrile butadiene rubber, or some other suitable material exhibiting excellent strength, retention of properties after prolonged use, and wear resistance.

The sleeve 720 additional provides a dynamic seal against the piston (not shown). Once the piston is inserted into the channel 702 and beyond the sleeve 720, the sleeve 720 is forced outwardly, thus compressing the O-ring 710 against the housing 706. The sleeve 720, by a restoring force exerted upon it from the compressed O-ring 710, makes intimate surface contact with the piston to provide a fluid tight reciprocating shaft seal. The sleeve 720 is preferably formed of a suitable material that is lubricious to allow the piston to slide relative to the sleeve 720 while maintaining a fluid tight seal. In some embodiments, the O-ring 710 and sleeve 720 may be combined into a single seal structure, such as a reciprocating shaft seal having radial type inner diameter and outer diameter sealing lips.

A bushing 712 additionally cooperates with the O-ring 710 to fluidically seal the housing 706. The bushing 712 further provides support and a pathway for the piston. A support washer 722 may be provided to add strength to the components and may be formed of metal or a high-strength polymer, or some other suitable material. A retainer 714 may be positioned within the housing 706 to secure the seal components in place, and may be formed as a steel snap ring. The retainer 714 may also be a screw-in plug, such as a hollow set screw, or may be formed by crimping one or more components in place.

While a single arrangement of seals has been shown, other suitable seals are possible without departing from the spirit and scope of the disclosure. Additional seal arrangements are shown in the figures and accompanying description, but one of ordinary skill in the art would readily recognize other methods and structures for providing a fluid-tight seal of the housing 706.

Figure 8:
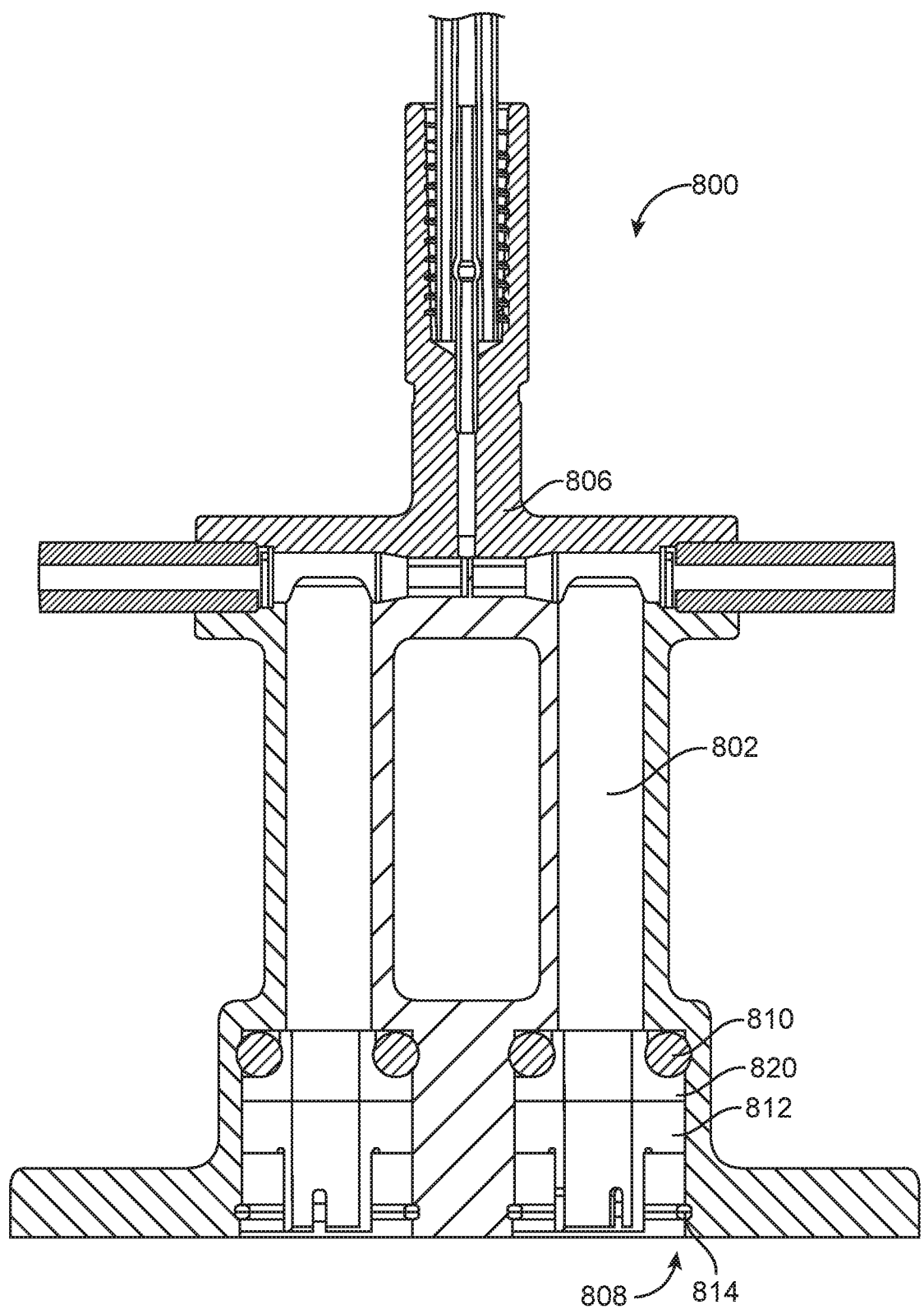
FIG. 8 shows a schematic diagram of a valve body usable in a pump cartridge having dual pistons and a saddle sleeve with fluid seals, in accordance with some embodiments.

FIG. 8 illustrates another embodiment of a seal for a valve body 800. Much of the fluid flow structure and apparatuses of the embodiments shown is substantially as previously described. The housing 806 defines recesses configured to support and engage one or more seal components. As illustrated, an O-ring 810 is provided and engages against a saddle sleeve 820 to provide a fluid tight seal between the channel 802 and the proximal end 808 of the housing 806 sleeve. The saddle sleeve 820 is configured to cooperate with the O-ring 810 to provide a compressive force to the O-ring 810 to cause the O-ring to form a seal against the housing 806. The restoring force of the compressed O-ring 810 causes the saddle seal 820 to make surface contact with the piston and provide a fluid tight seal therewith. The saddle seal 820 has a parallel position relative to the piston, which allows the mating surfaces to be in intimate contact sufficient to provide the seal.

A bushing 812 guides the piston into the channel 802 and provides support to maintain coaxial orientation between the piston and the channel 802. A retainer 814 may be provided, as has been described herein.

Figure 9:
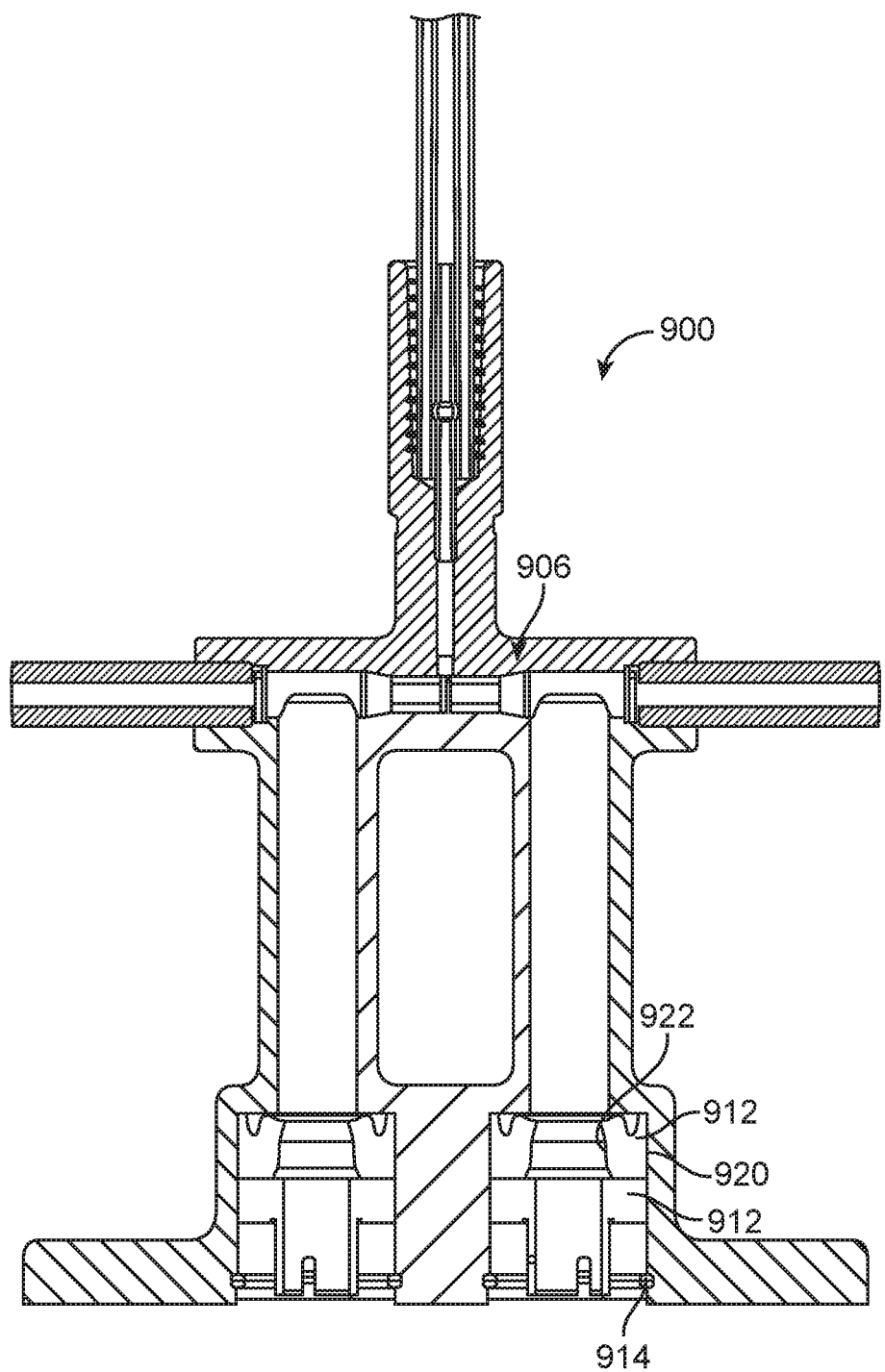
FIG. 9 shows a schematic diagram of a valve body usable in a pump cartridge having dual pistons and a cup seal, in accordance with some embodiments.

FIG. 9 illustrates another type of seal applicable to embodiments described herein. The valve body 900 includes a housing 906 as previously described, and may be substantially similar to valve body 500. The housing defines a cavity for a cup seal 910, a bushing 912, and a retainer 914. The cup seal 910 may be a U-cup seal which has a U-shaped profile and includes an outside static sealing lip 920 and an inside dynamic sealing lip 922. This type of seal provides both the static and dynamic seal required by the reciprocating piston within the channel 902. The cup seal may be formed of any suitable material, but in some instances, may be formed of nitrile, urethane, highly saturated nitrile, or polytetrafluoroethylene. In some instances, the cup seal 910 may optionally include an O-ring inside the cup to provide additional support for the seal and aid in providing a restoring force to bias the cup seal 910 against the piston.

Figure 10:
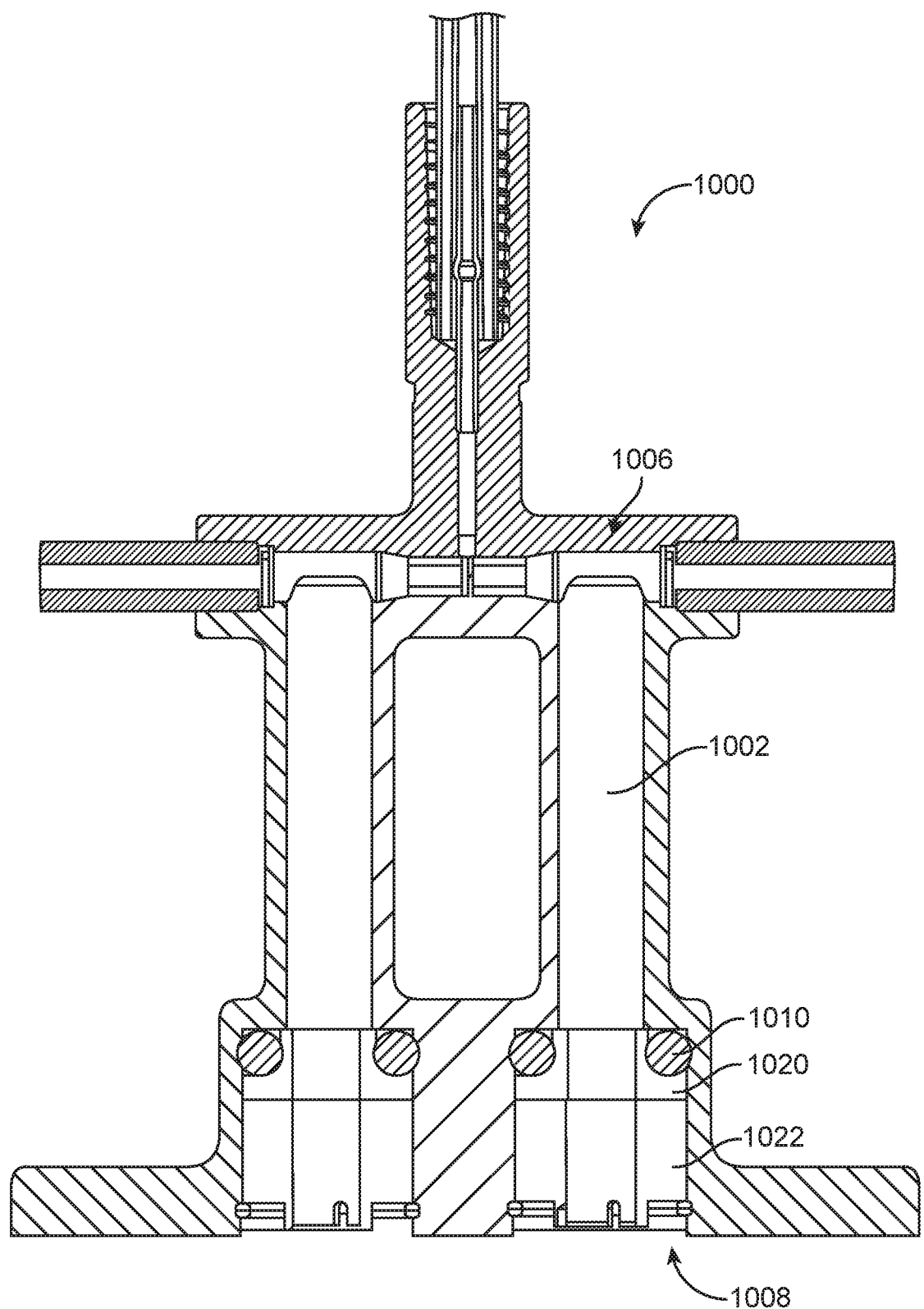
FIG. 10 shows a schematic diagram of a valve body usable in a pump cartridge having dual pistons and a saddle sleeve with fluid seals, in accordance with some embodiments.

FIG. 10 illustrates a valve body 1000 having another arrangement of sealing structure to provide a fluid seal of the housing 1006 at the proximal end 1008. Much of the fluid flow structure and apparatuses of the embodiments shown is substantially as previously described. As illustrated, an O-ring 1010 is supported by a saddle sleeve 1020. A bushing 1022 provides a guide for a piston and urges the piston to maintain a coaxial relationship with the channel 1002. This embodiment differs in design with previous embodiments, such as is illustrated in FIG. 8, by the one-piece bushing which allows the elimination of the metallic support washer. In this instance, the housing 1006 may define capturing structure to secure the bushing 1022, the saddle sleeve 1020, and the O-ring 1010 in place. The capturing structure may be formed as grooves, bosses, protrusion, or some other structure integrally formed with, or attached to, the housing 1006 to couple the sealing components within the housing 1006.

Figure 11:
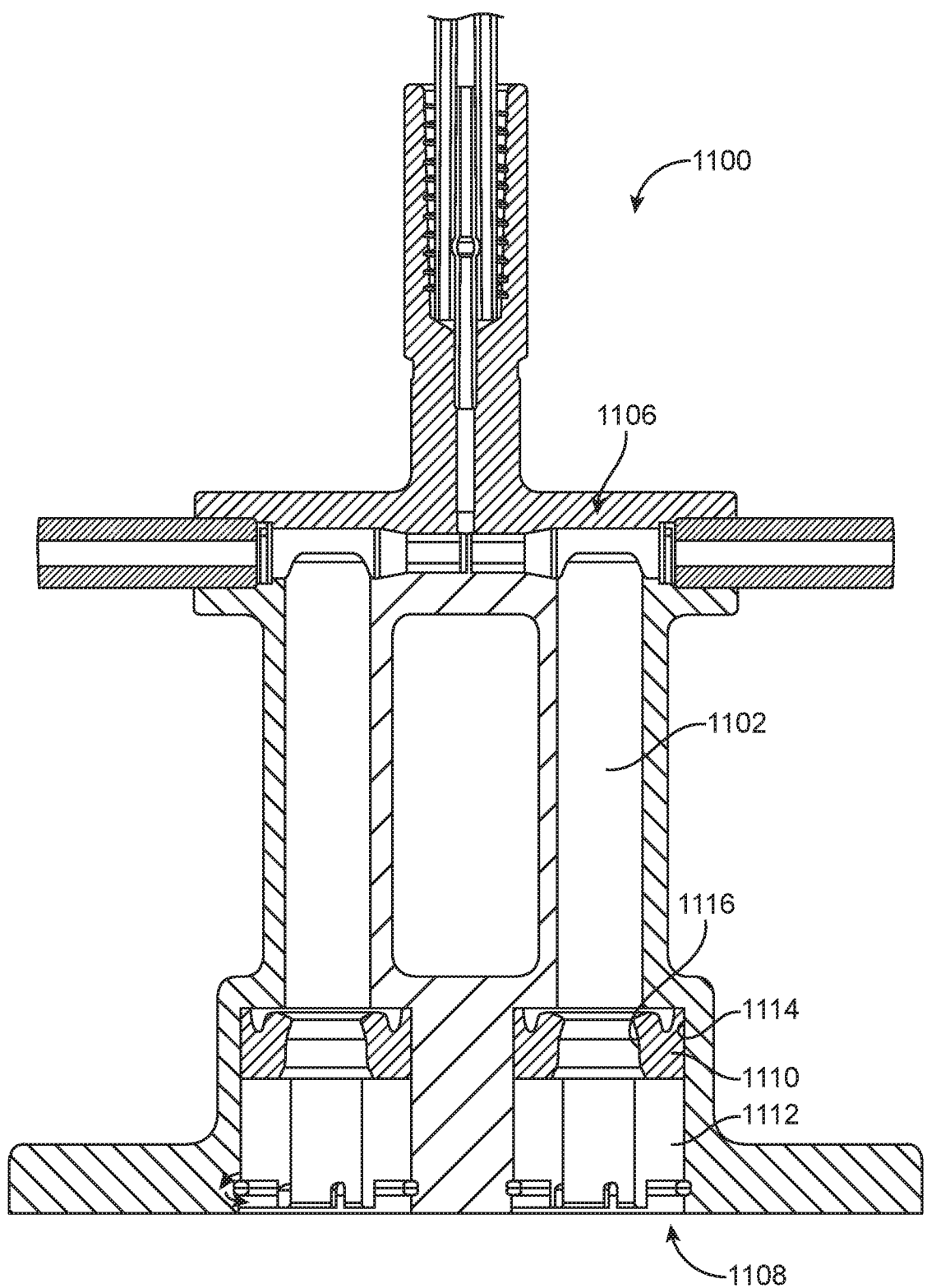
FIG. 11 shows a schematic diagram of a valve body usable in a pump cartridge having dual pistons and a cup seal, in accordance with some embodiments.

FIG. 11 illustrates a valve body 1100 having a housing 1106 that defines at least one channel 1102. Much of the fluid flow structure and apparatuses of the embodiments shown is substantially as previously described. The valve body 1100 includes a seal at its proximal end 1108. The seal may comprise a cup seal 1110, which in some embodiments is a U-cup seal. The cup seal 1110 may be annular and have a U-shaped cross section have two seal portions spaced to contact the housing 1106 and a piston disposed in the channel 1102. The two seal portions comprise a static seal lip 1114 and a dynamic seal lip 1116. The static seal lip 1114 is biased against the housing 1106 to inhibit fluid egress from within the channel 1102 out the proximal end 1108 of the valve body 1100. The static seal lip 1114 does not move relative to the housing 1106 thus providing a static seal. The dynamic seal lip 1116 is biased against a piston extending therethrough and the piston moves axially with respect to the dynamic seal lip 1116, thus providing a dynamic seal against the piston. The piston is thus able to reciprocate along its axis while maintaining a fluid tight seal against the dynamic seal lip 1116 of the cup seal 1110.

A bushing 1112 provides support for the cup seal 1110 and the piston (not shown). The bushing is held in the housing 1106 by any suitable mechanism, but in some, embodiments is secured by fitting in grooves or capturing protrusions that cooperate with the bushing 1112 to securely hold the bushing 1112 in place. The bushing 1112 provides support for the piston that extends therethrough and reciprocated within the channel 1102. The bushing may be formed of a lubricious material that provides for a relatively low friction sliding contact with the piston.

Figure 12:
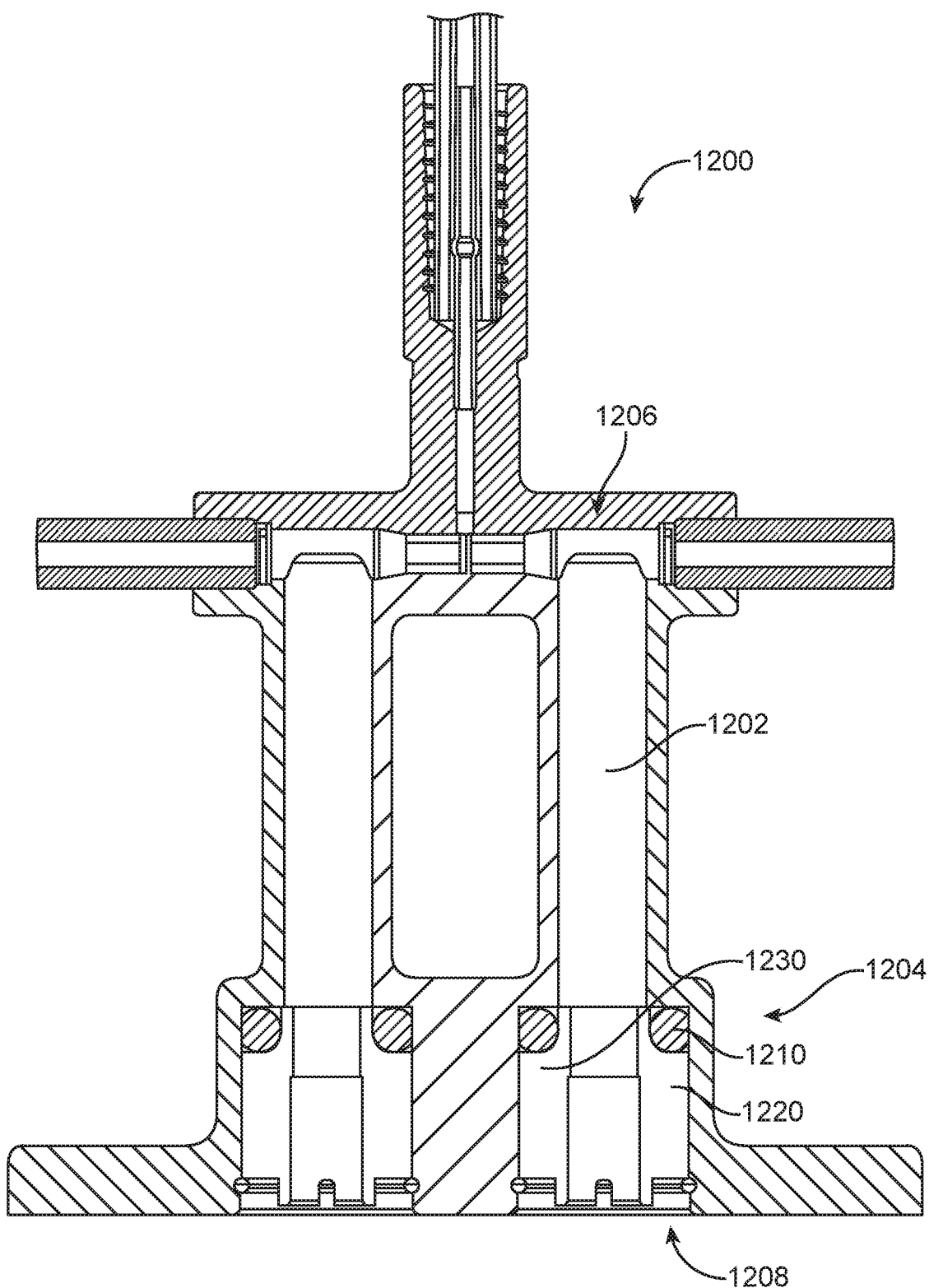
FIG. 12 shows a schematic diagram of a valve body usable in a pump cartridge having dual pistons, a saddle sleeve and a fluid seal, in accordance with some embodiments.

FIG. 12 illustrates a valve body 1200 having a channel 1202 defined by a housing 1206. Much of the fluid flow structure and apparatuses of the embodiments shown may be substantially as previously described. A seal 1204 disposed at or near the proximal end 1208 of the valve body 1200 inhibits fluid leakage from within the housing 1206. As illustrated, an O-ring 1210 is supported by a bushing 1220. The bushing 1220 and O-ring 1210, in some instances, are annular and fit within a cylindrical cavity formed in the housing 1206. Once assembled, a piston extends from outside the housing 1206 and through the bushing 1220. The piston and bushing 1220 are disposed coaxially and the bushing 1220 provides guidance and support to maintain the piston in its coaxial relationship with the bushing 1220 and further, coaxial with the channel 1202 formed in the housing 1206. The piston engages with the bushing 1220 and biases the bushing 1220 to expand in a radial direction. The bushing 1220, in turn, compresses the O-ring 1210 against the housing 1206. The O-ring 1210, as it compresses, elastically deforms against the housing 1206 to provide a static fluid-tight seal against the housing. The O-ring 1210 additionally provides resistance against the bushing 1220 by its restorative force resulting from compression, and biases the bushing 1220 against the piston, thereby causing intimate surface contact between the inner surface of the bushing 1220 and the outer surface of the piston, thus creating a dynamic fluid-tight seal between the piston and the bushing 1220, even as the piston reciprocates within the channel 1202.

The bushing 1220 and O-ring 1210 may be formed of suitable materials selected to have the advantageous characteristics described herein, such as wear resistance, seal characteristics, lubricity, ductility, spring constant, and other characteristics that make the sealing members suitable for their intended purposes. Of course, once the fluid is pressurized within the housing 1206, the fluid pressure will exert additional sealing force on the bushing 1220 and the O-ring 1210 to further improve the effectiveness of the seal members.

As illustrated in this, and other figures, the housing defines a first channel 1202 configured to receive a piston slidably therein. A second channel 1230 is formed in the housing, and has a diameter that is larger than the diameter of the first housing. The second channel 1230 is configured to securely hold the sealing members, including any bushings, sleeves, retaining members, deformable seals, or other structure that effectuates a fluid tight seal and retaining the sealing members in their proper position and orientation.

Pump Cartridge and Valve Body

Figure 13:
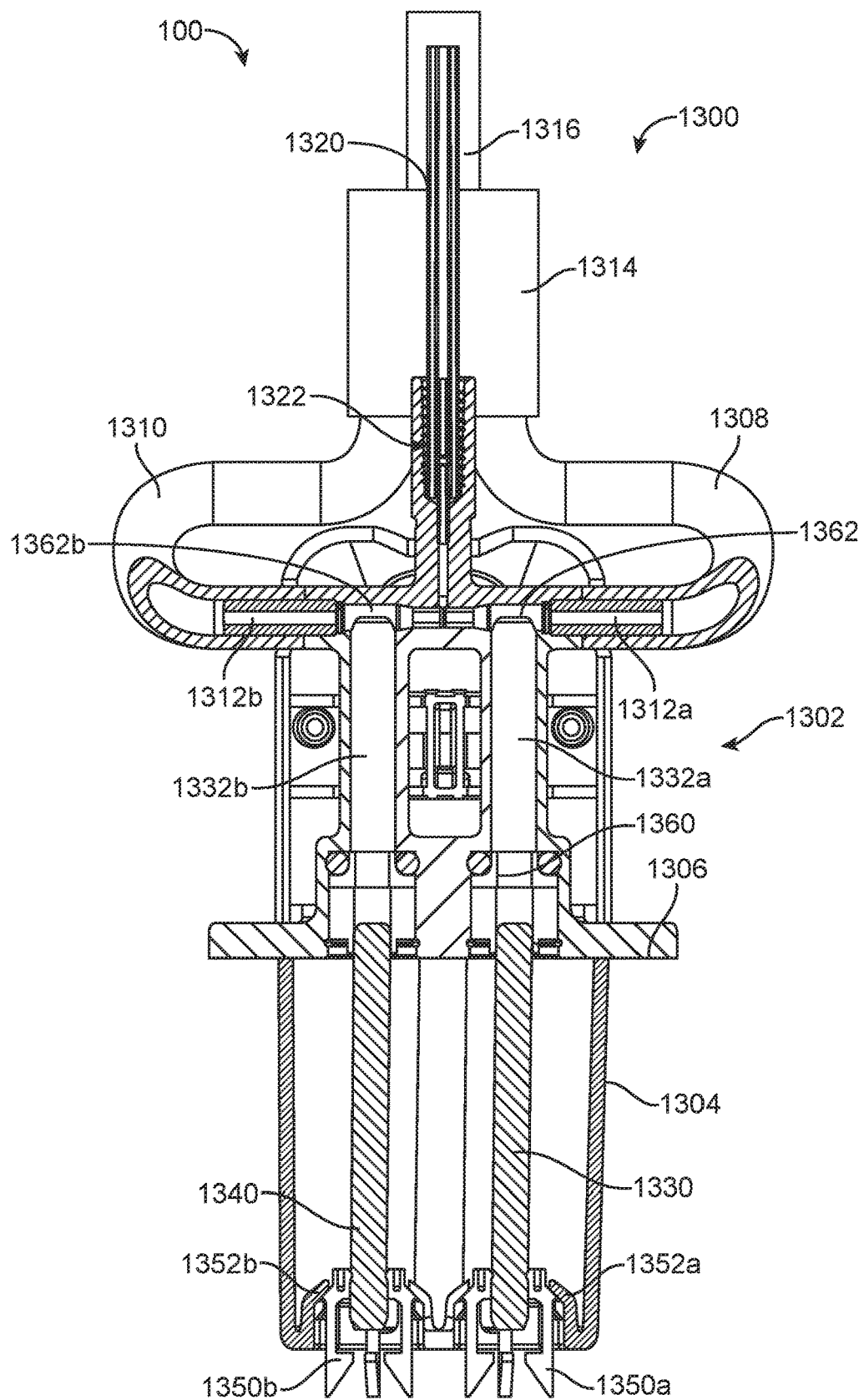
FIG. 13 shows a schematic diagram of a pump cartridge configured in a transit position, in accordance with some embodiments.

FIG. 13 illustrates a cartridge 100 that incorporates a valve body 1302 as has been substantially described herein. The cartridge 100 has a casing 1304 that provides support for and covers at least a portion of the valve body 1302. The casing 1304 provides a secure connection of the valve body 1302 and may incorporate fasteners, clips, cooperating friction fit members, or other suitable structure that captures and secures the valve body 1302 within the casing. In some embodiments, one or more of the coupling flanges 1306 is captured by holes in the casing 1304 to secure or aid in securing the valve body 1302 into the casing 1304. One or more fluid delivery lines 1308, 1310 can be coupled to the fluid inlets 1312a, 1312b to provide working fluid to the interior of the valve body 1302. In some embodiments, the working fluid is saline solution, deionized water, distilled water, or some other aqueous solution that may have additional therapeutic agents therein. The fluid delivery lines 1308, 1310 can be coupled to any source of fluid, such as any of a number of medical fluid bags.

The cartridge 100 has one or more hose supports 1314 to support the fluid delivery lines 1308, 1310 to inhibit relative movement between the fluid deliver lines 1308, 1310 and the cartridge 100, to ensure a secure connection of the fluid delivery system to the cartridge 100.

The cartridge 100 further has additional outlet hose supports 1316 to support the outlet hose 1320. The outlet hose 1320 may be attached to the valve body 1302 through any suitable mechanism, but in some embodiments, is secured by a crimp joint, a threaded coupler 1322, or a combination. Of course, other attachment mechanisms are contemplated herein, such as a luer lock, a clip-on fastener, or some other suitable mechanism.

As illustrated, pistons 1330, 1340 are shown disposed within the casing 1304 and only partially extending into the valve body 1302. As can be seen, the pistons 1330, 1340 are appropriately sized to reciprocate within channels 1332a, 1332b formed in the housing of the valve body 1302.

The pistons 1330, 1340 are shown in a transit position, or a configuration that is ready to be shipped, delivered, and installed into a pump. The pistons 1330, 1340 are shown in a proximal, retracted position and engagement structure 1350a, 1350b configured to initially cooperate with a retention structure 1352a, b to secure the pistons in the illustrated transit position.

In this configuration, with the engagement structure 1350a, 1350b, coupled to the retention structure 1352a, 1352b, the piston is in a locked position and is not free to move relative to the valve body 1302. More specifically, the pistons 1330, 1340 do not contact the seal lip or the seal structure, thus allowing communication with the interior of the valve body 1302, such as for allowing sterilant gas to enter the channels 1332a,b and the fluid chambers 1362a,b. Furthermore, by inhibiting contact between the pistons 1330, 1340 and the seal structure 1360 during manufacturing, shipping, and storage prior to use, the phenomenon of material weld and creep over time is eliminated or at least reduced, and the seal structure 1360 remains intact until the cartridge 100 is put in use and the pistons 1330, 1340 are allowed to advance into the channels 1332a, 1332b.

In some embodiments, the engagement structure 1350a is attached to the piston 1330 through any suitable mechanism. In some cases, the engagement structure 1350a is connected to the piston 1330 through a cooperating annular flange and groove. For instance, the piston 1330 may have an annular groove formed therein, and the engagement structure 1350a may have an annular flange on an inner diameter that snaps into the annular groove formed in the piston 1330.

In the illustrated transit position, the engagement structure 1350a, 1350b is removably secured to the retention structure 1352a, 1352b. The retentions structure 1352a, 1352b may have a sloped inwardly extending protrusion that captures a surface of the engagement structure 1350a. An axial force causes the engagement structure 1350 to be released from the retention structure 1352a as will be described hereinafter.

Figure 14:
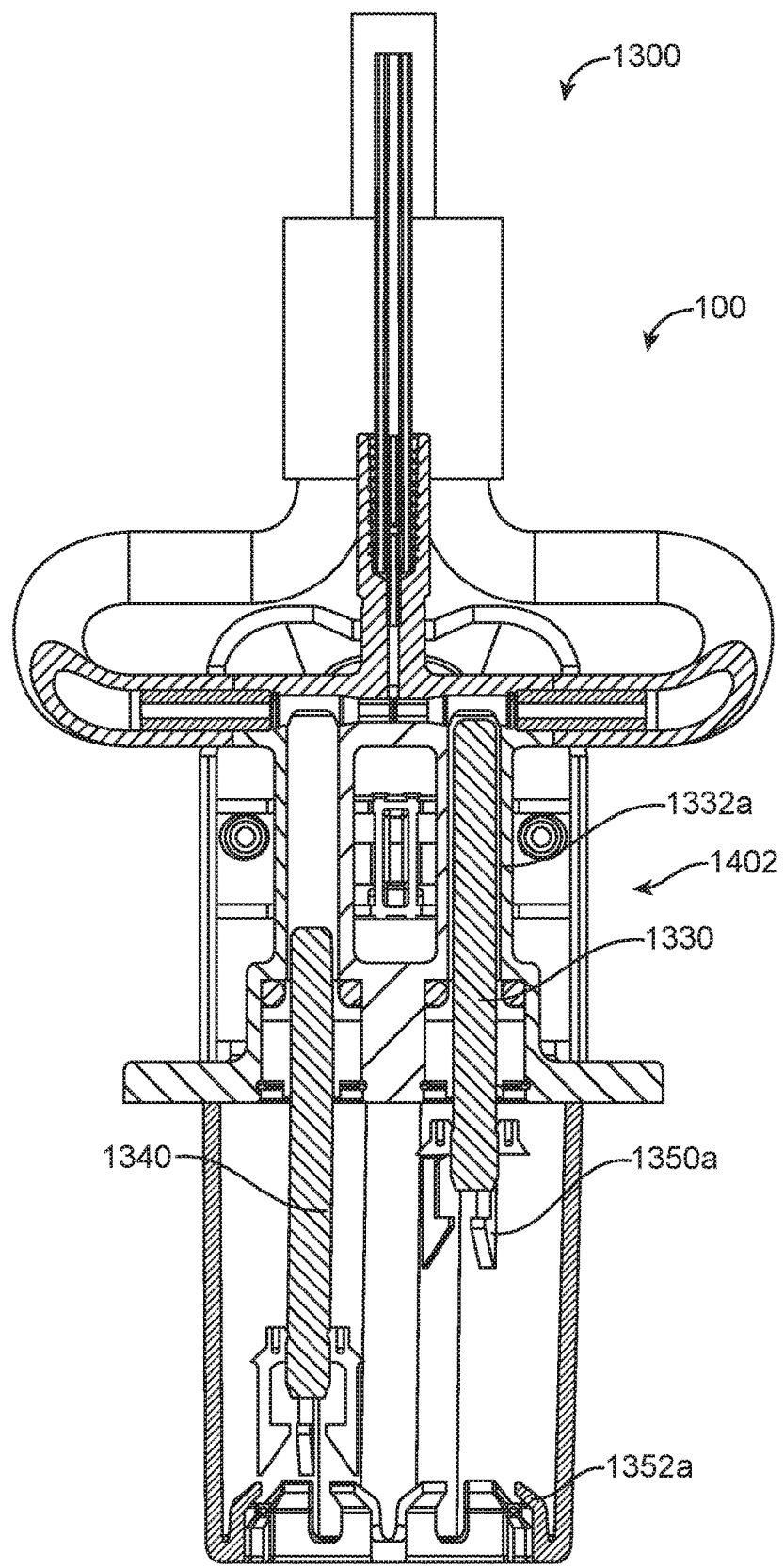
FIG. 14 shows a schematic diagram of a pump cartridge loaded in a pump and configured in a pumping position in accordance with some embodiments.

With reference to FIG. 14, a cartridge 1300 is illustrated that may be the same cartridge as illustrated in FIG. 13, or may have slight variations, such as, for example, the sealing structure at the proximal end of the valve body may be of a different configuration than what is illustrated. As shown, the piston 1330 is advanced into the channel and the engagement structure 1350a disengages from the retention structure 1352a. In some instances, one or both of the engagement structure 1350a and the retention structure 1352a elastically deform to allow the piston 1330 to advance into the chamber.

As shown, the piston 1330 is advanced to a top dead center position and is at the extent of its travel in a distal direction. The opposing piston 1340 is at its bottom dead center position and is at the limit of its travel in a proximal direction. A motor may drive an output shaft that drives control rods or pushrods to convert the motors rotary motion into linear activation. The control rods may be out of phase with one another, such that when a first control rod pushes, the second control rod pulls in an opposite direction. The control rods can be coupled to the pistons by the engagement structure 1350a and can thereby reciprocate the pistons 1330, 1340 within the channel.

Figure 15:
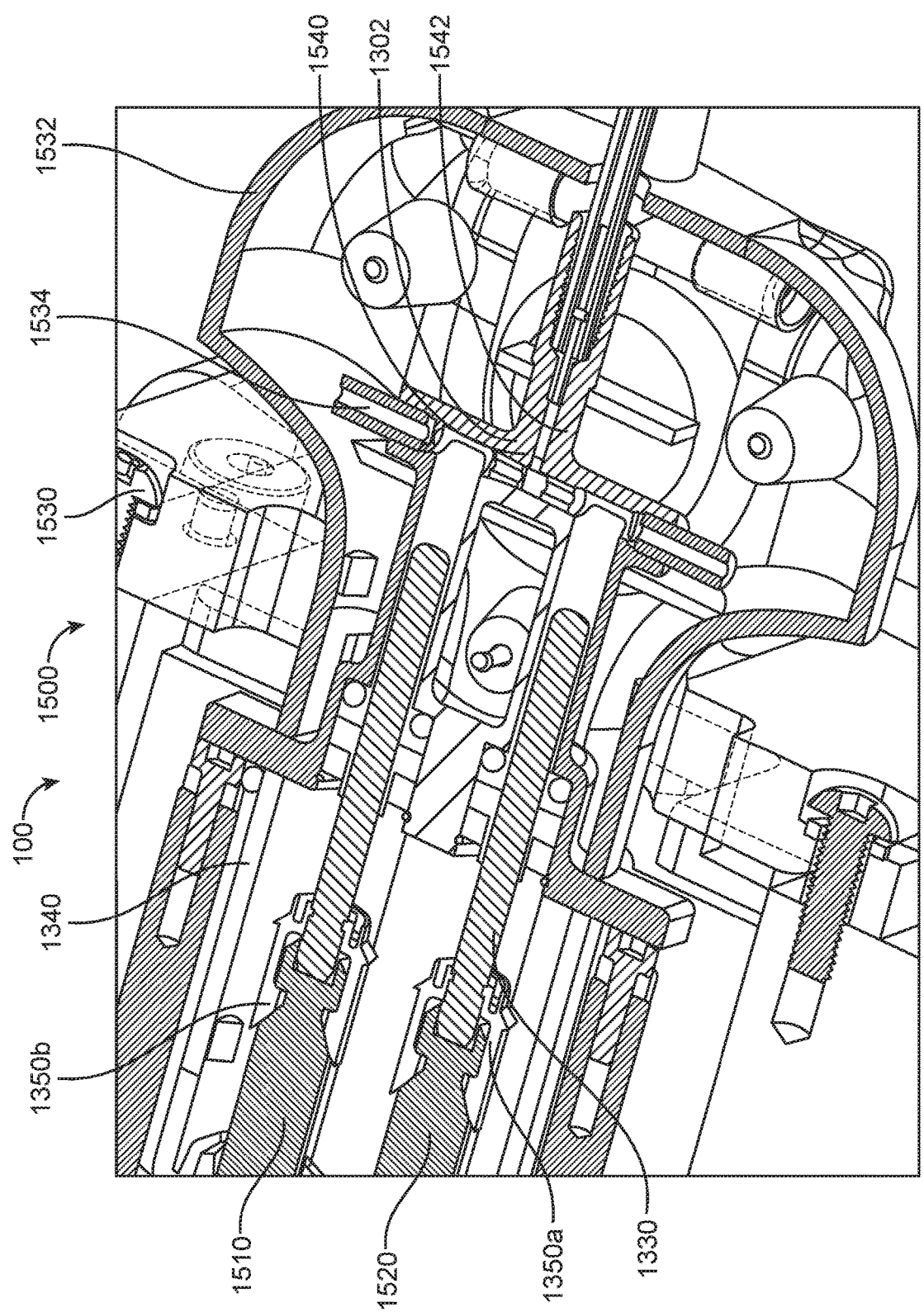
FIG. 15 shows a partial sectional view of a pump cartridge having dual pistons engaged with control rods by engaging members carried by the pistons, in accordance with some embodiments.
Figure 16:
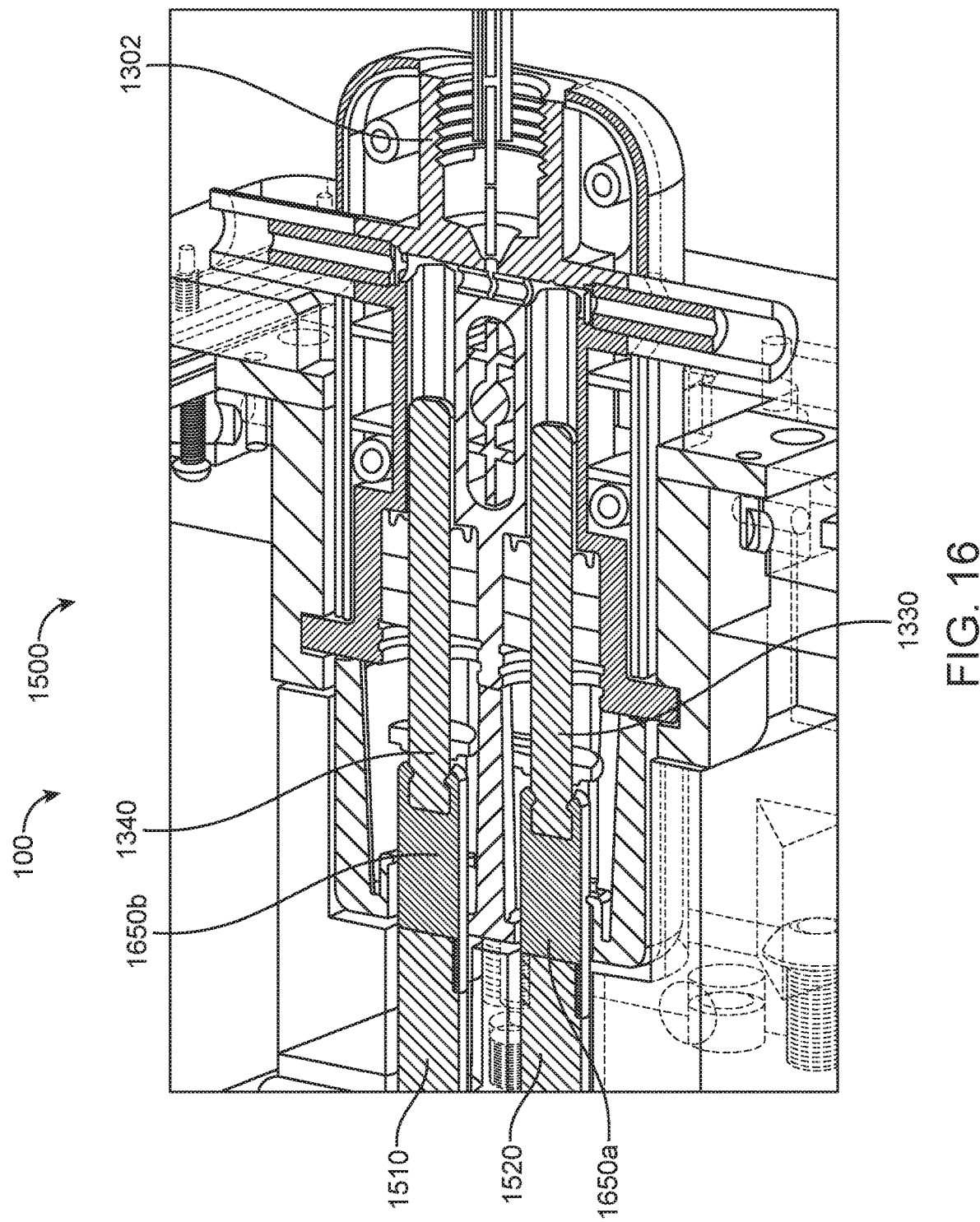
FIG. 16 shows a partial sectional view of a pump cartridge having dual pistons engaged with control rods by engaging members carried by the control rods, in accordance with some embodiments.

With reference to FIGS. 15 and 16, a cutaway view of the cartridge 1500 is shown and illustrates the orientation of the valve body 1302, the pistons 1330, 1340, the engagement structure 1350a, 1350b and the control rods 1510, 1520 that are shown coupled to the engagement structure 1350a, 1350b to drive the pistons 1330, 1340. The cartridge 1500 may be substantially the same as described above in relation to FIG. 13 or 14. Some embodiments utilize control rods 1510, 1520 that are coupled to drive the pistons 1330 in two directions along the longitudinal axis of the piston. In other embodiments, a control rod 1510 may be a pushrod, and only provides a power stroke to advance the piston 1330 and the piston 1330 retracts by another force, such as fluid pressure, a spring force, or some other force the causes the piston 1330 to retract. However, the terms "control rod" and "pushrod" may be used interchangeably and refer to a transmission member that transfers rotation from a motor into linear reciprocal motion of the pistons.

One difference between the cartridges 1500 shown in FIGS. 15 and 16 is the structure used to couple the control rods 1510 with the piston 1340. For example, in FIG. 15, the engagement structure 1350a is securely connected to the piston 1330 and is removably connected to the control rod 1520, while in FIG. 16, the engagement structure 1650a, 1650b is securely connected to the control rod 1510, 1520 and is removably coupled to the piston 1330, 1340. While either configuration of the engagement structure 1350a, 1350b or 1650a, 1650b will work, in some instances, locating the engagement structure on the piston allows the control rods to be withdrawn from the cartridge 1500 and the cartridge 1500 can be replace with another.

In use, a motor will drive an output shaft, which may be a crankshaft, or may be outfitted with lobes or some other type of cam structure, and cooperating couplings can connect the control rods to the lobes, cams, or crankshaft and convert the rotational output of the motor into linear reciprocating motion of the control rods. The control rods, when coupled to the pistons, cause the pistons to reciprocate within their respective channels. For example, as the motor drives the control rod 1510, the linear motion is transmitted to the piston 1340 which reciprocates linearly within channel 1530. As the piston 1340 moves proximally in the channel 1530, a vacuum is created by the withdrawal of the piston from the channel and working fluid is drawn into the fluid chamber 1532 through the fluid inlet 1534. As used herein, the term "vacuum" does not refer to an absolutely vacuum, but rather, refers to a reduced pressure that causes fluid flow from an area of higher pressure into the fluid chamber 1532 which has a lower fluid pressure caused by the withdrawing piston 1340. As one piston moves proximally and draws in fluid, the opposing piston 1330 advances distally within its respective channel and increases the fluid pressure. The increased fluid pressure, as described elsewhere herein, opens the output valve 1540 and expels the fluid through the output hose 1542.

The rotational nature of the motor will continue to drive the pistons in a reciprocating motion, with each piston drawing in fluid during its stroke from top dead center to bottom dead center, and expelling fluid through the fluid outlet 1542 as the piston is driven from its bottom dead center position to its top dead center position. The pistons may be driven 180 degrees out of phase, such that in a system having two pistons, they are driven oppositely. Of course, other configurations may provide for more, or fewer, pistons and they can be driven by any drive mechanism and at any suitable frequency and phase shift. For example, in some embodiments, three pistons can be driven 120 degrees out of phase with one another and cooperate to provide a fluid flow through the output hose 1542. In some embodiments, four pistons can be driven 90 degrees out of phase with one another to provide an output fluid flow. In some embodiments, the motor is driven from about 10 Hz to about 300 Hz, or from about 20 Hz to about 200 Hz, or from about 50 Hz to about 150 Hz.

Figure 17:
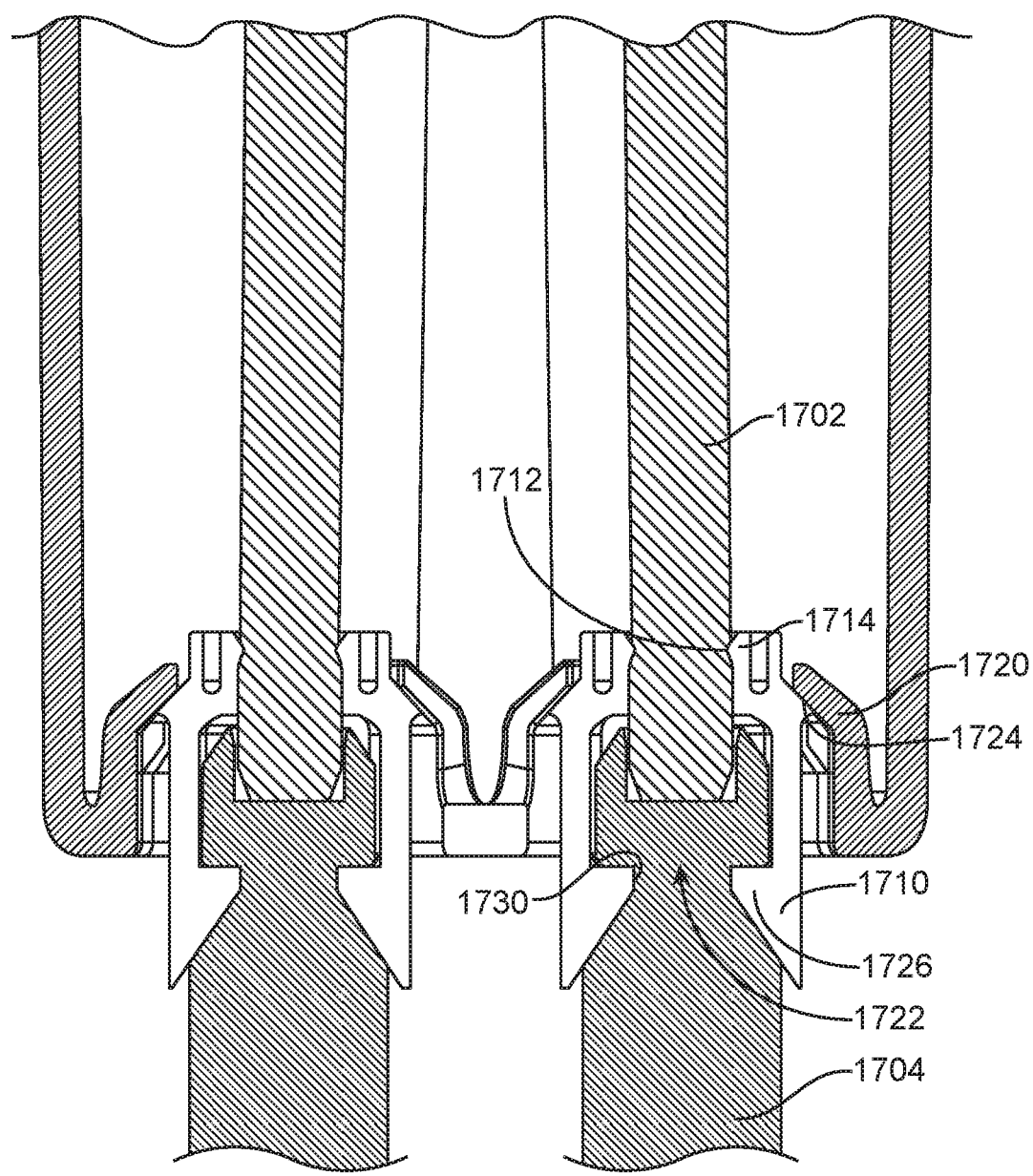
FIG. 17 shows a schematic diagram of dual pistons of a pump cartridge engaged with control rods of a pump, in accordance with some embodiments.
Figure 18:
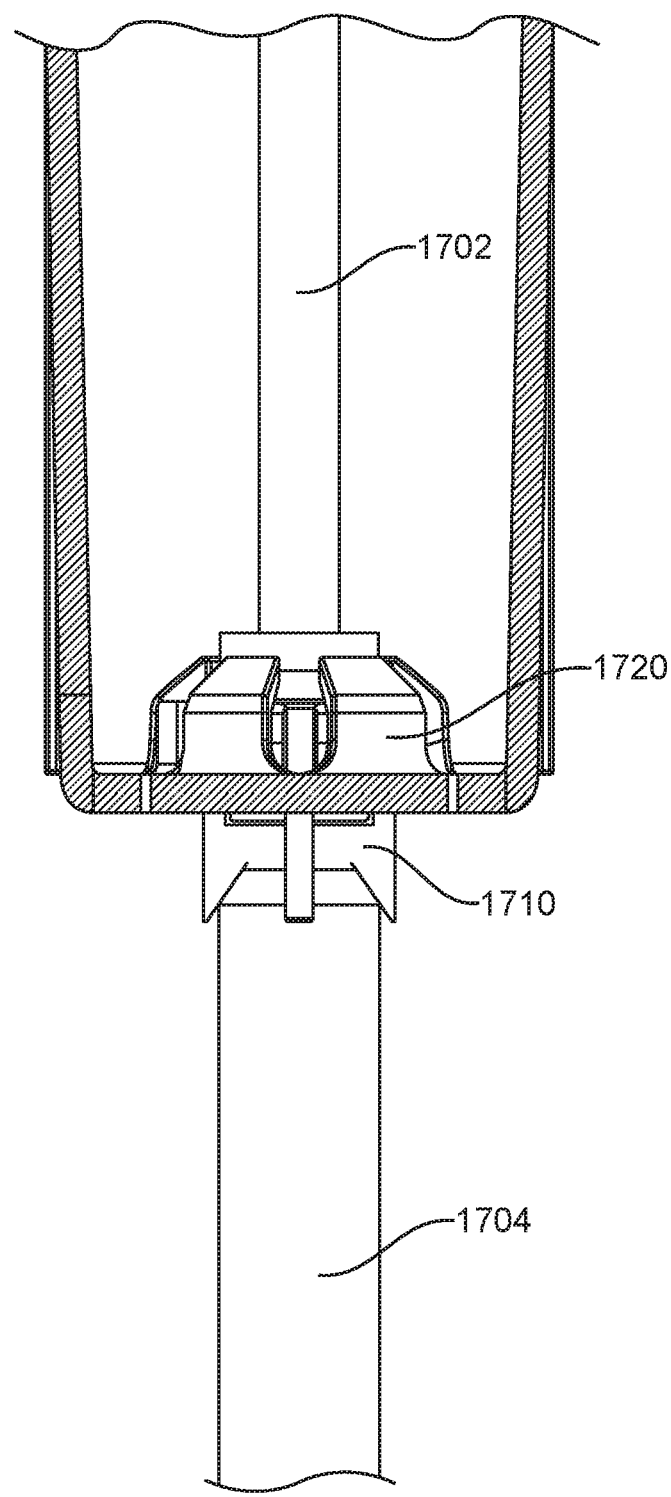
FIG. 18 shows a schematic diagram of a piston and a control rod coupled by an engagement member, in accordance with some embodiments.

With reference to FIGS. 17 and 18, a piston 1702 is coupled to a control rod 1704 by an engagement structure 1710. As can be seen, the engagement structure 1710 is carried by the piston 1702 by a groove 1712 formed in the piston 1702 and a cooperating annular protrusion 1714 on the engagement structure 1710. The engagement structure 1710 may be formed of any suitable material, such as any of a number of plastics, metals, composite materials, or a combination. In some embodiments, the engagement structure 1710 is formed of a material that is able to elastically deform in order to expand to securely engage with the piston 1702 and the control rod 1704. The illustrated structure of coupling a piston to a control rod may be usable in any embodiment described herein. For example, the engagement structure used with any embodiment described herein may have fingers that grasp the control rod 1704. As the control rod 1704 is advanced to be coupled with the piston 1702, the fingers elastically deform outwardly to accept the distal end 1722 of the control rod 1704 and then resiliently return to their shape to capture the distal end 1722 of the control rod 1704.

In the illustrated transit or shipping configuration, the engagement structure 1710 is initially secure attached to the piston. The engagement structure 1710 is additional held in a fixed position by interference with the retention structure 1720. The retention structure 1720 has a sloped surface 1724 that interferes with movement of the engagement structure 1710. In this initial transit configuration, the piston 1702 is held in a fixed position and is inhibited from advancing into the channel and coming in contact with the seal members (not shown).

Prior to use of the cartridge, the cartridge is installed into the loader mechanism that connects the cartridge with the transmission that supplies energy from the motor to the pistons. As part of the installation of the cartridge, the control rod 1704 is moved relative to the piston 1702 and the distal end 1722 of the control rod 1704 contacts the engagement structure 1710. The control rod 1704 and engagement structure 1710 have cooperating structure that allow the control rod 1704 to be coupled to the engagement structure, and therefore, in driving engagement with the piston 1702. The control rod 1704 may have one or more grooves, slots, detents, or pockets that accept a protrusion or boss from the engagement structure 1710 to secure the two devices together.

The engagement structure 1710 may be coupled to the control rod 1704 by advancing the cartridge linearly toward the control rods 1704. That is, the cartridge may move along the longitudinal axis of the piston to contact the control rod 1704. This may be done, for example, by manually pushing the cartridge toward the control rods, by a motor, a lever, a cam, or some other suitable mechanism, details of which will be discussed in further detail hereinafter. Of course, the cartridge may remain stationary and the control rods and optionally other supporting structure associated with the control rods may translate toward the cartridge to effectuate coupling of the control rods to the pistons.

A first axial force causes the engagement structure 1710 to elastically deform and accept the distal end 1722 of the control rod 1704. Protrusions 1726 on the engagement structure 1710 are forced outwardly as the control rod 1704 initially contacts the engagement structure 1710, and then snap back into place as the protrusions 1726 find purchase in the groove 1730 formed in the control rod 1704.

Upon coupling the control rod 1704 to the piston 1702 via the engagement structure 1710, a second axial force, greater than the first axial force, causes the retention structure 1720 to elastically deform outwardly as the sloped surface 1724 is pushed outwardly by the engagement structure 1710 being advanced into the cartridge.

In some embodiments, the engagement structure 1710 is able to retract the piston with an amount of force within a range from about 1 pound to about 20 pounds without disengaging from the control rod 1704.

Figure 19:
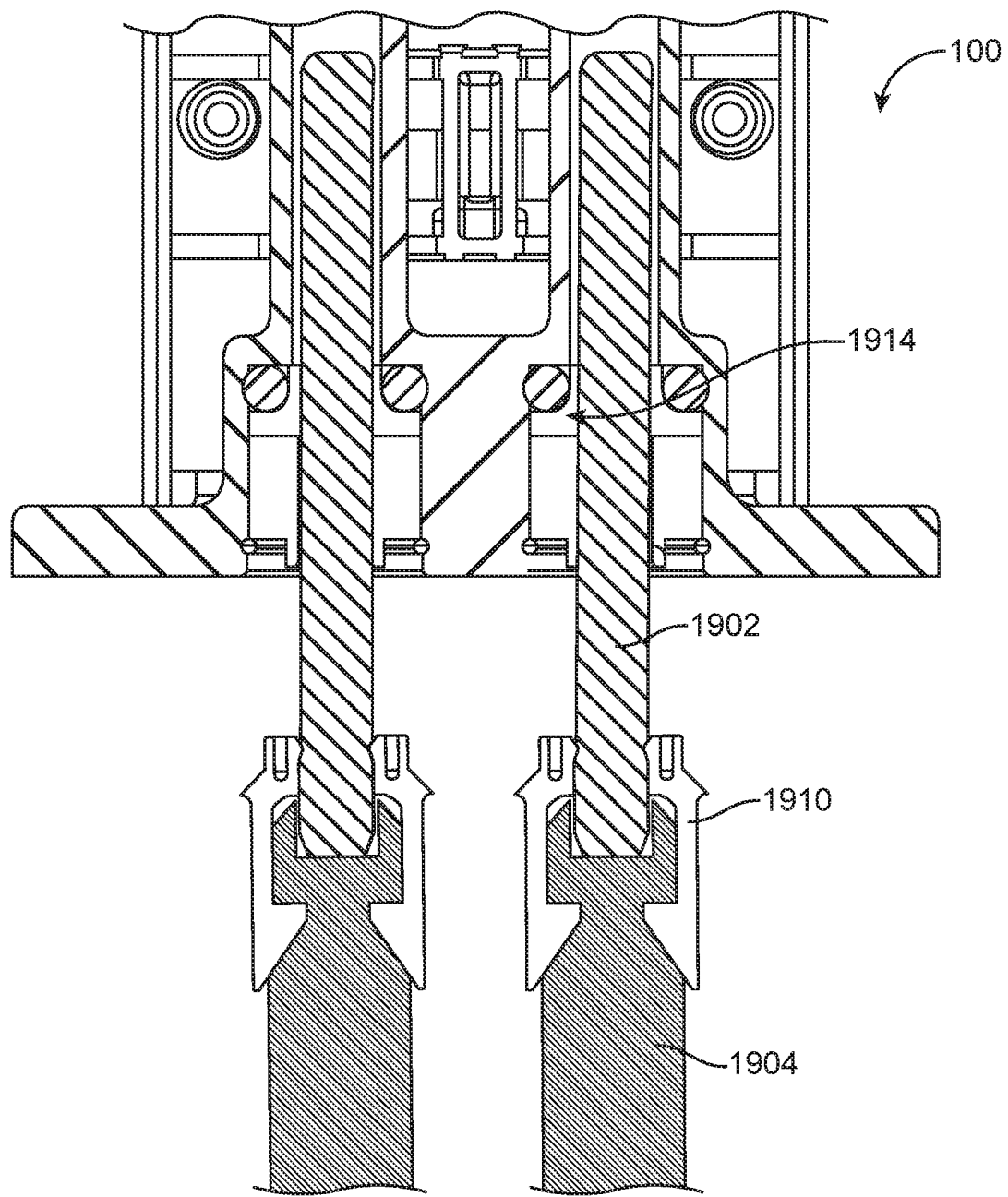
FIG. 19 shows a schematic diagram of a valve body usable in a pump cartridge having dual pistons coupled to control rods by engagement members, in accordance with some embodiments.

FIG. 19 shows the piston 1902 after it has been coupled to the control rod 1904 by the engagement structure 1910. As can be seen, the piston 1902 has been advanced beyond the seal members 1914 and the engagement structure 1910 is free of the retention structure.

Cartridge Loader

Figure 20:
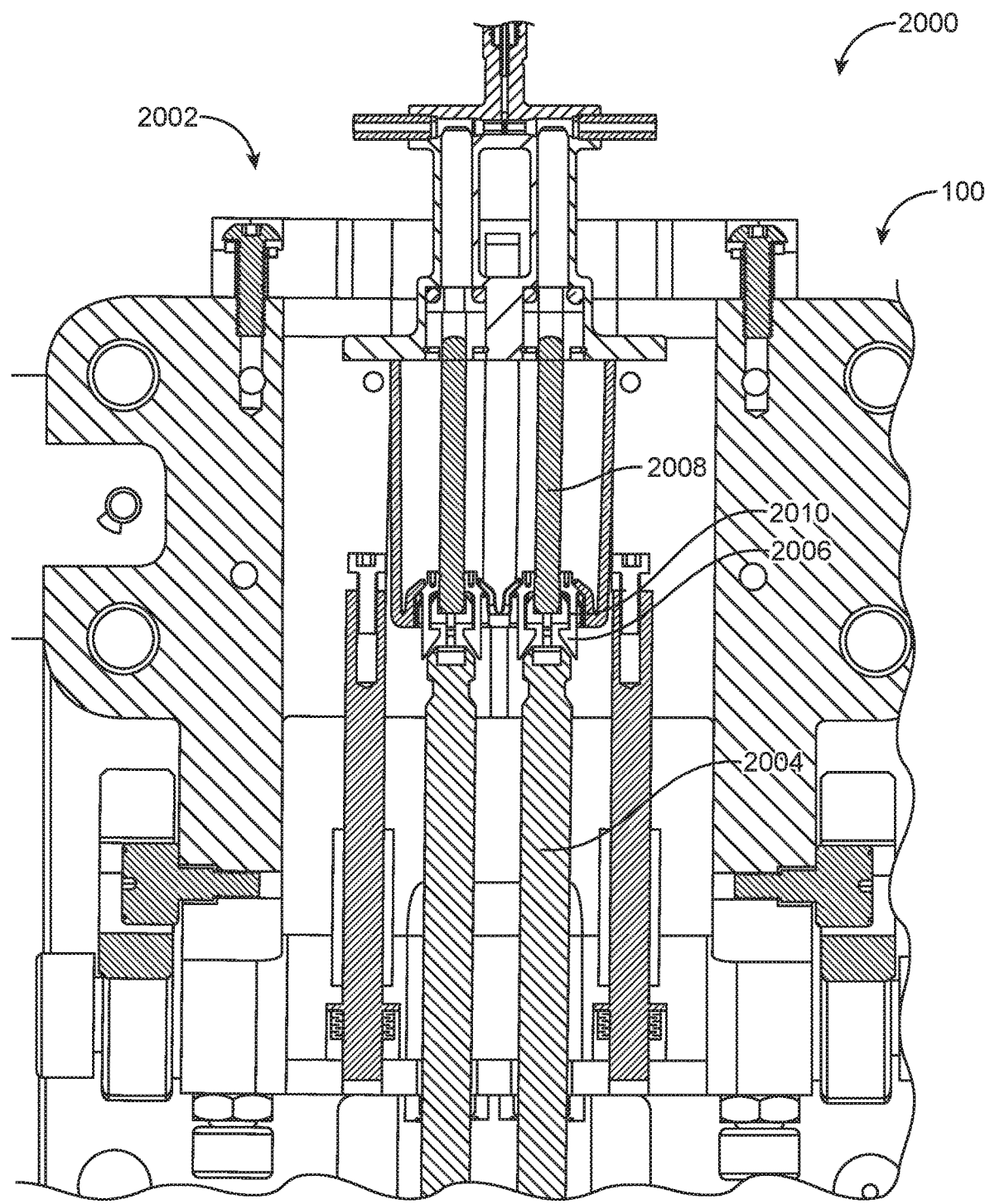
FIG. 20 shows a schematic diagram of a cartridge loader with a pump cartridge in an initial position, in accordance with some embodiments.
Figure 21:
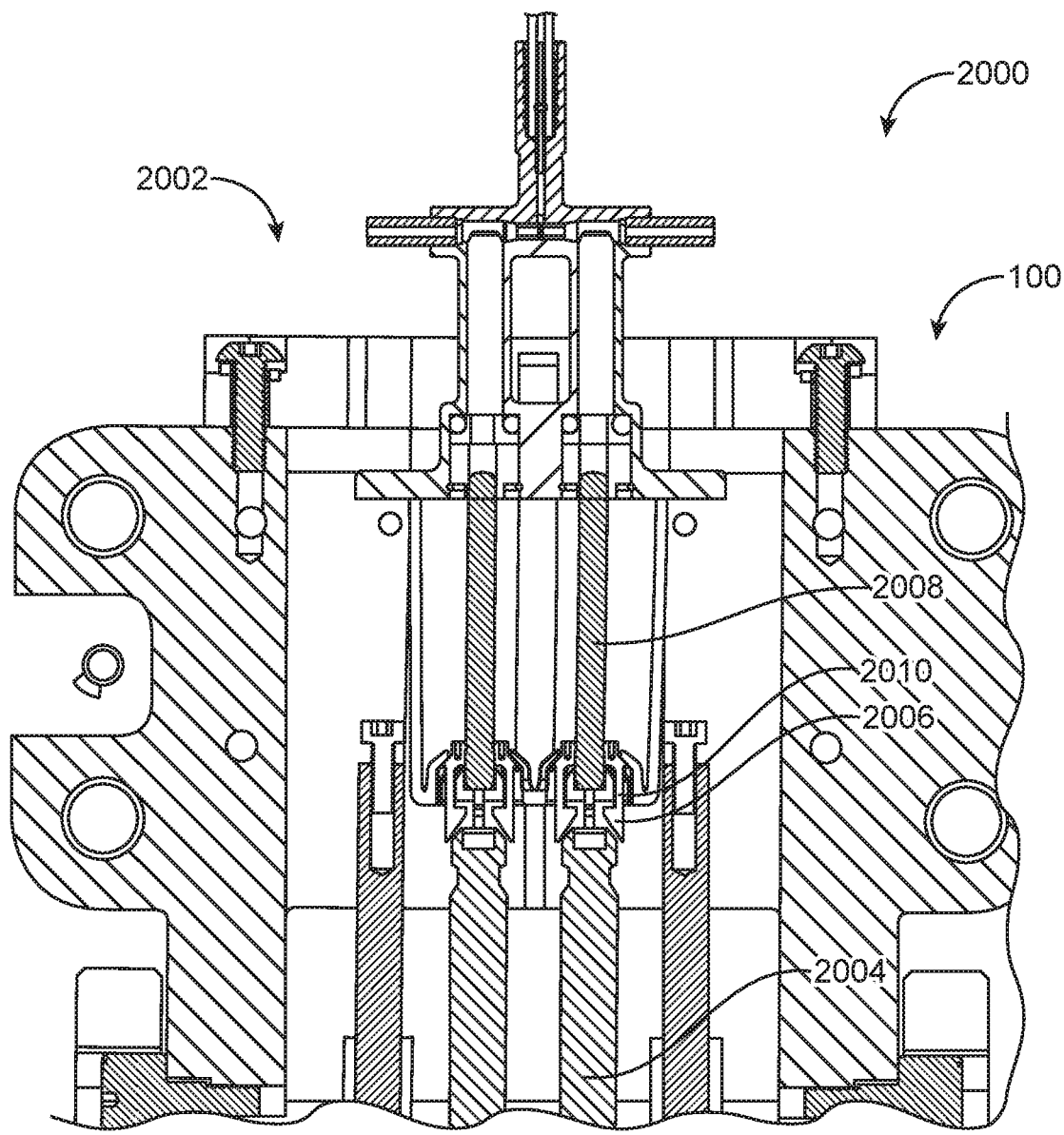
FIG. 21 shows a schematic diagram of a cartridge loader with a pump cartridge and a pump with pushrods in an initial position, in accordance with some embodiments.
Figure 22:
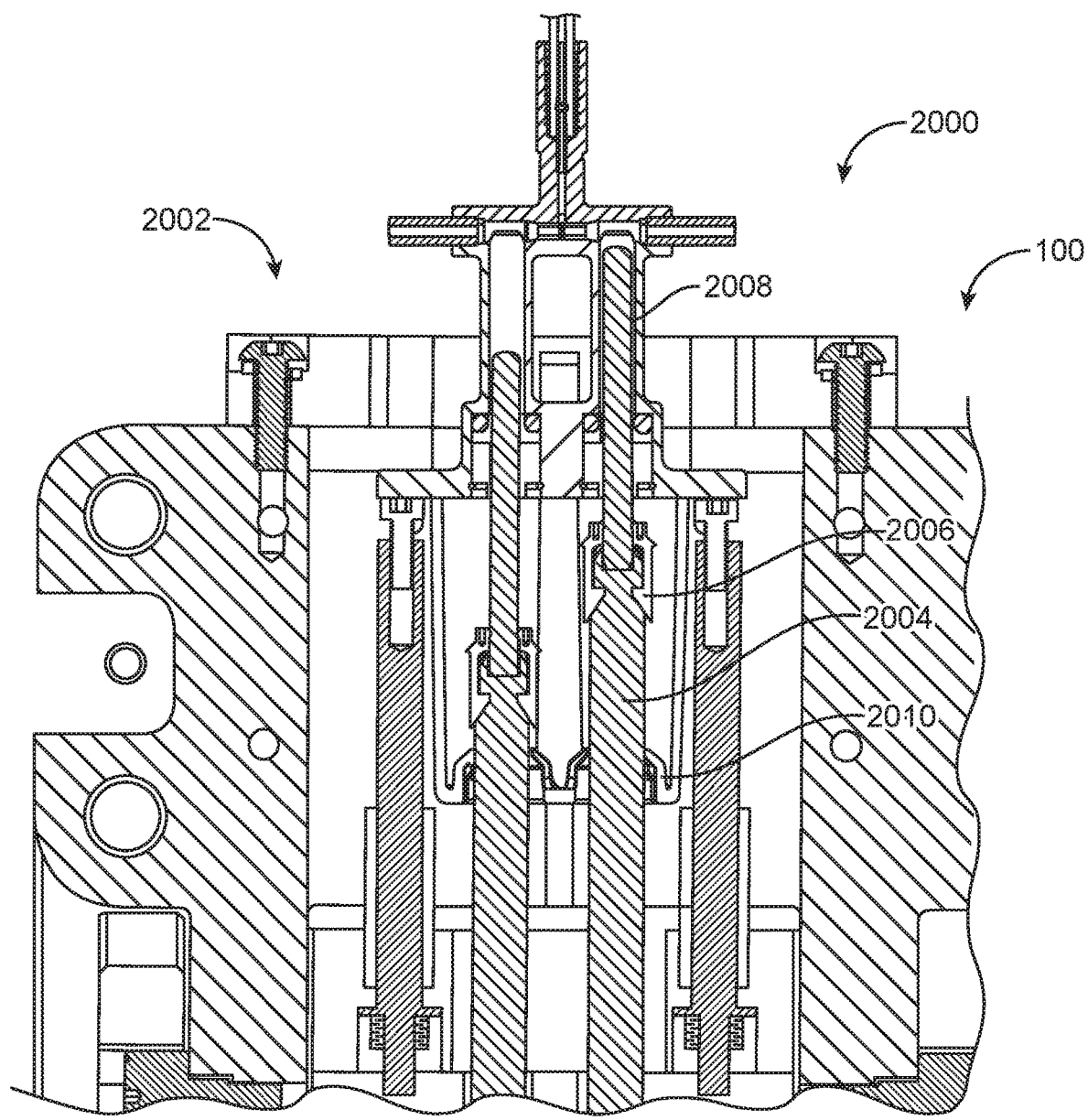
FIG. 22 shows schematic diagram of a pump cartridge in which dual pistons are engaged with control rods and are in a pumping position, in accordance with some embodiments.

With reference to FIGS. 20, 21, and 22, a loader 2000 is illustrated with a cartridge 2002 installed therein. The loader 2000 facilitates coupling of the cartridge 2002 with the motor by way of a transmission. In some embodiments, the transmission comprises control rods 2004 as has been described, which are driven by a motor.

The process of loading a cartridge begins with installing the cartridge 2002 into the loader 2000, which may be done by manually inserting the cartridge into one or more recesses within the loader 2000 that are configured to securely hold the cartridge 2002. Any suitable type of fastening method may optionally be used to add to the securement of the cartridge in the loader 2000, such as fasteners, levers, or locks, to name a few. FIG. 20 illustrates a cartridge 2002 initially installed into the loader 2000, and as can be seen, the control rods 2004 are not engaged with the engagement structure 2006 or the pistons 2008.

FIG. 21 illustrates a first action of engaging the control rods 2004 with the pistons 2008. The loader 2000 facilitates relative displacement between the cartridge 2002 and the control rods 2004. In some embodiments, the control rods 2005 are advanced toward the cartridge 2002, such as by a lever, motor, cam, or some other actuator. In other embodiments, the cartridge 2002 is advanced toward the control rods 2004, such as by manual force, a lever, motor, or cam. In any event, a linear force causes relative motion between the cartridge 2002 and the control rods 2004 until the control rods 2004 contact the engagement structures 2006. A first force causes the control rods 2004 to engage with the engagement structures 2006, and the components may be considered to "snap" together as the engagement structure 2006 elastically deforms and quickly returns to its initial shape once the control rod 2004 is inserted sufficiently to mate the cooperating structures.

Once the control rods 2004 are "snapped" into the engagement structures 2006 as illustrated in FIG. 21, a second axial force causes the engagement structure 2006 to disengage from the retention structure 2010 as shown in FIG. 22. In this configuration, the pistons 2008 are now liberated from their fixed position and are free to slide within the channels in response to linear force from the control rods 2004.

In the configuration shown in FIG. 22, one piston 2008 is advanced to its top dead center position, the opposing piston is at its bottom dead center position, and the system is ready to begin pumping working fluid as has been previously described.

The loader 2000 may comprise structure that is part of a larger console, and is especially suited to receive a cartridge 2002 and further is configured to facilitate mating cartridge 2002 with the transmission and the motor.

Figure 23:
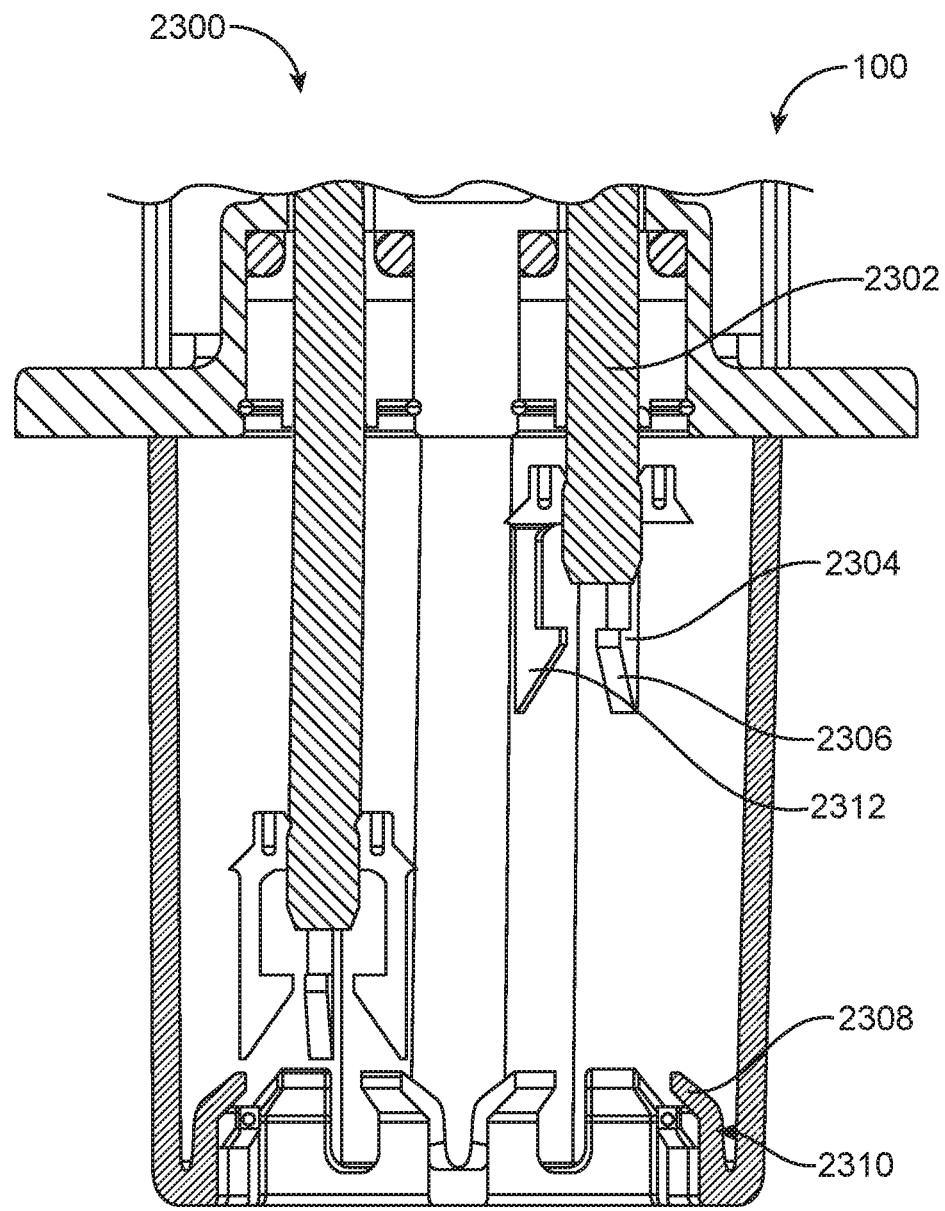
FIG. 23 shows a schematic diagram of a valve body usable in a pump cartridge once the pump cartridge has been disengaged from the pump, in accordance with some embodiments.

FIG. 23 shows a cartridge 2300 after it has been in operation and has since been removed from the loader. The piston 2302 is still coupled to the engagement structure 2304; however, the engagement structure has been uncoupled from the control rod (not shown). A cartridge will have a useful life, which may be based upon hours of operation, number of procedures, date of in-service, or some other metric. A cartridge may be removed from the loader and replaced with a new cartridge. In this way, the cartridge is a consumable item, while the remaining components of the pump, including the control rods, motor, loader, and console are durable components and are not typically replaced.

To remove the cartridge 2300, the control rod is withdrawn from the cartridge 2300. During the operation, a sloped surface 2306 on the engagement structure contacts a mating surface 2308 on the retention structure 2310. An applied force from the control rod causes the retention structure to interfere with further withdrawal of the engagement structure 2304 and causes the engagement structure to deform outwardly, thus releasing the protrusions 2312 from their purchase within the grooves of the control rod. The control rod is then able to be completely decoupled from the engagement structure 2304 and removed from the cartridge.

As can be seen, the engagement structure 2304 remains attached to the piston 2302, and is unable to be withdrawn from the cartridge 2300 because the retention structure 2310 prohibits its withdrawal. This also provides the additional feature that it becomes very difficult to re-use a cartridge 2300 that has exceeded its useful life, and a simple visual check can verify whether the cartridge 2300 has been previously used.

Active Piston Return and Cartridge Loading

Figure 24A:
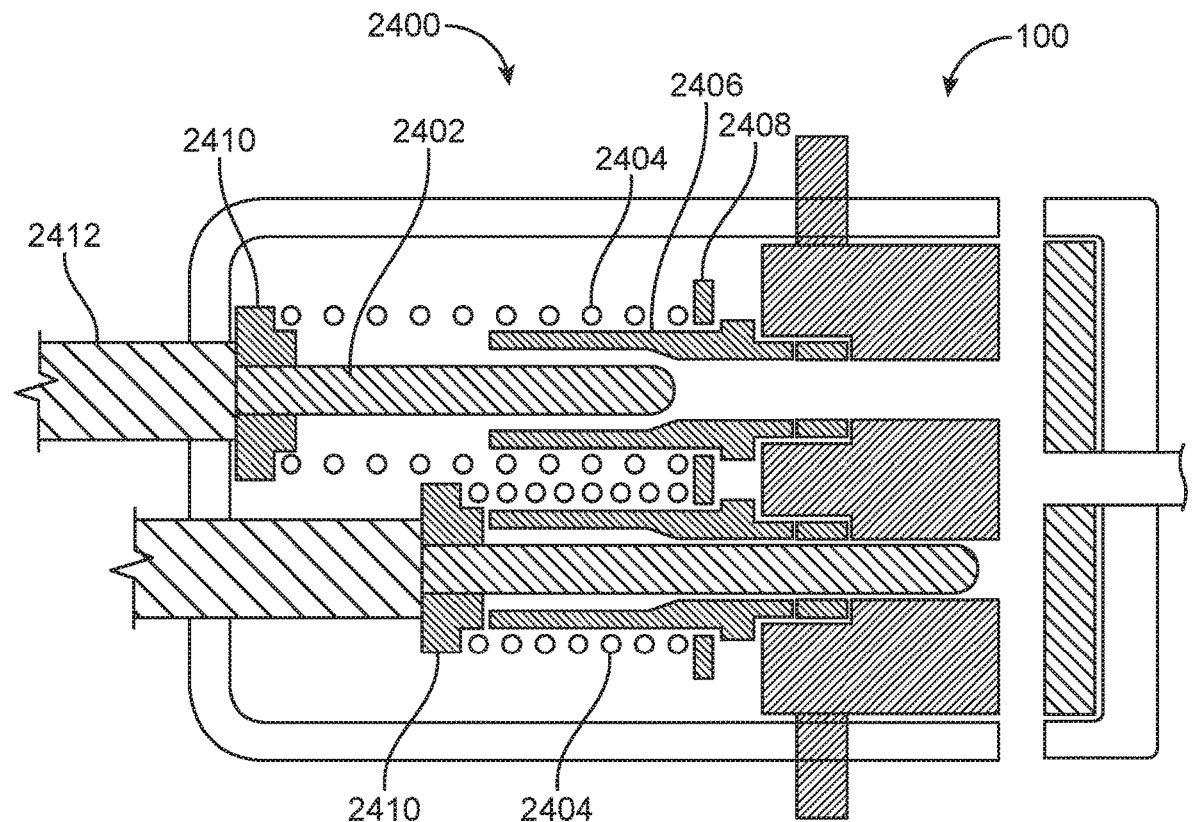
FIG. 24A shows a schematic diagram of a top view of a pump cartridge having dual pistons and a piston return spring, in accordance with some embodiments.
Figure 24B:
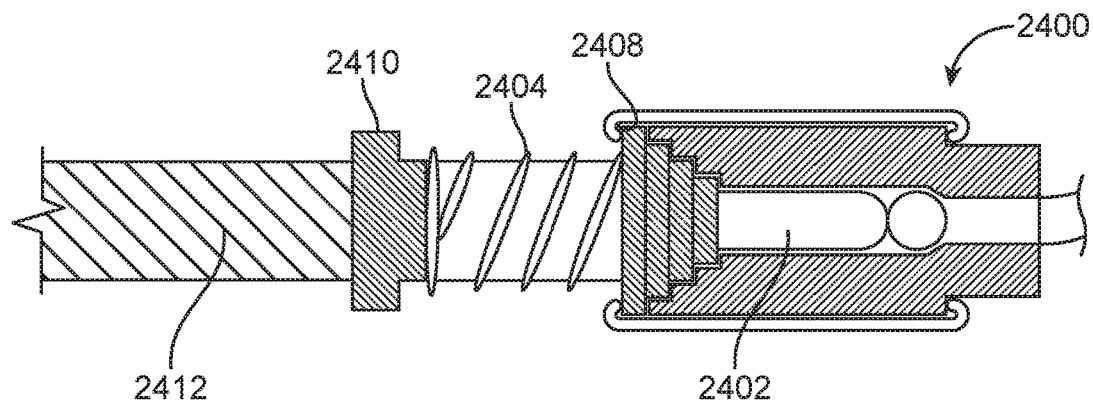
FIG. 24B shows a schematic diagram of a side view of a pump cartridge having dual pistons and a piston return spring, in accordance with some embodiments.

FIG. 24A and FIG. 24B illustrate a cartridge 2400 having an active return on the piston. The piston 2402 may be as substantially described elsewhere herein, and has a compression spring 2404 that surrounds a bushing 2406 that guides the piston 2402 through its stroke. The bushing 2406 may carry a forward retainer 2408 that provides a bearing surface against which the spring 2404 is compressible. A rear retainer 2410 may be carried by either the piston 2402 or the control rod 2412 and provides a surface that engages the spring and provides a compressive force on the spring 2404 as the control rod 2412 is advanced into the cartridge 2400. Providing the rear retainer 2410 on the piston 2402 allows the control rod 2412 to be completely withdrawn from the cartridge 2400, as desired. The spring 2404 may be selected to have a desired spring constant, and may be selected to prevent "slapping" between the control rod 2412 and the rear retainer 2410, especially at higher motor rpms.

In some embodiments, the spring 2404 provides an amount of force to the piston within a range from about 1 pound to about 20 pounds between bottom dead center and top dead center of the piston in the cylinder. The amount of force may optionally be within the range from about 2 to 15 pounds, or from about 5 to 10 pounds.

The pushrod may carry a slider 2410 that compresses the spring with advancement of the pushrod and piston, the slider coupled to a receiver to receive the piston and urge the piston toward the pushrod with retraction of the pushrod.

The control rod 2412 may be configured such that it provides surface contact with the piston 2402 and may not necessarily include structure that captures the piston and secures the two together. In other words, the control rod 2412 may function strictly to push the piston 2402 and not provide a force to return the piston 2402. The return force required to retract the piston to its bottom dead center position may be provided, in large part, by the spring 2404. The rear retainer 2410 may optionally engage with, and perhaps capture, the piston 2402, but is not required to do so where there is an external force applied to the piston 2402 to cause it to move from its top dead center to its bottom dead center locations.

The seals for inhibiting fluid leaks from the cartridge may be any suitable seal mechanism and arrangement, several of which have already been described.

Figure 25A:
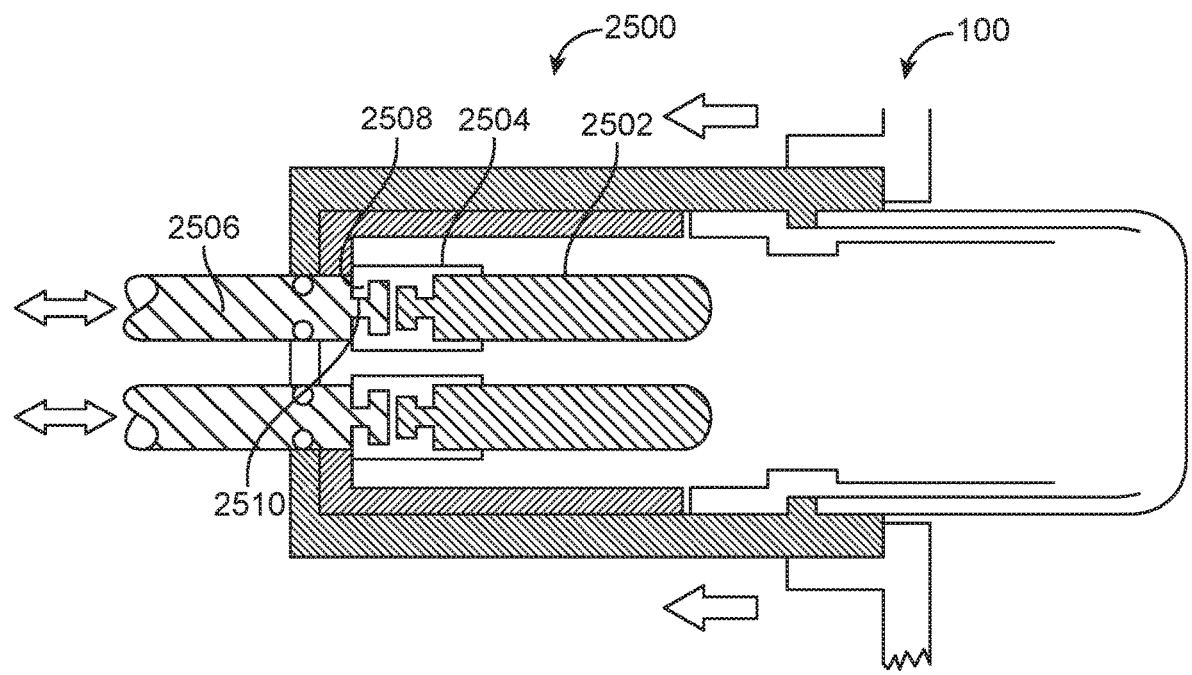
FIGS. 25A and 25B illustrate a cartridge having a piston carrying an engagement cap, in accordance with some embodiments.
Figure 25B:
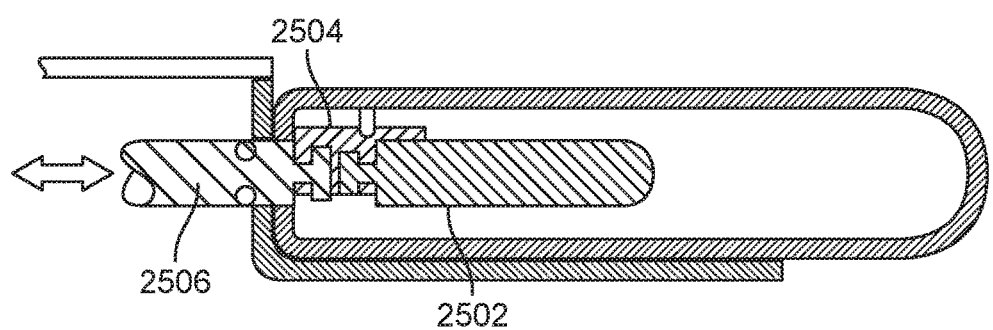

FIGS. 25A and 25B illustrate a cartridge 2500 having a piston 2502 carrying an engagement cap 2504. The engagement cap 2504 may be designed to cooperate with the control rod 2506 to provide a secure connection therebetween. In some embodiments, the engagement cap 2504 has a radial ridge 2508 that engages a radial groove 2510 formed in the control rod 2506. The engagement cap 2504 may be secured to the piston 2502 by any suitable method, and may be attached to the piston 2502 during manufacture. The engagement cap 2504 may be connected to the control rod 2506 by the application of a force that is transverse to the longitudinal axis of the control rod 2506. In other words, the cartridge can be forced downwardly onto the control rods to secure the pistons 2502 and the control rods 2506 together. The cartridge 2500 may be manually inserted into the loader such as by pressing downward on the cartridge to couple the pistons 2502 to the control rods 2506. The cartridge may alternatively be coupled to the loader by a motor, lever, hinge, crank, or some other manual or automated means.

Figure 26A:
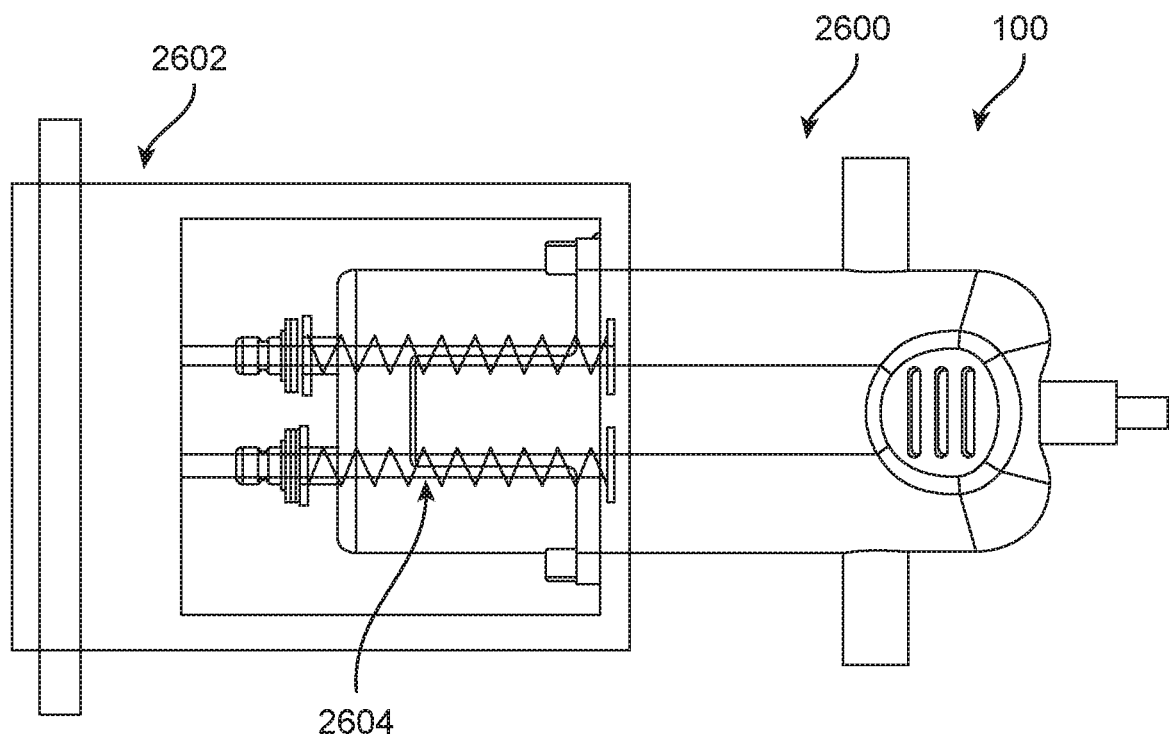
FIGS. 26A and 26B show a schematic diagram of a pump cartridge having a yoke with linear travel and a piston return spring, in accordance with some embodiments.
Figure 26B:
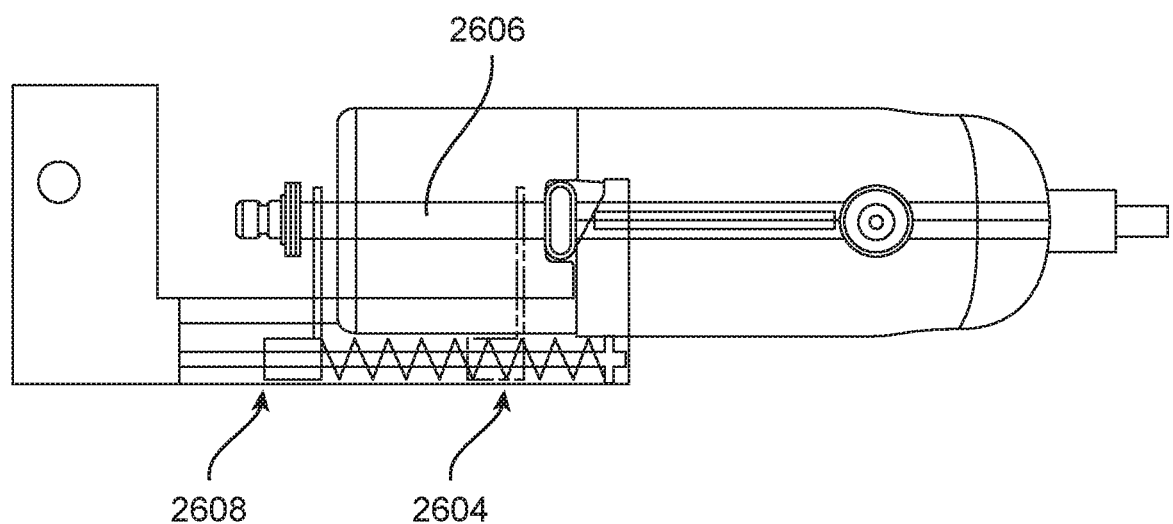

FIGS. 26A and 26B illustrate a cartridge 2600 coupled to a loader 2602. The loader 2602 may contain a yoke 2604 that connects the control rods 2606 to an actuator 2608 that causes the control rods 2606 to reciprocate at a desired stroke and frequency. The actuator 2608 may be a rotary or linear travel actuator. As a non-limiting example, the actuator 2608 may comprise a pinion gear having gear teeth and the control rod 2606 (or the piston itself) may be formed with rack gear threads that engage with the pinion gear teeth to form a rack and pinion gear system. As the pinion gear is rotated clockwise and counterclockwise in rapid succession, the control rod 2606 is caused to reciprocate linearly.

The actuator 2608 may alternatively comprise a lead screw or a power screw that converts rotational motion of the motor into linear displacement of the control rods and pistons.

Figure 27:
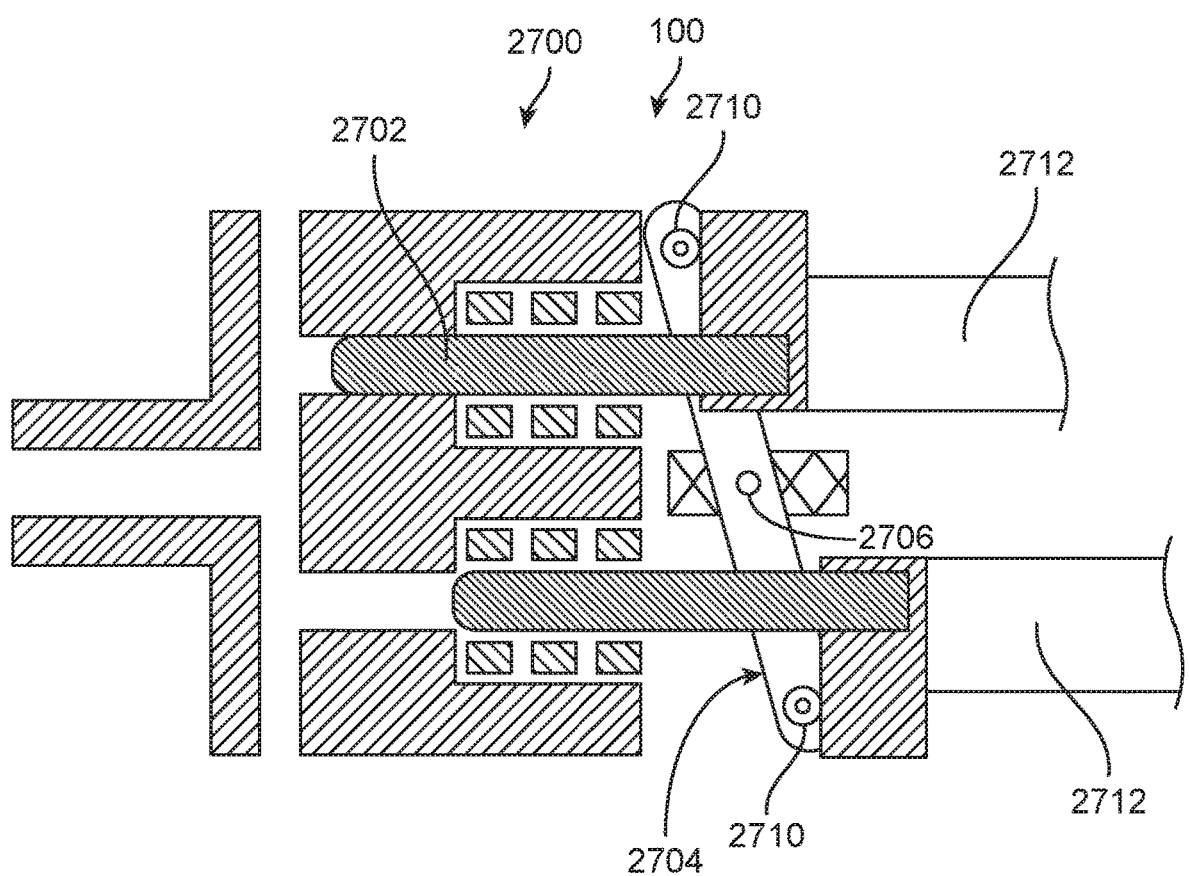
FIG. 27 shows a schematic diagram of a dual-piston pump cartridge with a rocker arm coupling the dual pistons, in accordance with some embodiments.

FIG. 27 illustrates a cartridge 2700 having a dual piston arrangement as previously described. The pistons 2702 may be coupled by a rocker arm 2704 having a pivot point 2706 disposed generally in between the pistons 2702. The rocker arm 2704 may have protruding bosses 2710. One control rod 2712 may push against the boss 2710 of the rocker arm 2704 causing the rocker arm 2704 to pivot about the pivot point 2706. As one control rod 2712 exerts a force on a boss 2710 to drive the piston 2702 distally within the cylinder, the opposing boss 2710 causes the opposing piston to withdraw from the cylinder. Thus, the primary force that tends to withdraw the piston is applied by the control rod driving the opposing piston 2702 and the withdrawing force is applied through the rocker arm 2704.

The cartridge 2700 may be loaded into the console by dropping the cartridge 2700 vertically downward into the console and engaging with suitable retaining structures of the console to secure the cartridge 2700.

Figure 28:
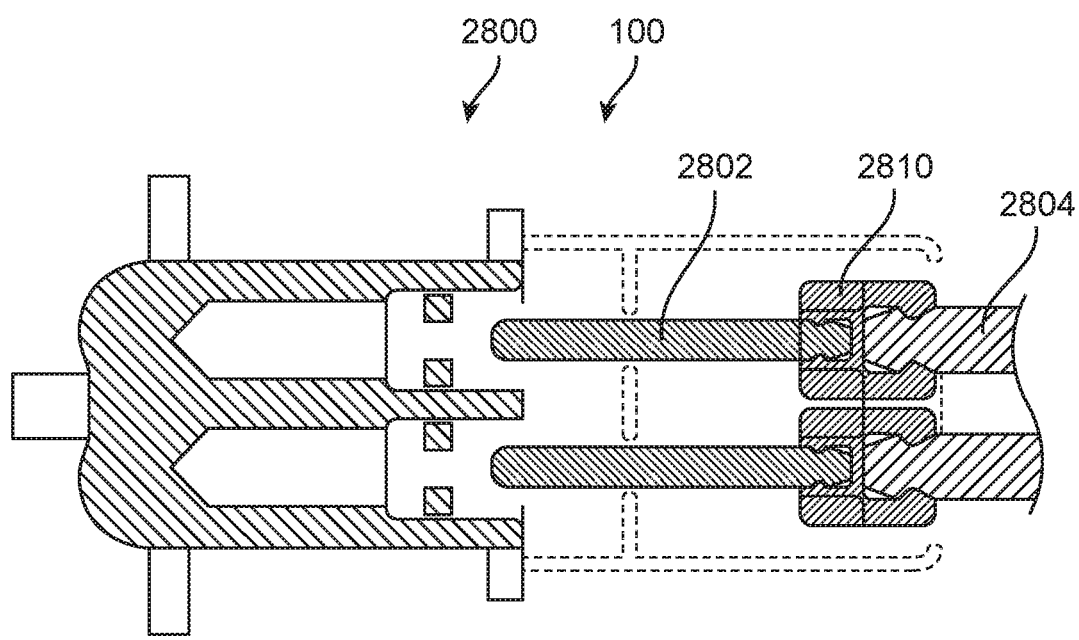
FIG. 28 shows a schematic diagram of a coupling member for connecting one or more pistons of a pump cartridge with associated controls rods, in accordance with some embodiments.

FIG. 28 illustrates a cartridge 2800 having one or more pistons 2802 and one or more control rods 2804. The pistons 2802 are coupled to the control rods 2804 by an engagement structure 2810. The engagement structure 2810 may securely be affixed to the piston 2802 and control rod 2804 through structure that captures an end of each respective rod. After use, the engagement structure 2810 may be removed from the control rod 2804 through an axial force that pulls the end of the control rod 2804 out of the engagement structure 2810.

Axial Cartridge Loading

Figure 29:
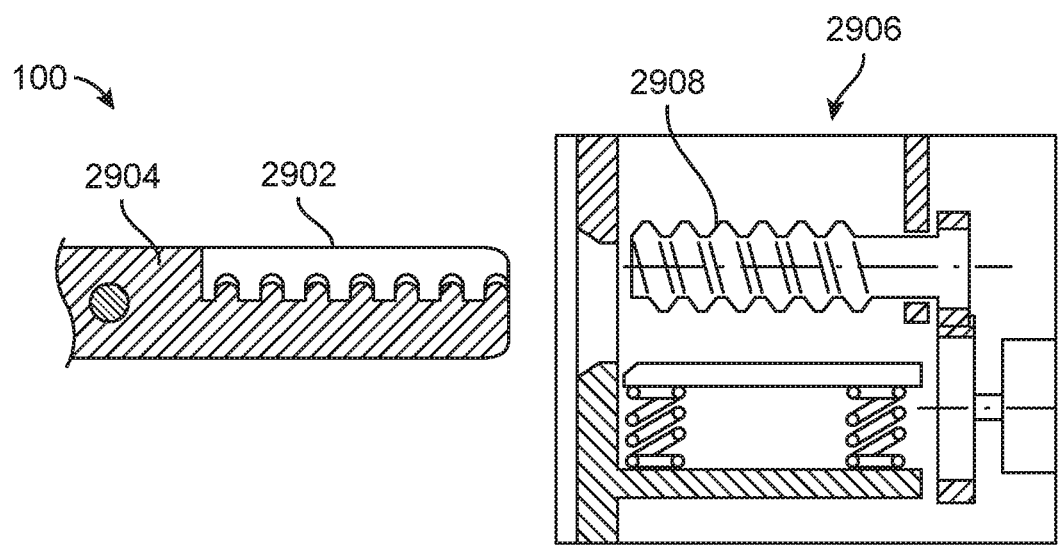
FIG. 29 shows a schematic diagram of a rotating screw draw in for coupling a pump cartridge with a pump, in accordance with some embodiments.

FIG. 29 illustrates structure configured for axial loading of the cartridge. The cartridge may have threads 2902 formed on a shaft 2904 thereof. The loader 2906 may likewise have drawing threads 2908 that engage with the cartridge threads 2902 to draw the cartridge into the loader 2906. In some embodiments, the cooperating threads may be acme threads, which resist driving in a reverse direction, thereby providing positive retention of the cartridge in the loader.

Figure 30:
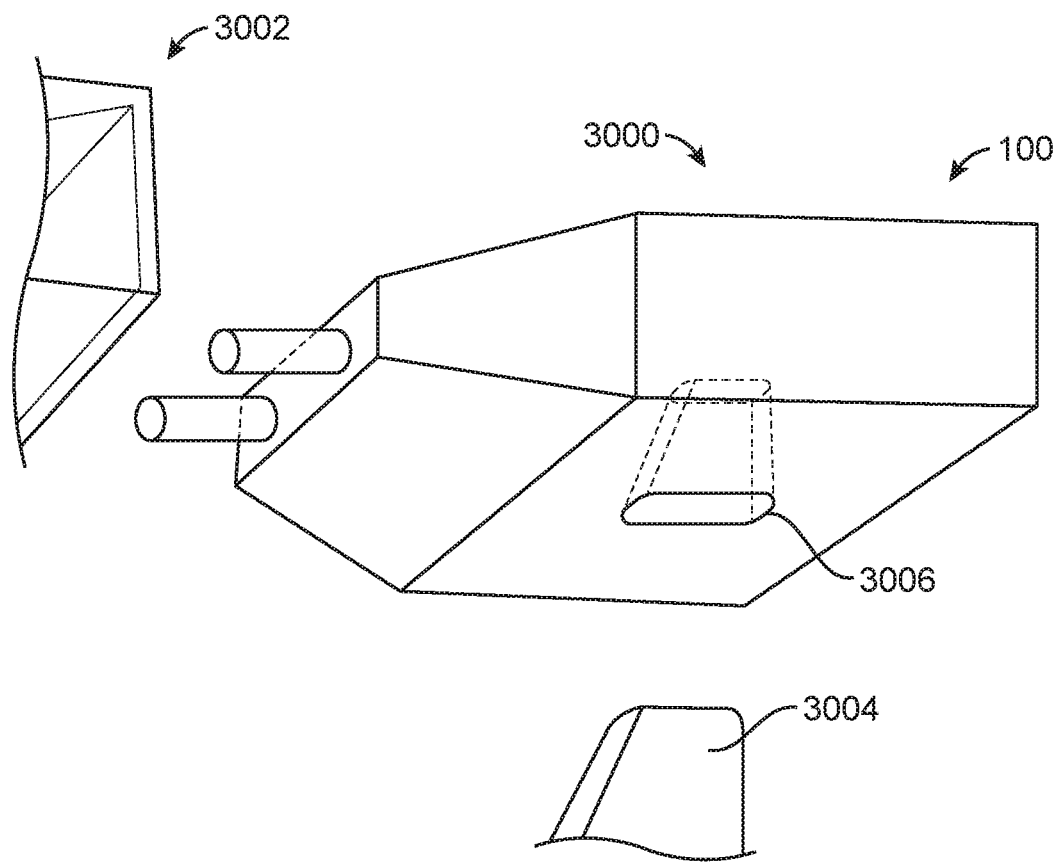
FIG. 30 shows a schematic diagram of a pump cartridge configured with a tapered pocket for coupling and drawing into a pump housing, in accordance with some embodiments.

FIG. 30 illustrates a cartridge 3000 and an attachment mechanism to secure the cartridge 3000 in a loader 3002. In the illustrated embodiments, a tapered wedge 3004 seats within a correspondingly shaped pocket 3006 formed in the cartridge 3000. The tapered wedge 3004 may be associated with the console and may move relative to the cartridge 3000 to insert into the pocket 3006 and thereafter draw the cartridge 3000 into engagement with the loader 3002.

Figure 31:
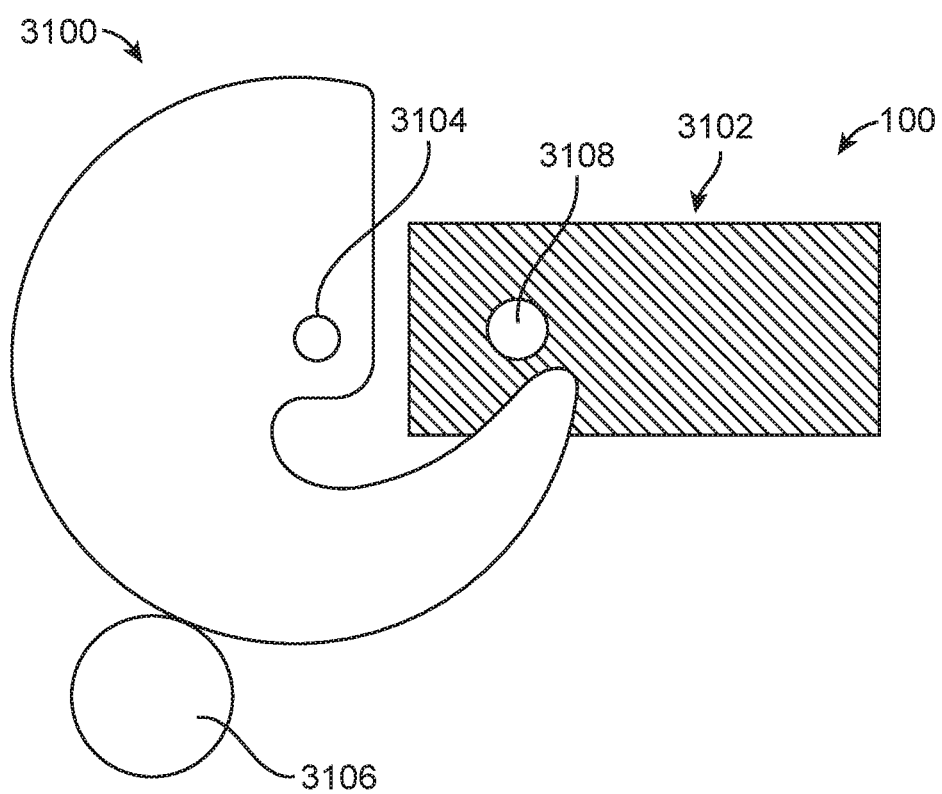
FIG. 31 shows a schematic diagram of a cam configured to engage with a boss on a pump cartridge and draw the cartridge into the pump housing, in accordance with some embodiments.

FIG. 31 illustrates a cam 3100 configured to draw a cartridge 3102 into a loader. The cam 3100 has a pivot 3104 about which the cam 3100 rotates. An outer surface of the cam 3100 may have threads formed therein and a motor 3106 may turn a gear that meshes with the threads formed on the cam. The cartridge 3102 may have one or more protrusions 3108 extending therefrom that can be captured by the cam. As the motor 3106 turns the cam 3100, the cam 3100 captures the protrusion 3108 and pulls the cartridge 3102 substantially linearly to secure the cartridge 3102 relative to the loader.

Vertical Top Down Cartridge Loading

Figure 32:
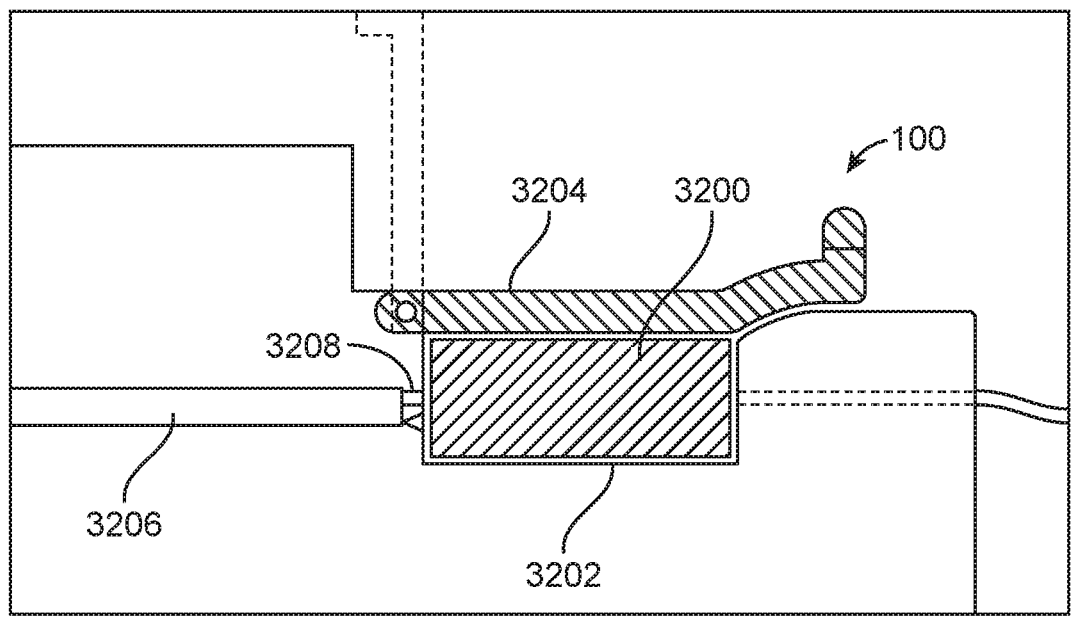
FIG. 32 shows a schematic diagram of a pump cartridge nestled in a recess in the pump housing and secured by a biasing lever, in accordance with some embodiments.

FIG. 32 illustrates a mechanism for loading a cartridge 3200. The cartridge 3200 may be placed within a receptacle 3202 configured to receive and hold the cartridge 3200. A lever 3204 is moveable between a first position in which the receptacle 3202 is uncovered and open to receiving the cartridge, and a second position in which the lever 3204 fastens and holds the cartridge 3200 in place within the receptacle 3202. Once in place, the control rods 3206 can advance and engage the pistons 3208 associated with the cartridge 3200.

Figure 33:
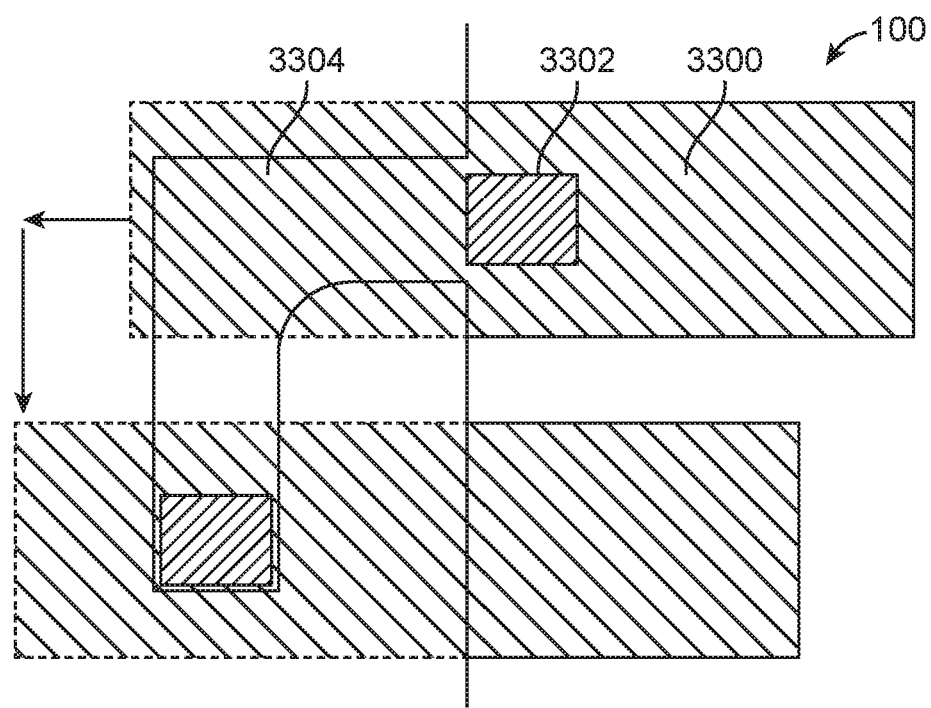
FIG. 33 shows a schematic diagram of a channel formed in a pump housing and a cooperating boss on a pump cartridge to facilitate loading the cartridge into the pump housing, in accordance with some embodiments.

FIG. 33 illustrates a mounting path for engaging a cartridge 3300 with a loader associated with a console. The cartridge 3300 may have protruding bosses 3302 that slide within a channel 3304 formed within the loader. The channel 3304 may define any suitable path, such as the one illustrated in which the cartridge 3300 travels inward and then downward as it engages with the loader. Of course, other paths may be used with this concept.

Figure 34:
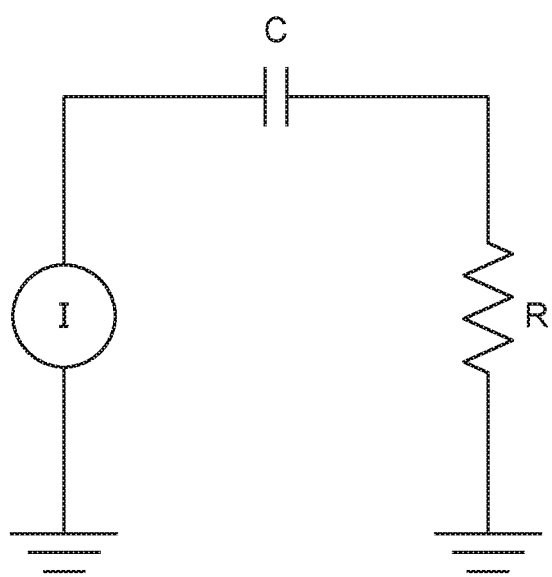
FIG. 34 shows an equivalent circuit suitable for incorporation in accordance with some embodiments.

FIG. 34 shows an equivalent circuit suitable for incorporation in accordance with some embodiments. With some applications such as surgery, the pump is connected to a nozzle with a fluid line. The pump comprises a source of fluid injection similar to the source of current I of an electrical circuit. The flow line can be configured to expand in response to pressure similar to capacitance C of a capacitor. Increasing the length of the flow line can increase the capacitance and decreasing the length of the flow line can decrease the capacitance. The nozzle may comprise a small opening providing a resistance to flow similar to a resistor R. Decreasing a diameter of the nozzle can increase the resistance and increasing the diameter of the flow line and decrease the resistance. The combination of the pump fluid injection current, fluid line capacitance and nozzle resistance can be configured to smooth out the flow from the pump so as to provide more uniform fluid flow through the nozzle. Based on the teachings disclosed herein, a person or ordinary skill in the art can determine the pump flow fluid injection, line capacitance, and nozzle resistance to provide improved stability of the flow of fluid such as a liquid from the end of the nozzle. Work in relation to embodiments disclosed herein suggests that a more uniform flow rate through the nozzle can provide improve smoothness to ablations such as tissue resection, for example.

In some embodiments, the positive displacement pump as described herein provides an amount of fluid that can vary with flow rate and pressure, and variables such as piston seal, valve seal, pressure and valve closure rate can result in a variable fluid flow characteristics that can be measured and incorporated into the fluid flow equivalent circuit. The fluid delivery line may comprise a conduit with compliance that can vary with pressure, and this can be incorporated into the fluid flow equivalent circuit. A cylindrical nozzle may comprise a resistance to flow that varies with flow rate, and this can be measured and incorporated into the fluid flow equivalent circuit. Fluid flow characteristics that can be influence the resistance include boundary flow conditions, the shape of the nozzle, and eddy current flow near the nozzle, which can increase the resistance at higher flow rates.

Figure 35:
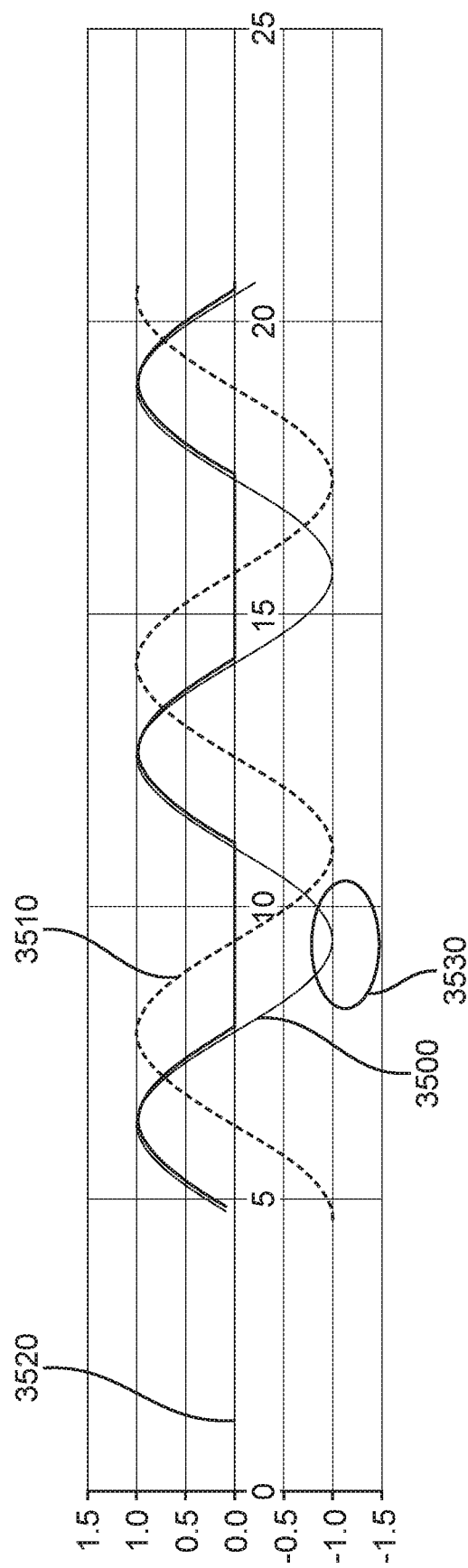
FIG. 35 shows a pump displacement suitable for smoothing in accordance with some embodiments.

FIG. 35 shows a pump displacement suitable for smoothing in accordance with some embodiments. The sinusoidal motion of the crankshaft 3500 can impart motion to the piston. Motion of the piston can be represented with a filling curve cosine function 3510. The filling curve cosine function 3510 shows the fluid outflow from the cylinder. Portions of the filling curve cosine function 3510 are shown above and below zero, corresponding to filling and emptying of the cylinder. The X-axis 3520 indicates flow past the output valve, with a value of zero indicating zero flow. Near the bottom 3530 of the filling curve indicates a point at which the piston changes direction, which results in inefficiency in the pumping cycle.

Figure 36:
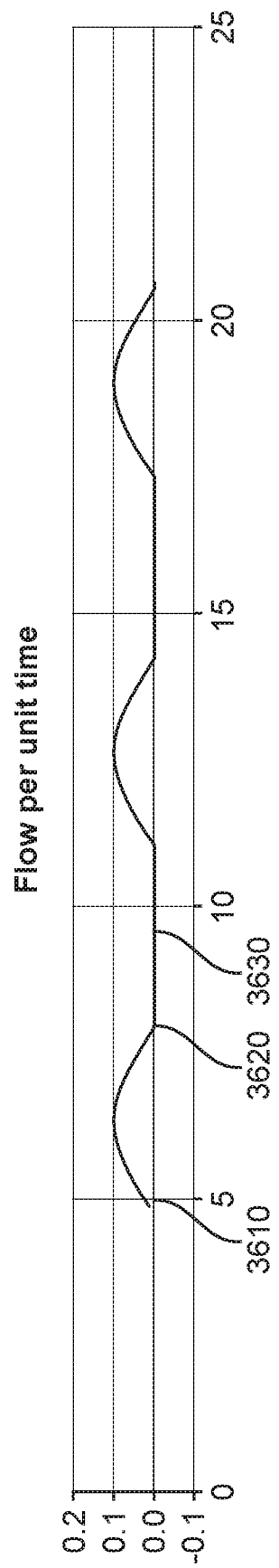
FIG. 36 shows flow per unit time suitable for smoothing in accordance with some embodiments.

FIG. 36 shows flow per unit time suitable for smoothing in accordance with some embodiments. At about t=5 3610, the piston starts moving in a direction to pump fluid out of the outlet. During initial pumping, the piston moves to express fluid from the outlet, and the pressure of the fluid increases to overcome internal resistance and fluid begins to flow through the outlet. As the piston nears the extent of its travel at about t=8 3620, the flow rate out of the outlet slows and eventually becomes zero as the piston reverses direction and begins a filling cycle 3630 of the cylinder. As the piston reciprocates, the fluid flow out of the nozzle approximates the curve shown in FIG. 36.

Figure 37:
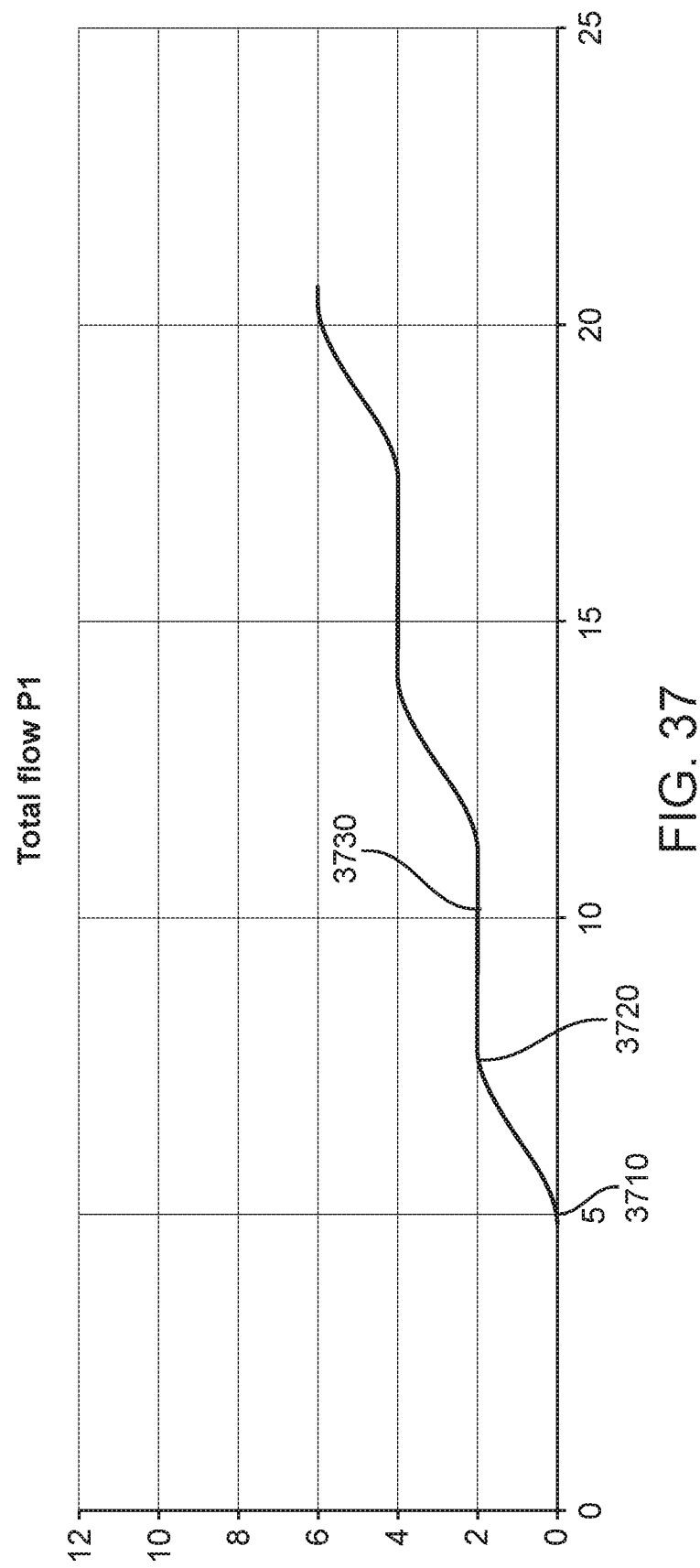
FIG. 37 shows cumulative flow suitable for smoothing in accordance with some embodiments.

FIG. 37 shows cumulative flow suitable for smoothing in accordance with some embodiments. At t=5 3710, the piston begins pumping fluid through the output valve, and fluid is pumped through the output valve through the pumping cycle of the piston. At about t=8 3720, the piston slows its travel, comes to a momentary stop, and reverses direction. This is represented in the graph by the slope of the curve gradually moving to zero 3730, indicating that no fluid is being pumped through the output valve. The region of zero slope corresponds to a filling cycle of the cylinder as the piston withdraws, thus filling the cylinder with fluid. The volumetric output data shown in FIG. 37 provides the material input to a resistance x capacitance equation resulting in pressure and jet velocity.

Figure 38:
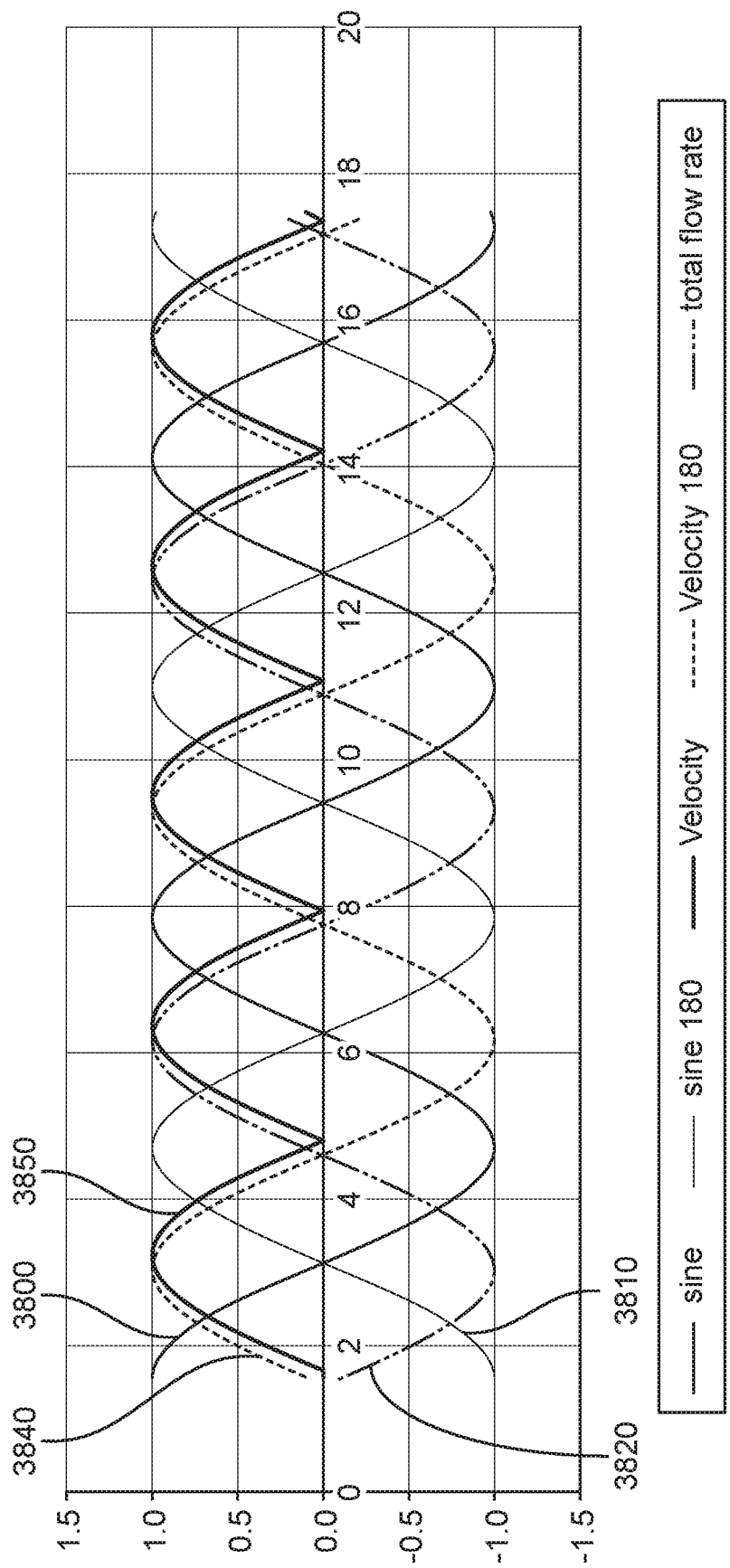
FIG. 38 shows displacement and flow from a dual cylinder pump, suitable for smoothing in accordance with some embodiments.

FIG. 38 shows displacement and flow from a dual cylinder pump, suitable for smoothing in accordance with some embodiments. The dual cylinder pump can provide fluid flow to the line more regularly, so as to decrease variations in fluid flow. For example, a dual cylinder pump can provide dual cylinders and pistons that operate out of phase with one another, such as by oscillating 180° out of phase with one another, with one cylinder executing a pumping cycle while the other cylinder executes a filling cycle.

A first cylinder/piston can be approximated by a sine wave 3800 and a second cylinder/piston can be approximated by a sine 180 wave 3810 (e.g. a sine wave that is 180° out of phase with the sine wave 3800). A velocity 3820 of the first cylinder/piston is approximated by a curve that is out of phase with the sine wave 3800. Similarly, a velocity 180 of the second cylinder/piston can be represented by a curve 3840 that is out of phase with the sine 180 wave 3810. Notably, the velocity curve 3820 and the velocity 180 curve 3840 are 180° out of phase with each other, with one curve having a maximum when the second curve is at a minimum. The net result is a total flow rate 3850 that does not drop below zero. While the total flow rate 3850 through the output valve may be pulsatile, it is much smoother than a single piston configuration.

Figure 39:
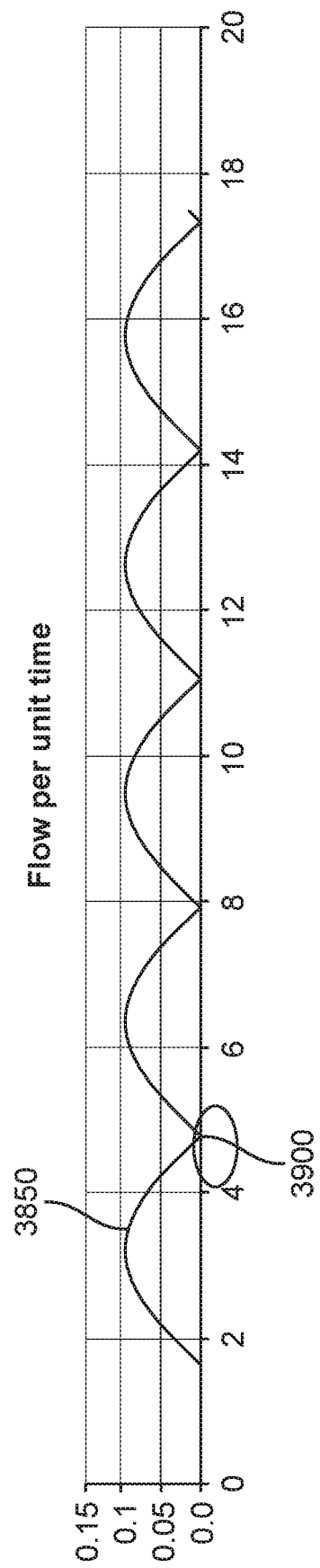
FIG. 39 shows flow from a dual cylinder pump suitable for smoothing in accordance with some embodiments.

FIG. 39 shows flow from a dual cylinder pump suitable for smoothing in accordance with some embodiments. The total flow rate 3850 of a dual cylinder pump remains positive, except for a brief time 3900 where the flow rate from both cylinders cross at a flow rate of 0. In some embodiments, fluid lines downstream of the fluid output valve may have some capacitance built into them, such that even where the pump is producing zero flow through the output valve, the compliance within the fluid lines provides continuous fluid flow, thus further smoothing the total fluid flow.

Figure 40:
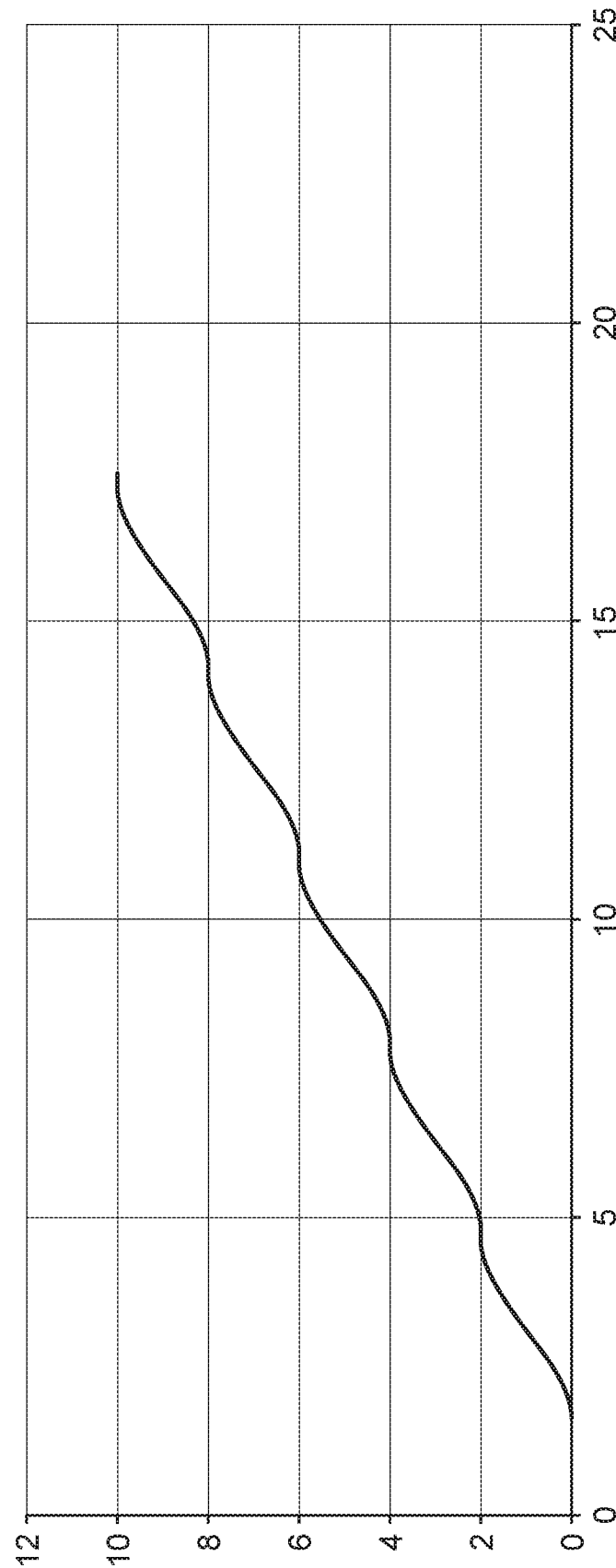
FIG. 40 shows cumulative flow from a dual cylinder pump suitable for smoothing in accordance with some embodiments.

FIG. 40 shows cumulative flow from a dual cylinder pump suitable for smoothing in accordance with some embodiments. As illustrated, the total fluid flow through the output valve continues to rise as a dual cylinder pump operates. The dual cylinder configuration provides for a much smoother fluid flow in comparison with the single cylinder configuration as in FIG. 37. The volumetric output data is the material input to a resistance x capacitance equation resulting in pressure and jet velocity.

Figure 41:
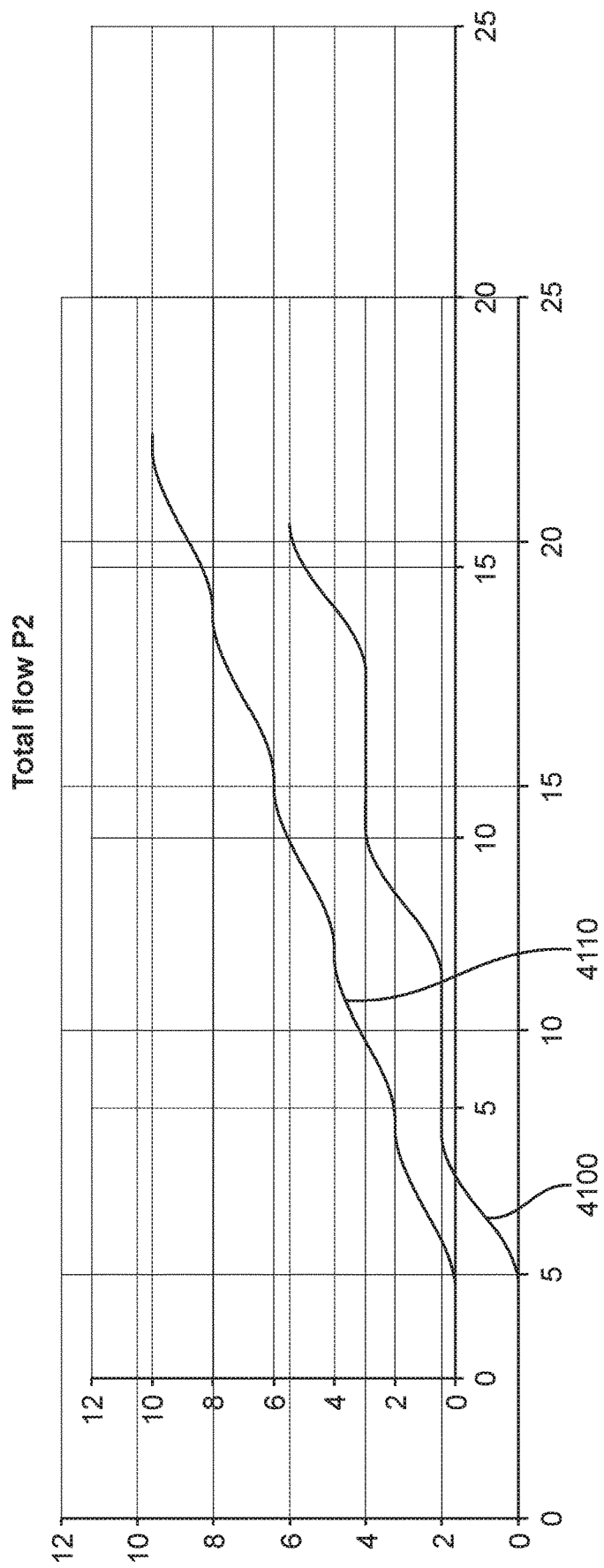
FIG. 41 shows cumulative flow from a dual cylinder pump suitable for smoothing in accordance with some embodiments.

FIG. 41 shows cumulative flow from a dual cylinder pump suitable for smoothing in accordance with some embodiments. A single cylinder pump total flow curve 4100 is illustrated in comparison with a dual cylinder pump total flow curve 4110. As can be seen, the single cylinder pump total flow curve 4100 exhibits periods of no flow due to the cylinder fill cycle, while the dual cylinder pump total flow curve 4110 exhibits nearly continuous fluid flow, a much greater total flow per unit time, and a much smoother fluid delivery.

FIG. 42A shows a fluid pressure profile over time of a single piston pump operating at 20 Hz. In a fluid circuit comprising an at least partially compliant delivery hose and a jet nozzle that provides a restriction on the outgoing fluid, the pressure accumulates and dissipates during the reciprocating piston cycles. The fluid delivery profile curve 4202 shows that during piston retraction when the cylinder is being refilled with fluid, the output valve is closed thus isolating the cylinder from the downstream fluid circuit. The fluid pressure curve 4204 oscillates in response to the pumping action and is smoothed by the compliant delivery hose and the restrictive nature of the jet.

FIG. 42B shows a fluid pressure profile over time of a dual piston pump operating at 20 Hz. The fluid delivery profile curve 4206 shows that two pistons operating 180 degrees out of phase results in a smoother fluid delivery pressure curve 4208. In other words, the amplitude (e.g., variance in output fluid pressure) is much lower for the dual piston pump as compared to the single piston pump, thus indicating a smoother fluid delivery output.

FIG. 42C shows a fluid pressure profile over time of a single piston pump operating at 10 Hz. The fluid delivery profile curve 4210, having a much lower frequency as compared to the single piston pump operating at 20 Hz of FIG. 42A, exhibits a much longer period. The fluid delivery pressure curve 4212 illustrates that the single piston pump, when pumped at a frequency, generates an oscillating fluid delivery pressure.

In some embodiments, tissue or other material has an ablation threshold. This threshold for ablative resection can be dependent on the type of tissue. For example, collagenous tissue such as the capsule of the prostate may have a higher ablation threshold than the glandular tissue of the prostate. The threshold for ablative resection is related, at least in part, to the tensile strength and elasticity of the tissue being ablated. Tissue will typically have an ablation threshold, which defines a fluid pressure that, when exceeding the ablation threshold, will ablate the tissue, and when the fluid pressure is below the ablation threshold, will not ablate tissue. In some instances, as shown in FIG. 42C, the fluid delivery pressure curve 4212 may fall below the ablation threshold.

In contrast, in FIG. 42D the fluid delivery pressure profile curve 4230 illustrates a dual piston pump operating at 10 Hz, and further shows that the fluid delivery pressure curve 4232 does not drop below the ablation threshold 4240 upon reaching steady state for a similar flow rate. The ablation threshold 4240 may be different for various types of tissue and the pump can be configured based upon the type of tissue to be ablated. For instance, the pump can be run at a higher frequency, which results in an average fluid pressure delivery that is greater than the pump running at a lower frequency. Comparing the dual piston pump operating at 10 Hz and 20 Hz, it can be seen that the 20 hz fluid delivery pressure curve 4208 is much higher on average than the 10 Hz fluid delivery curve 4232.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, a logic circuit, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

As used herein, the term "or" is used inclusively to refer items in the alternative and in combination.

The present disclosure also includes the following numbered clauses.

Clause 1. A pump cartridge comprising: a piston; a housing comprising a channel, an inlet, and an outlet, the channel comprising a cylinder shaped to receive the piston; and an engagement structure to couple the piston to a pushrod in response to axial movement of the pushrod or the housing.

Clause 2. The pump cartridge of clause 1, further comprising a casing over a portion of the housing, wherein the engagement structure is supported with the casing outside channel.

Clause 3. The pump cartridge of clause 2, wherein the engagement structure is connected to the casing and configured to decouple from the casing with axial advancement of the pushrod.

Clause 4. The pump cartridge of clause 3, wherein the casing comprises an opening to receive the pushrod and wherein the engagement structure extends through the opening from an interior of the casing to an exterior of the casing.

Clause 5. The pump cartridge of clause 4, wherein an exterior portion of the engagement structure is configured to advance through the opening and into the interior of the casing when coupled to the pushrod.

Clause 6. The pump cartridge of clause 5, wherein the exterior portion of the engagement structure is configured to remain within the interior of the casing when decoupled from the pushrod.

Clause 7. The pump cartridge of clause 2, further comprising a retention structure connected to the casing to retain the engagement structure in a shipping configuration and to decouple from the engagement structure in response to axial force from the pushrod.

Clause 8. The pump cartridge of clause 7, wherein the retention structure comprises a plurality of inclined tabs configured to deflect upon axial advancement of the engagement structure toward an interior of the casing and to remove the engagement structure from the pushrod upon retraction of the pushrod from the interior.

Clause 9. The pump cartridge of clause 2, wherein the piston is connected to the engagement structure and the engagement structure is connected to the casing in a storage configuration with the piston outside the cylinder in order to permit sterilization gas to flow from an interior of the casing into the cylinder and wherein the casing comprising an opening to allow the sterilization gas to flow from an exterior of the casing to the interior of the casing and into the cylinder and optionally wherein a distal tip of the piston is located outside the cylinder and within the channel.

Clause 10. The pump cartridge of clause 1, wherein the engagement structure is configured to couple to the pushrod with a first amount of axial force and to decouple from the pushrod with a second amount of axial force greater than the first amount of force.

Clause 11. The pump cartridge of clause 10, wherein the first amount of axial force is oriented in a first direction and the second amount of axial force is oriented in a second direction and optionally wherein the first direction is opposite the second direction.

Clause 12. The pump cartridge of clause 1, wherein the engagement structure is configured to deform upon decoupling from the pushrod.

Clause 13. The pump cartridge of clause 1, further comprising a support coupled to the housing and the engagement structure, wherein the support is configured to decouple from the engagement structure in response to the axial movement of the pushrod or the housing and optionally wherein the support comprises a casing.

Clause 14. The pump cartridge of clause 13, further comprising a seal located in the channel, wherein the support is configured to retain the engagement structure with the piston positioned in relation to the seal so as to define a gap between at least a portion of the piston and the seal in order to allow a sterilizing gas to enter the cylinder.

Clause 15. The pump cartridge of clause 13, wherein the support is configured to retain the engagement structure with the piston positioned in relation to the cylinder so as to define a gap between at least a portion of the piston and the cylinder in order to allow a sterilizing gas to enter the cylinder.

Clause 16. The pump cartridge of clause 13, further comprising a retention structure coupled to the support, the retention structure configured to retain the engagement structure and release the engagement structure in response to axial advancement of the pushrod.

Clause 17. The pump cartridge of clause 16, wherein the retention structure comprises a plurality of extensions sized and shaped to engage a groove on the engagement structure, the plurality of extensions inclined toward the engagement structure and an inlet of the cylinder in order to allow the engagement structure to move toward the cylinder with axial advancement of the pushrod and to decouple the engagement structure from the pushrod with axial retraction of the pushrod away from the cylinder.

Clause 18. The pump cartridge of clause 17, wherein engagement structure comprises a groove or a flange to receive the plurality of extensions to retain the engagement structure with the retention structure and wherein the plurality of extensions is configured to deflect radially away from the piston to allow advancement of the piston toward the cylinder.

Clause 19. The pump cartridge of clause 16, wherein the engagement structure is configured to engage the pushrod with a first amount of force and the retention structure is configured to decouple from the engagement structure with a second amount of force, the second amount of force greater than the first amount of force.

Clause 20. The pump cartridge of clause 19, wherein the engagement structure is configured to retain coupling between the pushrod and the piston with an amount of force sufficient to draw the piston proximally with reciprocal motion of the piston in the cylinder and the pushrod coupled to the piston and optionally wherein the amount of force to draw the piston proximally is within a range from about 0.25 pounds to about 20 pounds between bottom dead center and top dead center of the piston in the cylinder and optionally wherein the amount is within a range from about 1 to 15 pounds and optionally from about 2 to 10 pounds and optionally wherein said engagement structure is configured to inhibit decoupling of the cylinder from the pushrod with retraction of the pushrod and cylinder within said range.

Clause 21. The pump cartridge of clause 19, further comprising a spring coupled to the piston, wherein the spring is configured to compress with advancement of the pushrod along the cylinder and retain coupling between the pushrod and the piston with an amount of force sufficient to move the piston proximally away from a distal end of the cylinder when the pushrod is drawn proximally away from a valve to provide reciprocal motion of the piston in the cylinder with reciprocal motion of the pushrod.

Clause 22. The pump cartridge of clause 21, wherein the spring comprises one or more of a torsion spring, a coil spring or a leaf spring and optionally wherein the spring provides an amount of force to the piston within a range from about 1 pound to about 20 pounds between bottom dead center and top dead center of the piston in the cylinder and optionally wherein the amount is within a range from about 2 to 15 pounds and optionally from about 5 to 10 pounds.

Clause 23. The pump cartridge of clause 21, wherein the spring comprises a torsion spring coupled to the piston to urge the piston toward the pushrod and optionally wherein a center of rotation of the torsion spring is located away from an elongate axis of the piston.

Clause 24. The pump cartridge of clause 21, wherein the spring comprises a coil spring coupled to the piston to urge the piston toward the pushrod and optionally wherein the piston extends through an elongate axis of the coil spring.

Clause 25. The pump cartridge of clause 16, wherein the retention structure comprises a plurality of channels sized and shaped to pass a plurality of fingers of the engagement structure.

Clause 26. The pump cartridge of clause 25, wherein the retention structure comprises a plurality of extensions shaped to define the plurality of channels and wherein the extensions are inclined to toward the cylinder to allow the plurality of fingers to pass through the plurality of channels.

Clause 27. The pump cartridge of clause 25, wherein the retention structure comprises a transit cap configured to retain the engagement structure and piston for storage and shipping.

Clause 28. The pump cartridge of clause 13, wherein the engagement structure comprises a plurality of fingers to engage the pushrod and optionally wherein the engagement structure comprises a plurality of snap-on piston clips connected to the piston and configured to engage a recess or a protrusion of the pushrod.

Clause 29. The pump cartridge of clause 13, wherein the casing comprises a slot to receive the pushrod with movement of the cartridge transverse to an elongate axis of the pushrod and wherein the engagement structure comprises a slot to receive the pushrod and a protrusion to engage a recess in the pushrod and optionally wherein the protrusion coupled to a spring to couple the protrusion to the recess and optionally wherein the recess comprises a detent and the protrusion comprises a ball.

Clause 30. The pump cartridge of clause 13, wherein the housing comprises a fastener to couple the cartridge to a console in order to fasten the cartridge to the console and optionally wherein the console comprises a motor and the pushrod.

Clause 31. The pump cartridge of clause 30, wherein the housing comprises a fastener comprising one or more of an extension of the housing, a plurality of extensions of the housing, a pair of opposing extensions extending from the housing, a recess in the housing, plurality of recesses in the housing, a groove in the housing, a plurality of grooves in the housing, an aperture extending through the housing, a plurality of apertures extending through the housing and optionally wherein the housing comprises metal to fasten the cartridge to the console.

Clause 32. The pump cartridge of clause 31, wherein the fastener is sized and shaped to engage a stop of a console on a first side of the fastener and a movable locking structure of the console on a second side to fasten the cartridge to the console.

Clause 33. The pump cartridge of clause 32 wherein the movable locking structure of the console comprises a pin to contact the second side of the fastener.

Clause 34. The pump cartridge of clause 32 wherein the first side comprises a first surface facing in a first direction of axial force with advancement of the piston toward an outlet to direct compressive force of the cylinder toward the stop and the second side comprises a second surface facing in a second direction of axial force corresponding to retraction of the piston away from the outlet in a direction corresponding to drawing fluid into the cylinder.

Clause 35. The pump cartridge of clause 1, further comprising a seal located in the channel, the seal configured to allow movement of the piston relative to the seal.

Clause 36. The pump cartridge of clause 35, further comprising a retainer coupled to the seal, wherein the retainer is configured to limit movement of the seal relative to the piston when the piston moves in the cylinder and optionally wherein the retainer works against fluid pressure within the cylinder, the fluid in the cylinder acting in an opposite direction of the piston during a power stroke to urge the seal against the retainer.

Clause 37. The pump cartridge of clause 35, wherein the seal comprises one or more of an O-ring, a cup seal, or a saddle sleeve.

Clause 38. The pump cartridge of clause 35, wherein pump channel comprises a second portion sized to receive the seal and wherein the cylinder comprises a first portion of the channel.

Clause 39. The pump cartridge of clause 38, wherein the engagement structure is configured to couple to the pushrod with a first amount of axial force, the engagement structure is configured to decouple from a retention structure with a second amount of axial force, the piston is configured to slide along the seal with a third amount of axial force, and wherein the second amount of axial force is greater than the first and third amounts of axial force.

Clause 40. The pump cartridge of clause 39, wherein the third amount of axial force is less than the first amount of axial force.

Clause 41. The pump cartridge of clause 39, wherein the third amount of axial force is greater than the first amount of axial force.

Clause 42. The pump cartridge of clause 39, wherein the engagement structure is configured to decouple from the pushrod with a fourth amount of axial force, the fourth amount of axial force greater than the first and third amounts of axial force.

Clause 43. The pump cartridge of clause 42, wherein first, second and third amounts of axial force are in a first direction and the fourth axial force is in a second direction opposite the first direction.

Clause 44. The pump cartridge of clause 42, wherein the fourth amount of axial force is greater than the second amount of axial force.

Clause 45. The pump cartridge of clause 42, wherein the fourth amount of axial force is less than the second amount of axial force.

Clause 46. The pump cartridge of clause 42, wherein the retention structure is configured to one or more of deform or break the engagement structure with the fourth amount of force to inhibit coupling of the engagement structure to the pushrod subsequent to decoupling the pushrod from the engagement structure.

Clause 47. The pump cartridge of clause 35, wherein the channel comprises a second portion located toward the engagement structure, the second portion sized to retain the seal, the second portion comprising a cross-section sized larger than a cross-section of the cylinder and optionally wherein the cylinder comprises a first cross-sectional diameter the second portion comprises a second cross-sectional diameter, the first cross-sectional diameter smaller than the second cross-sectional diameter to retain the seal in the second portion when the piston reciprocates.

Clause 48. The pump cartridge of clause 47, wherein second portion comprises a cylinder.

Clause 49. The pump cartridge of clause 1, wherein the piston comprises a plurality of pistons, the cylinder comprises a plurality of cylinders, the engagement structure comprises a plurality of engagement structures, and the pushrod comprises a plurality of pushrods.

Clause 50. The pump cartridge of clause 1, further comprising a seal and a bushing, the seal and the bushing at least partially within the channel.

Clause 51. The pump cartridge of clause 50, wherein the piston coupled to a retention structure provides a gap between the piston and the seal to allow a sterilizing gas to travel from the outside the housing into the cylinder.

Clause 52. The pump cartridge of clause 50, wherein the seal comprises an inner unloaded diameter prior to engaging the piston and the piston comprises an outer diameter, the inner unloaded diameter of the seal less than the diameter of the piston, and optionally wherein the seal is configured to deflect to a diameter of the piston to engage the piston.

Clause 53. The pump cartridge of clause 50, wherein the piston comprises an outer diameter and the cylinder comprises an inner diameter, the inner diameter greater of the cylinder than the outer diameter of the piston to provide a gap between the piston and the cylinder when the piston has been inserted through the seal and into the cylinder.

Clause 54. The pump cartridge of clause 53, wherein the piston is sized to displace fluid within the cylinder with a gap extending between a distal portion of the piston and the cylinder.

Clause 55. The pump cartridge of clause 50, wherein bushing comprises an inner bearing surface to guide the piston, the seal located between the bearing surface and the cylinder.

Clause 56. The pump cartridge of clause 50, further comprising a retainer to couple to the housing and retain the bushing with the seal located between the retainer and the cylinder and optionally wherein the channel comprises a second cylinder with an inner diameter greater than the cylinder and optionally further comprising a stop located between the cylinder and the second cylinder to limit movement of the bushing toward the cylinder.

Clause 57. A pump cartridge comprising: a first piston and a second piston; a housing comprising a first inlet and a second inlet, an outlet, a first cylinder to receive the first piston, a second cylinder to receive the second piston; and a valve located between the first inlet and the second inlet, wherein the valve comprises a movable component that translates from a first position to a second position, wherein the first position allows liquid to flow from the first inlet to the first cylinder and from the second cylinder to the outlet and wherein the second position allows liquid to flow from the second inlet to the second cylinder and from the first cylinder to the outlet.

Clause 58. The pump cartridge of clause 57, wherein an output pressure of the second cylinder urges the movable component into the first position and an output pressure of the first cylinder urges the movable component to the second position.

Clause 59. The pump cartridge of clause 57, wherein a channel extends from the first inlet to the second inlet with the valve positioned therebetween.

Clause 60. The pump cartridge of clause 59, wherein the channel comprises a first portion extending from the first inlet to the first cylinder and a second portion extending from the second cylinder to the second inlet with the valve located between the first portion and the second portion with the valve in both the first position.

Clause 61. The pump cartridge of clause 60, wherein in the first position the valve engages a first valve seat to inhibit flow of a first high pressure fluid from the second cylinder toward the first cylinder and wherein in the second position the valve engages a second valve seat to inhibit flow of second high pressure fluid from the first cylinder.

Clause 62. The pump cartridge of clause 59, wherein the channel extends transverse to a first elongate axis of the first cylinder and a second elongate axis of the second cylinder.

Clause 63. The pump cartridge of clause 62, wherein the channel extends transverse to a first elongate axis of the first cylinder and a second elongate axis of the second cylinder and optionally wherein the channel extends perpendicularly to the first elongate axis and the second elongate axis.

Clause 64. The pump cartridge of clause 57, further comprising a first valve seat to engage the movable component in the first position and a second valve seat to engage the valve in the second position.

Clause 65. The pump cartridge of clause 64, wherein an outlet channel is coupled to the channel between the first valve seat and the second valve seat.

Clause 66. The pump cartridge of clause 64, wherein the first valve seat and the second valve seat each comprises a ductile material in order to shape a surface of the first valve seat to the movable component and the second valve seat to the movable component.

Clause 67. The pump cartridge of clause 64, wherein the first valve seat and the second valve seat each comprises a material softer than the movable component.

Clause 68. The pump cartridge of clause 64, wherein the first valve seat and the second valve seat each comprises a tapered end to engage the movable component and optionally wherein the tapered end comprises an angle of inclination within a range from about 1 degree to about 75 degrees relative to plane defined by a movable component engaging portion of the valve seat and optionally wherein the range is from about 10 degrees to about 45 degrees.

Clause 69. The pump cartridge of clause 64, wherein the movable component comprises a maximum cross-sectional dimension sized to fit in the channel and a thickness no more than the maximum cross-sectional dimension.

Clause 70. The pump cartridge of clause 69, wherein the moveable component comprises a profile around a perimeter, wherein the profile defines one or more channels to allow fluid to pass through the channels from the first cylinder to the outlet when the movable component is located away from the first valve seat and from the second cylinder to the outlet when the movable component is located away from the second valve seat.

Clause 71. The pump cartridge of clause 70, wherein the movable component comprises a valve seat engaging portion sized and shaped to engage the valve seat and a channel portion sized and shaped to define the one or more channels, wherein the valve seat engaging portion is located radially inward from the channel portion.

Clause 72. The pump cartridge of clause 70, wherein the perimeter of the movable component corresponds to one or more of a star shape, a D shape, a polygon, a triangle, a rectangle, an ellipsoid, or a crescent.

Clause 73. The pump cartridge of clause 64, wherein the movable component comprises a disc comprising a diameter sized to engage the first valve seat and the second valve seat, and wherein the first valve seat is spaced apart from the second valve seat along the channel by a distance greater than a thickness of the disc.

Clause 74. The pump cartridge of clause 73, wherein an outflow channel is coupled to the outlet, the distance between the valve seats, the thickness of the disc and a diameter of the outflow channel are dimensioned to permit fluid to flow to the outflow channel when the first piston pressurizes the first cylinder and the disc engages the second seat and the second piston pressurizes the second cylinder and the disc engages the first valve seat.

Clause 75. The pump cartridge of clause 69, wherein the movable component comprises a first surface to engage the first valve, and a second surface to engage the second valve, a stiff extension extending between the first surface to couple the first surface to the second surface in order to move the second surface toward the second valve seat and the first surface away from the first valve seat with pressurization of the first cylinder and to move the first surface toward the first valve seat and the second surface away from the second valve seat with pressurization of the second cylinder.

Clause 76. The pump cartridge of clause 69, wherein the movable component comprises a spherically shaped ball.

Clause 77. The pump cartridge of clause 64, wherein the movable component comprises a first movable component and a second moveable component, the first movable component located proximate the first valve seat, the second movable component located proximate the second valve seat, wherein output pressure from the first cylinder urges the first movable component away from the first valve seat and the second movable component toward the second valve seat.

Clause 78. The pump cartridge of clause 77, wherein pumping efficiency is increased in response to back pressure from an output hose, in which said back pressure influences an open valve to close faster before an opposing cylinder drives a closed valve open.

Clause 79. The pump cartridge of clause 77, wherein a spring is coupled to the first movable component and the second movable component and optionally wherein said spring is located within the channel and extends along the channel between the first movable component and said second movable component.

Clause 80. The pump cartridge of clause 79, wherein the spring increases a close time of when a piston is located at top dead center and decreases a cross cylinder interference and optionally wherein said spring comprises a spring constant configured to increase said close time decrease the cross cylinder interference, and optionally wherein a mass of said first movable component, a mass of said second movable component and said spring constant are arranged so as to correspond to a resonance frequency suitable for decreasing said close time and said cross cylinder interference.

Clause 81. The pump cartridge of clause 79, wherein the spring comprises one or more of a tension spring, compression spring, or an outside actor to close the valves.

Clause 82. The pump cartridge of clause 77, further comprising a first stop and a second stop, the first movable component located between the first valve seat and the first stop to limit movement of the first movable component away from the first valve seat, the second movable component located between the second valve seat and the second stop to limit movement of the second movable component away from the second valve seat and optionally wherein the first stop and the second stop are located between the first movable component and the second movable component.

Clause 83. A pump cartridge comprising: a piston; a housing comprising an inlet, an outlet, and a first cylinder to receive the piston, a second cylinder to receive a second piston; and a valve comprising a valve seat and a movable component that translates from a first position away from the valve seat a second position to engage the valve seat, wherein the first position allows liquid to flow from the inlet to the cylinder and wherein the second position inhibits flow from the cylinder to the inlet, wherein the valve seat comprises a ductile material to shape a surface of the valve seat to the movable component in response to pressure from the cylinder.

Clause 84. The pump cartridge of clause 83, wherein the valve seat comprises a material softer than the movable component.

Clause 85. The pump cartridge of clause 83, wherein the valve seat comprises a material harder than the movable component.

Clause 86. The pump cartridge of clause 83, wherein the valve seat comprises stainless steel.

Clause 87. The pump cartridge of clause 83, wherein the valve seat comprises a tapered end to engage the movable component and optionally wherein the tapered end comprises an angle of inclination within a range from about 1 degree to about 75 degrees relative to plane defined by a moveable component engaging portion of the valve seat and optionally wherein the range is from about 10 degrees to about 45 degrees.

Clause 88. The pump cartridge of clause 87, wherein the tapered end comprises an annular edge to engage the movable component.

Clause 89. The pump cartridge of clause 88, wherein the annular edge comprises a sharp annular edge.

Clause 90. The pump cartridge of clause 88, wherein the annular edge comprises a radial thickness within a range from about 0.0001 mm to about 0.25 mm and optionally from 0.01 mm to about 0.25 mm.

Clause 91. The pump cartridge of clause 87, wherein the movable component comprises a substantially flat surface to engage the tapered end and optionally wherein the flat surface comprises a uniformity within a range from about 0.1 mm to about 0.010 mm.

Clause 92. The pump cartridge of clause 91, wherein the substantially flat surface comprises a substantially flat surface of an annular groove.

Clause 93. The pump cartridge of clause 83, wherein the movable component comprises a profile around a perimeter, wherein the profile defines one or more channels to allow fluid to pass through the channels from the first cylinder to the outlet when the movable component is located away from the valve seat and from the second cylinder to the outlet when the movable component is located away from the second valve seat.

Clause 94. The pump cartridge of clause 93, wherein the movable component comprises a valve seat engaging portion sized and shaped to engage the valve seat and a channel portion sized and shaped to define the one or more channels, wherein the valve seat engaging portion is located radially inward from the channel portion.

Clause 95. The pump cartridge of clause 94, wherein the perimeter of the movable component corresponds to one or more of a star shape, a D shape, a polygon, a triangle, a rectangle, an ellipsoid, or a crescent.

Clause 96. A pump console, comprising: a receptacle to receive a pump cartridge; a locking structure to engage a fastener of the pump cartridge; a pushrod to engage the pump cartridge; an actuator coupled to the pushrod; and a processor coupled to an actuator to move the pushrod, the processor configured to advance the pushrod into the cartridge in response to the locking structure engaging the fastener.

Clause 97. The pump console of clause 96, wherein the processor is configured to advance the pushrod into the cartridge a first distance to decouple a piston from a retention structure of the piston and advance the piston into a seal of the cartridge and to advance the pushrod into the cartridge a second distance to a top dead center of the piston with reciprocal motion of the piston.

Clause 98. The pump console of clause 96, wherein the console comprises an engagement structure on the pushrod to engage a piston of the pump cartridge and optionally wherein the engagement structure is configured to decouple the piston from a retention structure coupled to the piston and optionally wherein the engagement structure is configured to draw the piston away from a valve of the piston subsequent to engagement.

Clause 99. The pump console of clause 96, wherein the console comprises an engagement structure on the pushrod to engage a piston of the pump cartridge.

Clause 100. The pump console of clause 96, further comprising a return spring to urge a piston of a pump cartridge toward a pushrod of the pump console when the pushrod retracts away from a top dead center of the piston.

Clause 101. The pump console of clause 100, wherein the spring comprises one or more of a torsion spring, a coil spring or a leaf spring and optionally wherein the spring provides an amount of force to the piston within a range from about 1 pound to about 20 pounds between bottom dead center and top dead center of the piston in a cylinder and optionally wherein the amount is within a range from about 2 to 15 pounds and optionally from about 5 to 10 pounds.

Clause 102. The pump console of clause 100, wherein the console further comprises a slider coupled to the spring, the slider configured to compress the spring with advancement of a piston of the pump cartridge, the slider coupled to a receiver to receive the piston and urge the piston toward with pushrod with retraction of the pushrod.

Clause 103. The pump console of clause 96, further comprising a rocker arm on the console to provide reciprocal motion of a first piston and a second piston of the pump cartridge.

Clause 104. The pump console of clause 103, wherein said rocker arm comprises a first pushrod engagement portion to couple to a first pushrod and a second pushrod engagement portion to couple to a second pushrod, a pivot axis extending there between, wherein advancement of said first pushrod and said first pushrod engagement portion corresponds to advancement of a first piston and urges said second pushrod engagement portion in an opposite direction corresponding to retraction of a second piston of a pump cartridge.

Clause 105. The pump console of clause 96, further comprising an engagement structure located on the pushrod of the console prior to placement of the console on the pushrod, the engagement structure configured to engage a piston of the pump cartridge with axial advancement of the pushrod toward the piston.

Clause 106. The pump console of clause 105, wherein said engagement structure comprises a plurality of fingers to engage a piston of the pump cartridge.

Clause 107. The pump console of clause 105, wherein said engagement structure comprises a tension bushing with one or more balls to engage a piston of the cartridge.

Clause 108. The pump console of clause 105, wherein said engagement structure is configured to decouple from said piston with a first amount of axial force and to decouple from said pushrod with a second amount of axial force, wherein said second amount of axial force is greater than said first amount of axial force and optionally wherein said engagement structure comprises a first snap on clip to couple to the piston and a second snap on clip configured to couple to the pushrod, and wherein said engagement structure comprises a user removable part of the console.

Clause 109. The pump console of clause 105, wherein said engagement structure is configured to retract said piston with an amount of force within a range from about 1 pound to about 20 pounds.

Clause 110. The pump console of clause 96, wherein said receptacle is sized and shaped to receive the pump cartridge with axial movement of the pump cartridge.

Clause 111. The pump console of clause 110, wherein said receptacle comprises one or more of a threaded member, a tapered channel, or a cam on pins to receive said cartridge into the receptacle.

Clause 112. The pump console of clause 111, wherein said receptacle comprises the threaded member configured to rotate and draw the cartridge into the fastened position and optionally wherein said threaded member comprises one or more of a bolt, a screw or a rotating member comprising internal threads and optionally wherein said receptacle comprises springs coupled to a tray to urge the cartridge toward the threaded member to engage the cartridge.

Clause 113. The pump console of clause 111, wherein said receptacle comprises the tapered channel, said tapered channel sized to receive a tapered portion of the cartridge with axial advancement of the cartridge, optionally wherein the receptacle further comprising movable member to extend into the cartridge to fasten the cartridge, said movable member optionally comprising a protrusion sized and shaped to extend into a casing of the cartridge and optionally wherein the tapered portion of the cartridge nests with the tapered channel of the receptacle.

Clause 114. The pump console of clause 111, wherein the receptacle comprises a cam to engage a protruding structure of the cartridge to advance the cartridge axially and optionally wherein the protruding structure comprises a pin to engage the cam.

Clause 115. The pump console of clause 96, wherein said receptacle is sized and shaped to receive the pump cartridge with movement of the pump cartridge transverse to a reciprocating piston and cylinder axis of the pump cartridge and optionally wherein said movement comprises a top down loading of the pump cartridge of a side sliding movement of the pump cartridge.

Clause 116. The pump console of clause 115, wherein the receptacle comprises a clamp to fasten the cartridge into the receptacle and optionally wherein said clamp comprises a lever lid to fasten the cartridge to the receptacle from above the cartridge.

Clause 117. The pump console of clause 115, wherein the receptacle comprises a groove to receive a protrusion of the cartridge and wherein the groove extends in a first direction to receive the cartridge with movement in a first direction and the groove extends in a second direction transverse to the first direction to direct the cartridge toward a fastened position and optionally wherein the first direction extends substantially horizontally and the second direction extends substantially vertically and optionally wherein the groove comprises a pair of grooves to receive a pair of protrusions on opposite sides of the cartridge.

Clause 118. The pump console of clause 96, wherein the pushrod comprises a plurality of pushrods, the processor configured to advance the plurality of pushrods into the cartridge a first plurality of distances to decouple a plurality of pistons from a plurality of retention structures coupled to the plurality of pistons and advance the plurality of pistons into a plurality of seals of the cartridge and to advance the plurality of pushrods into the cartridge a second plurality of distances to a plurality of top dead centers of the plurality of pistons with reciprocal motion of the plurality of pistons and optionally wherein the actuator is configured to drive the plurality of pistons out of phase to linearize and output flow rate of fluid from cartridge.

Clause 119. The pump console of clause 96, wherein the actuator comprises one or more of transmission, a cam, a motor, a crankshaft, or a dual lobe crankshaft.

Clause 120. The pump console of clause 96, further comprising a transmission, the transmission comprising a crankshaft and a plurality of connecting rods coupled to a plurality of pushrods.

Clause 121. The pump console of clause 96, further comprising a cartridge loader to load the pump cartridge into the receptacle.

Clause 122. The pump console of clause 96, further comprising a transmission and a motor.

Clause 123. The pump console of clause 96, further comprising a plurality of sensors, the plurality of sensors comprising one or more of a cartridge in place sensor to detect the cartridge being in place, a fasteners sensor to sense a movable component fastening the sensor, a dead center sensor to sense a piston in a distal most position advanced into a cylinder, a gate down sensor, a gate up sensor or a cartridge code reader.

Clause 124. The pump console of clause 96, further comprising a plurality of sensors and a movable component to fasten the pump cartridge in the receptacle, the plurality of sensors comprising a first fastener sensor to sense the movable component fastening the cartridge into the receptacle and a second fastener sensor to sense a home position of the movable component.

Clause 125. The pump console of clause 96, further comprising a carriage, wherein the pushrod is supported on the carriage, the carriage comprising a first position for placement of the cartridge in the receptacle and a second position to engage the piston with the pushrod for reciprocal motion.

Clause 126. The pump console of clause 125, wherein carriage is configured to advance the pushrod from the first position to the second position.

Clause 127. The pump console of clause 125, wherein carriage the carriage supports the actuator and the carriage is configured to advance the actuator and the pushrod from the first position to the second position.

Clause 128. The pump console of clause 96, further comprising the pump cartridge of any one of the preceding clauses.

Clause 129. The pump cartridge or pump console of any one of the preceding clauses, further comprising a sterile package and wherein the pump cartridge comprises a sterile pump cartridge within the sterile package and optionally wherein the pump cartridge has been sterilized with a gas and optionally wherein the gas comprises Ethylene Oxide (EtO).

Clause 130. The pump cartridge or pump console of any one of the preceding clauses, wherein the piston comprises a plurality of pistons and the cylinder comprises a plurality of cylinders.

Clause 131. The pump cartridge or pump console of any one of the preceding clauses, wherein the pushrod comprises a control rod.

Clause 132. The pump cartridge or pump console of any one of the preceding clauses, further comprising an external actuator outside coupled to the movable component of the valve to move the moveable component of the valve into the valve seat.

Clause 133. The pump cartridge or pump console of any one of the preceding clauses, wherein the pump cartridge comprises a unique identifier and optionally wherein the unique identifier comprises one or more of a QCR code, a bar code, or an RFID.

Clause 134. The pump cartridge or pump console of any one of the preceding clauses, wherein the console comprises a reader to read a unique identifier of the pump cartridge and wherein the processor is coupled to the reader to receive the unique identifier and compare the unique identifier to a library of unique identifiers and optionally wherein the processor comprises instructions to advance the pushrod into the pump cartridge in response to reading a valid unique identifier from the pump cartridge.

Clause 135. The pump cartridge or pump console of any one of the preceding clauses, wherein the console is configured to drive the piston at a frequency within a range from about 10 Hertz (Hz) to about 200 Hertz and optionally within a range from about 50 Hz to 200 Hz.

Clause 136. The pump cartridge or pump console of any one of the preceding clauses, further comprising a high pressure fluid line and a nozzle coupled to the high pressure fluid line, wherein the high pressure line is configured to undergo volumetric expansion upon pressurization and the nozzle is configured to provide resistance to fluid flow, and wherein in combination of the high pressure fluid line and nozzle are configured to provide a more uniform pressure and fluid flow through the nozzle and optionally wherein the pressure and corresponding fluid flow are uniform to within a range from about 25% (percent) to about 1% over a plurality of pump cycles and optionally to within about 15% to about 5% and optionally wherein the uniformity within the range is provided with a pump frequency of 50 Hz and optionally within a range of pump frequencies from about 25 Hz to about 100 Hz and optionally wherein the fluid line comprises a length within a range from about 0.2 meters to about 3 meters and optionally from about 0.5 meters to about 2 meters.

Clause 137. A method comprising: coupling a pump cartridge to a pump console.

Clause 138. The method of clause 137, further comprising coupling the pump cartridge of any one of the preceding clauses to the pump console of any one of the preceding clauses.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A pump cartridge comprising:
   a piston;
   a housing comprising a channel, an inlet, and an outlet, the channel comprising a cylinder shaped to receive the piston;
   an engagement structure to couple the piston to a pushrod in response to axial movement of the pushrod or the housing; and
   a casing over a portion of the housing, wherein the engagement structure is supported with outside the channel;
   wherein the piston is connected to the engagement structure and the engagement structure is connected to the casing in a storage configuration with the piston outside the cylinder in order to permit a sterilization gas to flow from an interior of the casing into the cylinder and wherein the casing comprising an opening to allow the sterilization gas to flow from an exterior of the casing to the interior of the casing and into the cylinder.

2. The pump cartridge of claim 1, wherein the engagement structure is connected to the casing and configured to decouple from the casing with axial advancement of the pushrod.

3. The pump cartridge of claim 2, wherein the casing comprises an opening to receive the pushrod and wherein the engagement structure extends through the opening from the interior of the casing to the exterior of the casing.

4. The pump cartridge of claim 3, wherein an exterior portion of the engagement structure is configured to advance through the opening and into the interior of the casing when coupled to the pushrod.

5. The pump cartridge of claim 4, wherein the exterior portion of the engagement structure is configured to remain within the interior of the casing when decoupled from the pushrod.

6. The pump cartridge of claim 1, further comprising a retention structure connected to the casing to retain the engagement structure in a shipping configuration and to decouple from the engagement structure in response to axial force from the pushrod.

7. The pump cartridge of claim 6, wherein the retention structure comprises a plurality of inclined tabs configured to deflect upon axial advancement of the engagement structure toward the interior of the casing and to remove the engagement structure from the pushrod upon retraction of the pushrod from the interior.

8. The pump cartridge of claim 1, wherein a distal tip of the piston is located outside the cylinder and within the channel.

9. The pump cartridge of claim 1, wherein the engagement structure is configured to couple to the pushrod with a first amount of axial force and to decouple from the pushrod with a second amount of axial force greater than the first amount of force.

10. The pump cartridge of claim 9, wherein the first amount of axial force is oriented in a first direction and the second amount of axial force is oriented in a second direction.

11. The pump cartridge of claim 1, wherein the engagement structure is configured to deform upon decoupling from the pushrod.

12. The pump cartridge of claim 1, further comprising a retention structure coupled to the housing and the engagement structure, wherein the retention structure is configured to decouple from the engagement structure in response to the axial movement of the pushrod or the housing.

13. The pump cartridge of claim 12, further comprising a seal located in the channel, wherein the retention structure is configured to retain the engagement structure with the piston positioned in relation to the seal so as to define a gap between at least a portion of the piston and the seal in order to allow a sterilizing gas to enter the cylinder.

14. The pump cartridge of claim 12, wherein the retention structure is configured to retain the engagement structure with the piston positioned in relation to the cylinder so as to define a gap between at least a portion of the piston and the cylinder in order to allow the sterilizing gas to enter the cylinder.

15. The pump cartridge of claim 12, wherein the retention structure is configured to retain the engagement structure and release the engagement structure in response to axial advancement of the pushrod.

16. The pump cartridge of claim 15, wherein the retention structure comprises a plurality of extensions sized and shaped to engage a groove on the engagement structure, the plurality of extensions inclined toward the engagement structure and the inlet of the cylinder in order to allow the engagement structure to move toward the cylinder with axial advancement of the pushrod and to decouple the engagement structure from the pushrod with axial retraction of the pushrod away from the cylinder.

17. The pump cartridge of claim 16, wherein the engagement structure comprises the groove or a flange to receive the plurality of extensions to retain the engagement structure with the retention structure and wherein the plurality of extensions is configured to deflect radially away from the piston to allow advancement of the piston toward the cylinder.

18. The pump cartridge of claim 15, wherein the engagement structure is configured to engage the pushrod with a first amount of force and the retention structure is configured to decouple from the engagement structure with a second amount of force, the second amount of force greater than the first amount of force.

19. The pump cartridge of claim 18, wherein the engagement structure is configured to retain coupling between the pushrod and the piston with an amount of force sufficient to draw the piston proximally with reciprocal motion of the piston in the cylinder and the pushrod coupled to the piston.

* * * * *